US009114107B2

(12) United States Patent
Chaiken et al.

(10) Patent No.: US 9,114,107 B2
(45) Date of Patent: Aug. 25, 2015

(54) COMPOSITIONS FOR INHIBITING VIRUS ENTRY AND PROMOTING VIROLYSIS, AND METHODS THEREOF

(75) Inventors: Irwin Chaiken, Gladwyne, PA (US); Elisabeth S. Papazoglou, Yardley, PA (US); Constantinos Papathomas, legal representative, Yardley, PA (US); Arangassery Rosemary Bastian, Philadelphia, PA (US); Kantharaju, Philadelphia, PA (US)

(73) Assignee: Drexel University, Philadelphia, PA (US)

( * ) Notice: Subject to any disclaimer, the term of this patent is extended or adjusted under 35 U.S.C. 154(b) by 0 days.

(21) Appl. No.: 13/876,876

(22) PCT Filed: Oct. 5, 2011

(86) PCT No.: PCT/US2011/054969
§ 371 (c)(1),
(2), (4) Date: Nov. 5, 2013

(87) PCT Pub. No.: WO2012/048033
PCT Pub. Date: Apr. 12, 2012

(65) Prior Publication Data
US 2014/0050793 A1 Feb. 20, 2014

Related U.S. Application Data

(60) Provisional application No. 61/390,055, filed on Oct. 5, 2010.

(51) Int. Cl.
*A61K 38/10* (2006.01)
*C07K 7/08* (2006.01)
*A61P 31/14* (2006.01)
*A61K 38/08* (2006.01)
*A61K 45/06* (2006.01)
*C07K 7/02* (2006.01)
*A61K 47/48* (2006.01)
*A61K 31/555* (2006.01)
*C07D 211/58* (2006.01)
*C07D 471/04* (2006.01)

(52) U.S. Cl.
CPC .............. *A61K 38/10* (2013.01); *A61K 31/555* (2013.01); *A61K 38/08* (2013.01); *A61K 45/06* (2013.01); *A61K 47/48861* (2013.01); *C07D 211/58* (2013.01); *C07D 471/04* (2013.01); *C07K 7/02* (2013.01); *C07K 7/08* (2013.01)

(58) Field of Classification Search
CPC ... A61K 38/08; A61K 45/06; A61K 2300/00; A61K 47/48861; A61K 31/555; A61K 38/10; C07K 7/02; C07K 7/08; C07D 211/58; C07D 471/04
See application file for complete search history.

(56) References Cited

U.S. PATENT DOCUMENTS

2006/0165751 A1 7/2006 Chudzik et al.
2007/0054337 A1 3/2007 Ferning et al.
2010/0216721 A1 8/2010 Gopi et al.

FOREIGN PATENT DOCUMENTS

WO WO 2008/150444 A1 * 12/2008 ............. A61K 38/00

OTHER PUBLICATIONS

Definition of moiety, from http://dictionary.reference.com/browse/moiety, pp. 1-3, accessed Aug. 26, 2010.*
Gupta et al, Hydrogels: from controlled release to pH-responsive drug delivery, DDT, 2002, 7, pp. 569-579.*
Martinez-Avila, et al., "Gold Manno-Glyconanoparticles: Multivalent Systems to Block HIV-1 pg120 Binding to the Lectin DC-SIGN+", Chem Eur J 2009, vol. 15, pp. 9874-9888.
International Search Report; PCT/US2011/054969, dated Apr. 25, 2012.
Schon et al., "Thermodynamics of Binding of a Low-Molecular-Weight CD4 Mimetic to HIV-1 gp120", Biochemistry, 2006, vol. 45, pp. 10973-10980.
Zhao et al., "N-phenyl-N'-(2,2,6,6-tetramethyl-piperidin-4-yl)-oxalamides as a new class of HIV-1 entry inhibitors that prevent gp120 binding to cD4", Virology, 2005, vol. 339, p. 213-225.
Si et al., "Small-molecule inhibitors of HIV-1 entry block receptor-induced conformational changes in the viral envelope glycoproteins", PNAS, Apr. 6, 2004, vol. 1001, No. 14, pp. 5036-5041.
Guo et al., "Biochemical and Genetic Characterizations of a Novel Human Immunodeficiency Virus Type 1 Inhibitor That Blocks gp120-CD4 Interactions", Journal of Virology, Oct. 2003, vol. 77, No. 19, pp. 10528-10536.
Lin et al., "A small molecule HIV-1 inhibitor that targets the HIV-1 envelope and inhibits CD4 receptor binding", PNAS, Sep. 16, 2003, vol. 100, No. 19, pp. 11013-11018.
Veazey et al., "Protection of macaques from vaginal SHIV challenge by vaginally delivered inhibitors of virus-cell fusion", NATURE, Nov. 3, 2005, vol. 438, pp. 99-102.
McKnight et al., "Blocking the docking of HIV-1", PNAS, Sep. 16, 2003, vol. 100, No. 19, pp. 10581-10582.

* cited by examiner

*Primary Examiner* — Julie Ha
*Assistant Examiner* — Li Ni Komatsu
(74) *Attorney, Agent, or Firm* — Saul Ewing LLP; Kathryn Doyle; Domingos J. Silva

(57) ABSTRACT

The present invention includes a composition comprising a gold nanoparticle complexed with a cysteine-containing compound. The invention also includes the method of preparing a composition comprising a gold nanoparticle complexed with a cysteine-containing compound. The invention further includes a method of causing virolysis of a virus using the compositions described therein. The invention further includes a method of inhibiting virus entry using the compositions described therein.

17 Claims, 31 Drawing Sheets

Fig. 1

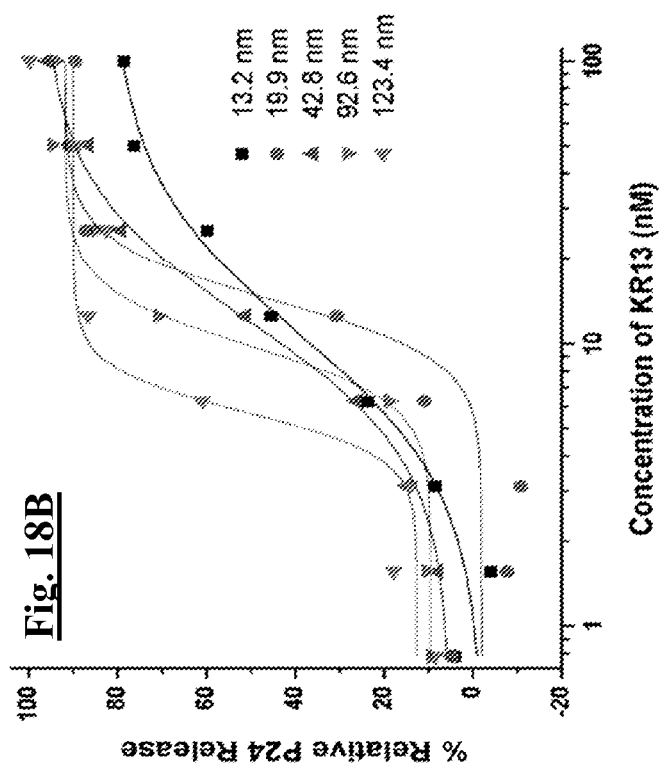
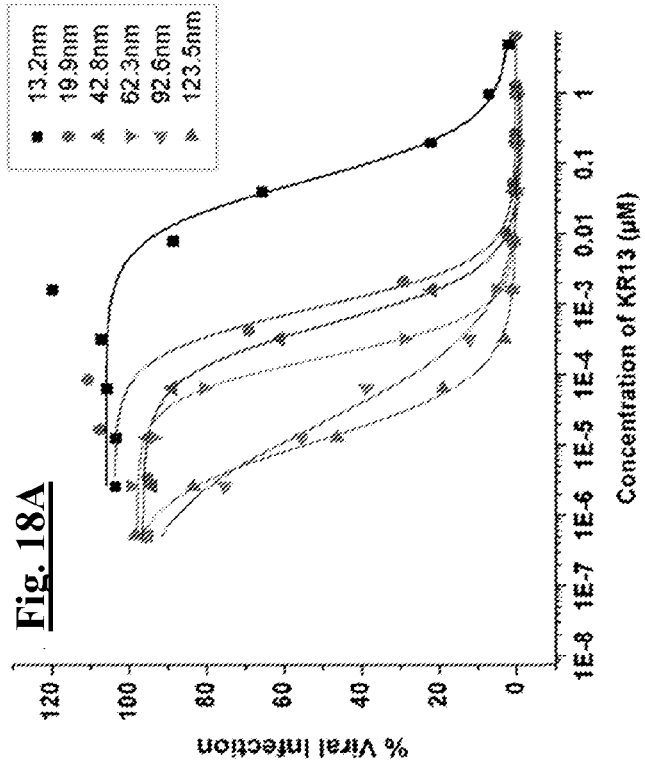
Fig. 18A
Fig. 18B

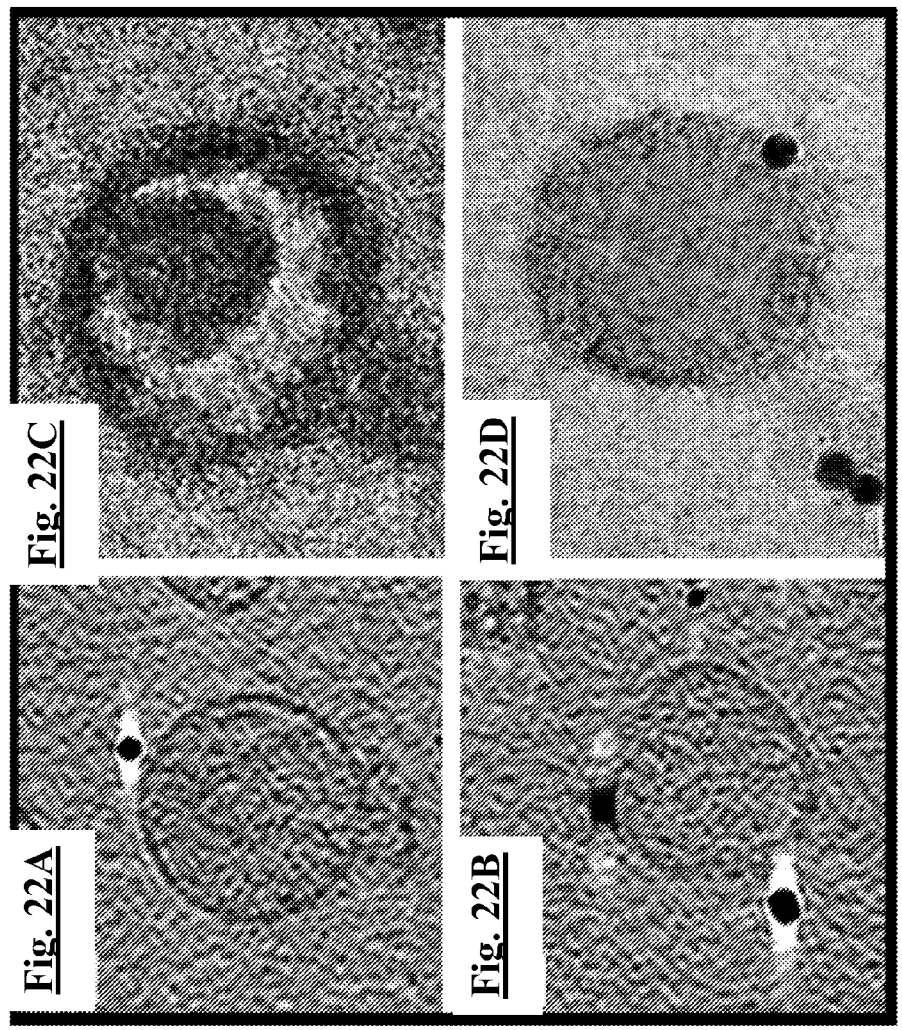

Fig. 23A
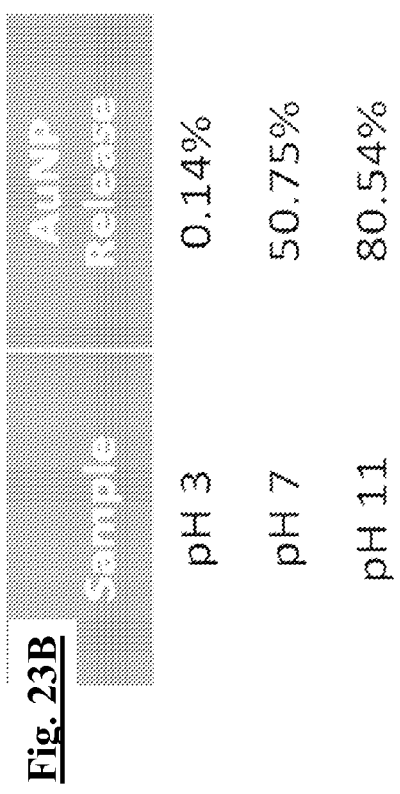
Fig. 23B
Figs. 23A-23B

SEQUENCE LISTING

<160> NUMBER OF SEQ ID NOS: 3

<210> SEQ ID NO 1
<211> LENGTH: 12
<212> TYPE: PRT
<213> ORGANISM: Artificial Sequence

```
<220> FEATURE:
<223> OTHER INFORMATION: Chemically synthesized
<220> FEATURE:
<221> NAME/KEY: MOD_RES
<222> LOCATION: (6)..(6)
<223> OTHER INFORMATION: (2,4)-4-(4-ferrocenyl-1H-1,2,3-triazol-1-yl)
      pyrrolidine-2-carboxylic acid

<400> SEQUENCE: 1

Arg Ile Asn Asn Ile Xaa Trp Ser Glu Ala Met Met
1               5                   10

<210> SEQ ID NO 2
<211> LENGTH: 16
<212> TYPE: PRT
<213> ORGANISM: Artificial Sequence
<220> FEATURE:
<223> OTHER INFORMATION: Chemically synthesized
<220> FEATURE:
<221> NAME/KEY: MOD_RES
<222> LOCATION: (6)..(6)
<223> OTHER INFORMATION: (2,4)-4-(4-ferrocenyl-1H-1,2,3-triazol-1-yl)
      pyrrolidine-2-carboxylic acid
<220> FEATURE:
<221> NAME/KEY: MOD_RES
<222> LOCATION: (13)..(13)
<223> OTHER INFORMATION: bAla
<220> FEATURE:
<221> NAME/KEY: MOD_RES
<222> LOCATION: (15)..(15)
<223> OTHER INFORMATION: bAla
<220> FEATURE:
<221> NAME/KEY: MOD_RES
<222> LOCATION: (16)..(16)
<223> OTHER INFORMATION: cysteine amide

<400> SEQUENCE: 2

Arg Ile Asn Asn Ile Xaa Trp Ser Glu Ala Met Met Xaa Gln Xaa Xaa
1               5                   10                  15

<210> SEQ ID NO 3
<211> LENGTH: 101
<212> TYPE: PRT
<213> ORGANISM: Neurospora crassa

<400> SEQUENCE: 3

Leu Gly Lys Phe Ser Gln Thr Cys Tyr Asn Ser Ala Ile Gln Gly Ser
1               5                   10                  15

Val Leu Thr Ser Thr Cys Glu Arg Thr Asn Gly Gly Tyr Asn Thr Ser
            20                  25                  30

Ser Ile Asp Leu Asn Ser Val Ile Glu Asn Val Asp Gly Ser Leu Lys
        35                  40                  45

Trp Gln Pro Ser Asn Phe Ile Glu Thr Cys Arg Asn Thr Gln Leu Ala
    50                  55                  60

Gly Ser Ser Glu Leu Ala Ala Glu Cys Lys Thr Arg Ala Gln Gln Phe
65                  70                  75                  80

Val Ser Thr Lys Ile Asn Leu Asp Asp His Ile Ala Asn Ile Asp Gly
                85                  90                  95

Thr Leu Lys Tyr Glu
            100
```

COMPOSITIONS FOR INHIBITING VIRUS ENTRY AND PROMOTING VIROLYSIS, AND METHODS THEREOF

CROSS-REFERENCE TO RELATED APPLICATIONS

The present application is a 35 U.S.C. §371 national phase application of, and claims priority to, International Application No. PCT/US2011/054969, filed Oct. 5, 2011, and published under PCT Article 21(2) in English, which claims priority under 35 U.S.C. §119(e) to U.S. Provisional Application No. 61/390,055, filed Oct. 5, 2010, all of which applications are hereby incorporated by reference in their entireties herein.

STATEMENT REGARDING FEDERALLY SPONSORED RESEARCH OR DEVELOPMENT

This invention was made with government support under grant numbers CBET-0853680 awarded by National Science Foundation, 5 POI GM 56550-13 and RO1 AI 084117-01 awarded by National Institutes of Health, and GPO-A-00-05-00041-00 awarded by International Partnership For Microbicides/U.S. Agency for International Development. The government has certain rights in the invention.

BACKGROUND OF THE INVENTION

The human immunodeficiency virus-1 (HIV-1) is responsible for a global epidemic, with over 33 million infected people worldwide. The lifecycle of HIV-1 has been extensively studied in the hope of identifying a therapeutic intervention that blocks viral transmission or viability. As an example, the Highly Active Anti-Retroviral Therapy (HAART) is a therapeutic approach targeting one or more stages of the HIV-1 life cycle. Favorable clinical results with HAART have shown that simultaneously targeting different stages of the viral life cycle may reduce the viral evolutionary escape mechanism that leads to drug resistance. Further, HAART may be more effective if administered simultaneously with other drugs that interrupt the initial entry stage of the virus life cycle. Unfortunately, existing entry inhibitors suffer from weak potency and toxicity issues.

The entry of HIV-1 into the host cell is mediated by interaction of a trimeric gp120/gp41 envelope (Env) protein complex with both cellular CD4 and chemokine co-receptor CCR5 or CXCR4. Each virus Env spike consists of a trimer of two non-covalently associated glycoproteins, an inner gp41 transmembrane protein and a gp120 exterior protein. The first step of viral entry is the interaction with CD4, leading to structural changes in the virus Env spike and exposing the chemokine binding domains of gp120. A structural change in the envelope spike exposes the fusion peptide sequence of gp41, enables the collapse of gp41 into a six-helix bundle leading to downstream membrane fusion and productive infection.

The HNG class of triazole conjugated peptides was derived from the 12mer parental peptide 12p1 (Gopi et al. 2009, 2009, J Mol Recog 22:169-174) by converting the proline at residue 6 of 12p1 into an azido-proline and performing copper-catalyzed (2+3) cycloaddition reactions of the azide with substituted acetylenes (Gopi et al., 2009, J. Mol. Recogn. 22:169-174, Gopi et al., 2008, J. Med. Chem. 51:2638-2647; Gopi et al., 2006, Chem Med Chem 1:54-57; Cocklin et al., 2007, J. Virol. 81:3645-3648). As a class, the HNG compounds have enhanced binding affinity for HIV-1 gp120, and were shown to block both CD4 and co-receptor sites with great efficacy. The HNG compounds appear to trap the gp120 protein in a non-functional state, distinct from the flexible ground state of gp120 or the CD4 induced conformation, and thus effectively halt the entry process at the initial binding stages. Using pseudotyped HIV-1 as well as isolated recombinant protein mutants, a binding footprint for the ferrocenyl triazole peptides was found to involve D474 and T257 (Tuzer et al., 2011, unpublished). These residues are adjacent to but not directly overlapping the CD4 binding site, and also overlap residues important for BMS-806 inhibition and a recently identified neutralizing antibody epitope (Lin et al., 2003, Proc. Natl. Acad. Sci. USA 100:11013-11018, Guo et al., 2003, J. Virol. 77:10528-10536; Pietzsch et al., 2010, J. Exp. Med. 207: 1995-2002). All of the 12p1 family members tested to date inhibit the binding of gp120 to both sCD4 (in a seemingly non-competitive manner) and the co-receptor surrogate mAb17b (Gopi et al., 2009, J. Mol. Recogn. 22:169-174; Gopi et al., 2008, J. Med. Chem. 51:2638-2647; Gopi et al., 2006, Chem Med Chem 1:54-57, Biorn et al., 2004, Biochemistry 43:1928-1938; Umashankara et al., 2010, Chem Med Chem 5:1871-1879).

The highest affinity candidate in the HNG series is the ferrocenyl triazole conjugate HNG156 (SEQ ID NO:1), wherein X is (2,4)-4-(4-ferrocenyl-1H-1,2,3-triazol-1-yl) pyrrolidine-2-carboxylic acid), which binds to monomeric gp120 with a $K_D$ of 7 nM, in contrast to the 2600 nM $K_D$ value of 12p1. The data so far suggest that HNG156 inhibition of the co-receptor binding site is allosteric and involves conformational entrapment of Env gp120 into an inactivated state (Lee et al., 2010, Anal. Bioanal. Chem. 396:1143-1152).

HNG156: Arg Ile Asn Asn Ile X Trp Ser Glu Ala Met Met-NH$_2$ (SEQ ID NO: 1)

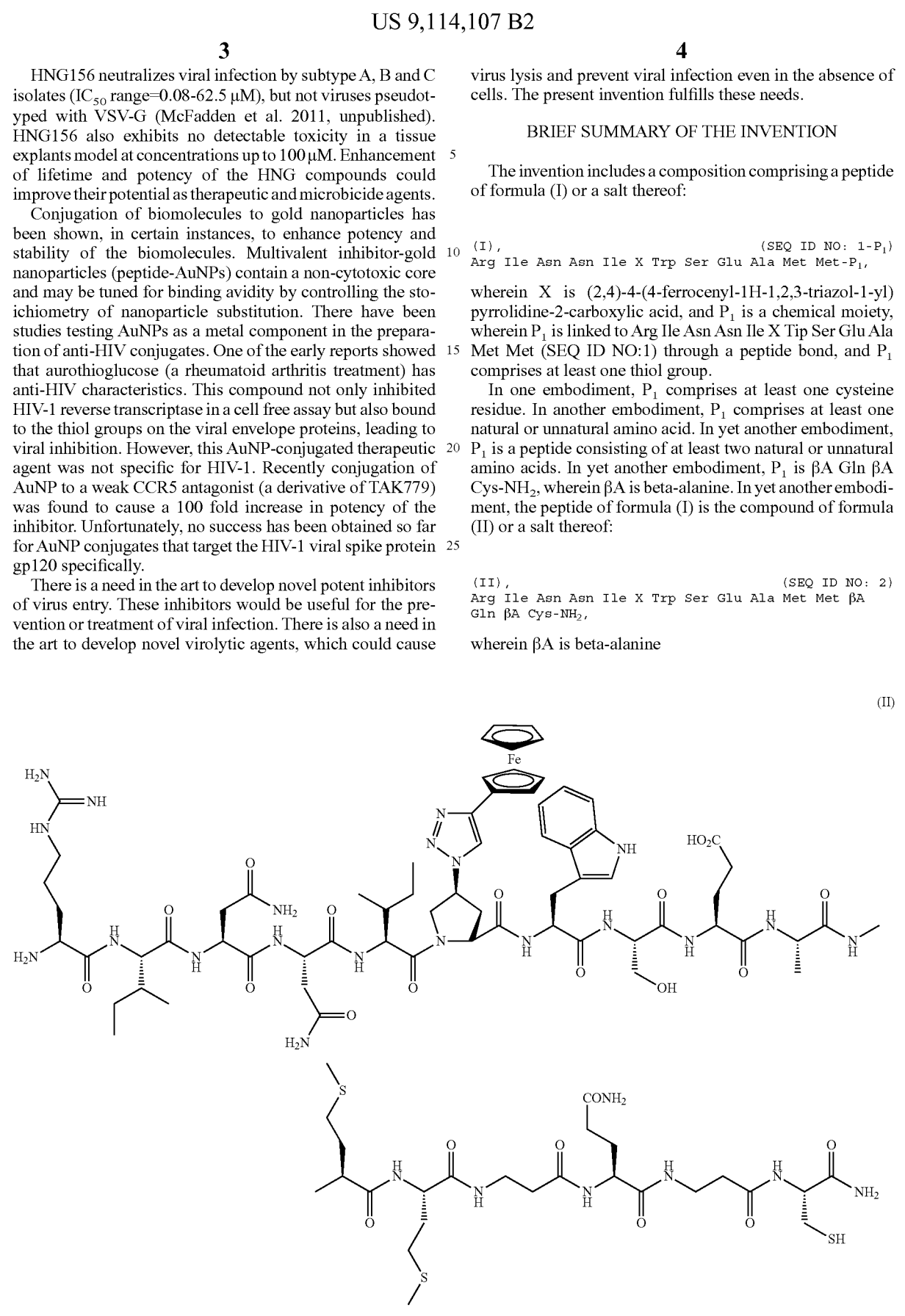

HNG156 neutralizes viral infection by subtype A, B and C isolates (IC$_{50}$ range=0.08-62.5 μM), but not viruses pseudotyped with VSV-G (McFadden et al. 2011, unpublished). HNG156 also exhibits no detectable toxicity in a tissue explants model at concentrations up to 100 μM. Enhancement of lifetime and potency of the In yet another embodiment, the composition further comprises at least one gold nanoparticle, wherein the at least one nanoparticle is complexed to the peptide of formula (I) through the at least one thiol group. In yet another embodiment, the at least one nanoparticle has an average diameter of about 20 nm. In yet another embodiment, the composition further comprises at least one pharmaceutically acceptable carrier. In yet another embodiment, the composition further comprises at least one additional compound useful for treating viral infections. In yet another embodiment, the at least one additional compound is selected from the group consisting of antiviral combination drugs, entry and fusion inhibitors, integrase inhibitors, non-nucleoside reverse transcriptase inhibitors, nucleoside reverse transcriptase inhibitors, protease inhibitors, and combinations thereof. In yet another embodiment, the peptide is encapsulated in a hydrogel. In yet another embodiment, the hydrogel is pH-responsive. In yet another embodiment, the hydrogel comprises a polymerized mixture of methacrylic acid and PEG-monomethyl ether monomethacrylate.

The invention also includes a composition comprising at least one gold nanoparticle, wherein the at least one gold nanoparticle is complexed with a binding molecule selected from the group consisting of:

a compound of formula $P_2$—$P_1$, wherein $P_2$ is selected from the group consisting of:

the compound of formula (III) [N-(4-chlorophenyl)-N'-(2,2,6,6-tetramethyl-piperidin-4-yl)-oxalamide]:

(III)

the compound of formula (IV) [N-(4-bromophenyl)-N'-(2,2,6,6-tetramethyl-piperidin-4-yl)-oxalamide]:

(IV)

and the compound of formula (V) [(R)-1-(4-benzoyl-2-methylpiperazin-1-yl)-2-(4-methoxy-1H-pyrrolo-[2,3-b]pyridin-3-yl)ethane-1,2-dione]:

(V)

wherein the NH group of the piperidinyl group in (III) or (IV), or the $N^1H$ group of the indole group in (V) is bound to $P_1$ through a peptide bond;

an anti-HIV-1-gp120 antibody selected from the group consisting of 17b, F105 and 2G12, wherein a carboxylic group or amine group in the $F_c$ region of the antibody is optionally bound to $P_1$ through a peptide bond; and, cyanovirin-N (SEQ ID NO:3), wherein a free amino group or carboxylate group of cyanovirin-N is optionally bound to $P_1$ through a peptide bond;

wherein $P_1$ is a chemical moiety, wherein $P_1$ comprises at least one thiol group;

wherein the nanoparticle is complexed to the binding molecule through a thiol group in the binding molecule.

In one embodiment, $P_1$ comprises at least one cysteine residue. In one embodiment, $P_1$ comprises at least one natural or unnatural amino acid. In yet another embodiment, $P_1$ is a peptide consisting of at least two natural or unnatural amino acids. In yet another embodiment, the at least one nanoparticle has an average diameter of about 20 nm. In yet another embodiment, the composition comprises at least one pharmaceutically acceptable carrier. In yet another embodiment, the composition comprises at least one additional compound useful for treating viral infections. In yet another embodiment, the at least one additional compound is selected from the group consisting of antiviral combination drugs, entry and fusion inhibitors, integrase inhibitors, non-nucleoside reverse transcriptase inhibitors, nucleoside reverse transcriptase inhibitors, protease inhibitors, and combinations thereof. In yet another embodiment, the peptide is encapsulated in a hydrogel. In yet another embodiment, the hydrogel is pH-responsive. In yet another embodiment, the hydrogel comprises a polymerized mixture of methacrylic acid and PEG-monomethyl ether monomethacrylate.

The invention also includes a method of preparing a derivatized gold nanoparticle, wherein the gold nanoparticle is complexed with a binding molecule or a salt thereof. The method comprises contacting a solution of the binding molecule with the nanoparticle, to generate a reaction system. the method further comprises stirring the reaction system for an amount of time, whereby the derivatized gold nanoparticle is formed. The method further comprises isolating the derivatized gold nanoparticle from the reaction system. The binding molecule selected from the group consisting of:

a peptide of formula (I) or a salt thereof:

(I; SEQ ID NO: 1-$P_1$)
Arg Ile Asn Asn Ile X Trp Ser Glu Ala Met Met-$P_1$, wherein X is (2,4)-4-(4-ferrocenyl-1H-1,2,3-triazol-1-yl) pyrrolidine-2-carboxylic acid, and $P_1$ is linked to Arg Ile Asn Asn Ile X Trp Ser Glu Ala Met Met through a peptide bond;

a compound of formula P₂—P₁, wherein P₂ is selected from the group consisting of:

the compound of formula (III) [N-(4-chlorophenyl)-N'-(2,2,6,6-tetramethyl-piperidin-4-yl)-oxalamide]:

(III)

the compound of formula (IV) [N-(4-bromophenyl)-N'-(2,2,6,6-tetramethyl-piperidin-4-yl)-oxalamide]:

(IV)

and the compound of formula (V) [(R)-1-(4-benzoyl-2-methylpiperazin-1-yl)-2-(4-methoxy-1H-pyrrolo-[2,3-b]pyridin-3-yl)ethane-1,2-dione]:

(V)

wherein the NH group of the piperidinyl group in (III) or (IV), or the N¹H group of the indole group in (V) is bound to P₁ through a peptide bond;
an anti-HIV-1-gp120 antibody selected from the group consisting of 17b, F105 and 2G12, wherein a carboxylic group or an amine group in the F_c region of the antibody is optionally bound to P₁ through a peptide bond; and
cyanovirin-N(SEQ ID NO:3), wherein a free amino group or carboxylate group of cyanovirin-N is optionally bound to P₁ through a peptide bond;
wherein P₁ is a chemical moiety, wherein P₁ comprises at least one thiol group;
wherein the nanoparticle is complexed to the binding molecule through a thiol group in the binding molecule.

In one embodiment, P₁ comprises at least one cysteine residue. In another embodiment, P₁ is βA Gln βA Cys-NH₂, wherein βA is beta-alanine. In yet another embodiment, the peptide of formula (I) is the compound of formula (II) or a salt thereof:

(II),                                    (SEQ ID NO: 2)
Arg Ile Asn Asn Ile X Trp Ser Glu Ala Met Met βA
Gln βA Cys-NH₂, wherein βA is beta-alanine. In yet another embodiment, the at least one nanoparticle has an average diameter of about 20 nm.

The invention further includes a method of promoting virolysis of a virus in a mammal. The method comprises administering to the mammal a therapeutically effective amount of a composition comprising at least one pharmaceutically acceptable carrier and at least one gold nanoparticle, wherein the gold nanoparticle is complexed with a binding molecule or a salt thereof. The binding molecule is selected from the group consisting of:

a peptide of formula (I) or a salt thereof:

(I),                                    (SEQ ID NO: 1-P₁)
Arg Ile Asn Asn Ile X Trp Ser Glu Ala Met Met-P₁, wherein X is (2,4)-4-(4-ferrocenyl-1H-1,2,3-triazol-1-yl) pyrrolidine-2-carboxylic acid, and
P₁ is linked to Arg Ile Asn Asn Ile X Trp Ser Glu Ala Met Met through a peptide bond;
a compound of formula P₂—P₁, wherein P₂ is selected from the group consisting of:

the compound of formula (III) [N-(4-chlorophenyl)-N'-(2,2,6,6-tetramethyl-piperidin-4-yl)-oxalamide]:

(III)

the compound of formula (IV) [N-(4-bromophenyl)-N'-(2,2,6,6-tetramethyl-piperidin-4-yl)-oxalamide]:

(IV)

and the compound of formula (V) [(R)-1-(4-benzoyl-2-methylpiperazin-1-yl)-2-(4-methoxy-1H-pyrrolo-[2,3-b]pyridin-3-yl)ethane-1,2-dione]:

(V)

[Chemical structure of formula (V)]

wherein the NH group of the piperidinyl group in (III) or (IV), or the N¹H group of the indole group in (V) is bound to P$_1$ through a peptide bond;

an anti-HIV-1-gp120 antibody selected from the group consisting of 17b, F105 and 2G12, wherein a carboxylic group or an amine group in the F$_c$ region of the antibody is optionally bound to P$_1$ through a peptide bond; and cyanovirin-N(SEQ ID NO:3), wherein a free amino group or carboxylate group of cyanovirin-N is optionally bound to P$_1$ through a peptide bond;

wherein P$_1$ is a chemical moiety, wherein P$_1$ comprises at least one thiol group;

wherein the nanoparticle is complexed to the binding molecule through a thiol group in the binding molecule;

whereby virolysis of the virus in the mammal is promoted.

The invention also includes a method of reducing the rate of or preventing entry of a virus into a cell of a mammal. The method comprises administering to the mammal a therapeutically effective amount of a composition comprising at least one pharmaceutically acceptable carrier and at least one gold nanoparticle, wherein the gold nanoparticle is complexed with a binding molecule or a salt thereof. The binding molecule is selected from the group consisting of:

a peptide of formula (I) or a salt thereof:

(I), (SEQ ID NO: 1-P$_1$)
Arg Ile Asn Asn Ile X Trp Ser Glu Ala Met Met-P$_1$, wherein X is (2,4)-4-(4-ferrocenyl-1H-1,2,3-triazol-1-yl)pyrrolidine-2-carboxylic acid, and P$_1$ is linked to Arg Ile Asn Asn Ile X Trp Ser Glu Ala Met Met through a peptide bond;

a compound of formula P$_2$—P$_1$, wherein P$_2$ is selected from the group consisting of:

the compound of formula (III) [N-(4-chlorophenyl)-N'-(2,2,6,6-tetramethyl-piperidin-4-yl)-oxalamide]:

(III)

[Chemical structure of formula (III)]

the compound of formula (IV) [N-(4-bromophenyl)-N'-(2,2,6,6-tetramethyl-piperidin-4-yl)-oxalamide]:

(IV)

[Chemical structure of formula (IV)]

and the compound of formula (V) [(R)-1-(4-benzoyl-2-methylpiperazin-1-yl)-2-(4-methoxy-1H-pyrrolo-[2,3-b]pyridin-3-yl)ethane-1,2-dione]:

(V)

[Chemical structure of formula (V)]

wherein the NH group of the piperidinyl group in (III) or (IV), or the N¹H group of the indole group in (V) is bound to P$_1$ through a peptide bond;

an anti-HIV-1-gp120 antibody selected from the group consisting of 17b, F105 and 2G12, wherein a carboxylic group or an amine group in the F$_c$ region of the antibody is optionally bound to P$_1$ through a peptide bond; and cyanovirin-N(SEQ ID NO:3), wherein a free amino group or carboxylate group is optionally bound to P$_1$ through a peptide bond;

wherein P$_1$ is a chemical moiety, wherein P$_1$ comprises at least one thiol group;

wherein the nanoparticle is complexed to the binding molecule through a thiol group in the binding molecule;

whereby the entry of the virus into the cell of the mammal is prevented or takes place at a reduced rate as compared to an untreated mammal.

The method further includes a method of preventing, reducing or treating infection of a virus in a mammal. The method comprises administering to the mammal a therapeutically effective amount of a composition comprising at least one pharmaceutically acceptable carrier and at least one gold nanoparticle, wherein the gold nanoparticle is complexed with a binding molecule or a salt thereof. The binding molecule is selected from the group consisting of:

a peptide of formula (I) or a salt thereof:

(I), (SEQ ID NO: 1-P$_1$)
Arg Ile Asn Asn Ile X Trp Ser Glu Ala Met Met-P$_1$, wherein X is (2,4)-4-(4-ferrocenyl-1H-1,2,3-triazol-1-yl)pyrrolidine-2-carboxylic acid, and P$_1$ is linked to Arg Ile Asn Asn Ile X Trp Ser Glu Ala Met Met through a peptide bond;

a compound of formula P$_2$—P$_1$, wherein P$_2$ is selected from the group consisting of:

the compound of formula (III) [N-(4-chlorophenyl)-N'-(2,2,6,6-tetramethyl-piperidin-4-yl)-oxalamide]:

(III)

the compound of formula (IV) [N-(4-bromophenyl)-N'-(2,2,6,6-tetramethyl-piperidin-4-yl)-oxalamide]:

(IV)

and the compound of formula (V) [(R)-1-(4-benzoyl-2-methylpiperazin-1-yl)-2-(4-methoxy-1H-pyrrolo-[2,3-b]pyridin-3-yl)ethane-1,2-dione]:

(V)

wherein the NH group of the piperidinyl group in (III) or (IV), or the N$^1$H group of the indole group in (V) is bound to P$_1$ through a peptide bond;
an anti-HIV-1-gp120 antibody selected from the group consisting of 17b, F105 and 2G12, wherein a carboxylic group or an amine group in the F$_c$ region of the antibody is optionally bound to P$_1$ through a peptide bond; and
cyanovirin-N(SEQ ID NO:3), wherein a free amino group or carboxylate group of cyanovirin is optionally bound to P$_1$ through a peptide bond;
wherein P$_1$ is a chemical moiety, wherein P$_1$ comprises at least one thiol group;
wherein the nanoparticle is complexed to the binding molecule through a thiol group in the binding molecule;
whereby the infection of the virus in the mammal is prevented, reduced or treated.

In one embodiment, the virus is HIV-1, influenza, ebola or dengue. In another embodiment, the virus is HIV-1. In yet another embodiment, P$_1$ comprises at least one cysteine residue. In yet another embodiment, P$_1$ is βA Gln βA Cys-NH$_2$, wherein βA is beta-alanine. In yet another embodiment, the peptide of formula (I) is the compound of formula (II) or a salt thereof:

(II), (SEQ ID NO: 2)
Arg Ile Asn Asn Ile X Trp Ser Glu Ala Met Met βA Gln βA Cys-NH$_2$, wherein βA is beta-alanine. In yet another embodiment, the at least one nanoparticle has an average diameter of about 20 nm. In yet another embodiment, the mammal is further administered at least one additional compound useful for treating viral infections. In yet another embodiment, the at least one additional compound is selected from the group consisting of antiviral combination drugs, entry and fusion inhibitors, integrase inhibitors, non-nucleoside reverse transcriptase inhibitors, nucleoside reverse transcriptase inhibitors, protease inhibitors, and combinations thereof. In yet another embodiment, the at least one additional compound and the peptide are co-formulated. In yet another embodiment, the peptide is encapsulated in a hydrogel. In yet another embodiment, the hydrogel is pH-responsive. In yet another embodiment, the hydrogel comprises a polymerized mixture of methacrylic acid and PEG-monomethyl ether monomethacrylate. In yet another embodiment, the composition is administered orally, nasally, rectally, intravaginally, parenterally, buccally, sublingually, intragastrically or topically to the mammal. In yet another embodiment, the mammal is human.

The invention also includes a method of promoting virolysis of a virus in a mammal. The method comprises administering to the mammal a therapeutically effective amount of a composition comprising at least one pharmaceutically acceptable carrier and a peptide of formula (I) or a salt thereof:

(I), (SEQ ID NO: 1-P$_1$)
Arg Ile Asn Asn Ile X Trp Ser Glu Ala Met Met-P$_1$, wherein X is (2,4)-4-(4-ferrocenyl-1H-1,2,3-triazol-1-yl)pyrrolidine-2-carboxylic acid, and P$_1$ is linked to Arg Ile Asn Asn Ile X Trp Ser Glu Ala Met Met through a peptide bond; wherein P$_1$ is a chemical moiety, wherein P$_1$ comprises at least one thiol group; whereby virolysis of the virus in the mammal is promoted.

The invention further includes a method of reducing the rate of or preventing entry of a virus into a cell of a mammal. The method comprises administering to the mammal a therapeutically effective amount of a composition comprising at least one pharmaceutically acceptable carrier and a peptide of formula (I) or a salt thereof:

(I), (SEQ ID NO: 1-P$_1$)
Arg Ile Asn Asn Ile X Trp Ser Glu Ala Met Met-P$_1$, wherein X is (2,4)-4-(4-ferrocenyl-1H-1,2,3-triazol-1-yl)pyrrolidine-2-carboxylic acid, and P$_1$ is linked to Arg Ile Asn Asn Ile X Trp Ser Glu Ala Met Met through a peptide bond; wherein P$_1$ is a chemical moiety, wherein P$_1$ comprises at least one thiol group; whereby the entry of the virus into the cell of the mammal is prevented or takes place at a reduced rate as compared to an untreated mammal.

The invention also includes a method of preventing, reducing or treating infection of a virus in a mammal. The method comprises administering to the mammal a therapeutically effective amount of a composition comprising at least one pharmaceutically acceptable carrier and a peptide of formula (I) or a salt thereof:

(I),                                                    (SEQ ID NO: 1-P₁)
Arg Ile Asn Asn Ile X Trp Ser Glu Ala Met Met-P₁, wherein X is (2,4)-4-(4-ferrocenyl-1H-1,2,3-triazol-1-yl) pyrrolidine-2-carboxylic acid, and $P_1$ is linked to Arg Ile Asn Asn Ile X Trp Ser Glu Ala Met Met through a peptide bond; wherein $P_1$ is a chemical moiety, wherein $P_1$ comprises at least one thiol group; whereby the infection of the virus in the mammal is prevented, reduced or treated.

BRIEF DESCRIPTION OF THE DRAWINGS

FIG. 1 is a schematic illustration of a non-limiting methodology of the invention.

FIG. 12A: KR13 primary structure. FIG. 12B: SPR sensograms of direct binding of KR13 to immobilized gp120. Sensogram gray tones are darker with increasing analyte concentrations; $K_d$ value from steady-state analysis is 11.3 nm, obtained from the steady-state fit. FIG. 12C: ELISA-derived competition plots for 17b (○; $IC_{50}$=45.3±1.2 nm) and CD4 (■; $IC_{50}$=25±4.2 nm) binding to plate-immobilized gp120. FIG. 12D: Scheme of the AuNP-KR13 conjugate synthesized using thiol linkage; size of AuNP-KR13 measured using DLS (n=3). FIG. 12E: Transmission electron microscopy (TEM) image of AuNP-KR13.

FIG. 13A: Inhibition of infection of HOS.T4.R5 cells by recombinant viruses pseudotyped with the envelope for HIV-$1_{BaL}$ (solid) or with the envelope for VSV-G (open). The data were normalized to 100% infection activity at 0 nM concentration of KR13. The calculated $IC_{50}$ value of KR13 alone was 23±6 nM, n=4; that of the AuNP-KR13 conjugate was 1±0.1 nM, n=3. Efficacy parameters were calculated using sigmoidal logistic fit in Origin Pro 8 software. FIG. 13B: Cell toxicity assay on AuNP-KR13 (■) and KR13 (●) using WST-1 reagent; no statistically significant differences measured, P<0.05, n=3 using a t-test.

FIG. 14C: Dose-response plots of band intensities of the relative release percentage of p24 compared to the lysed virus control for both KR13 alone (●) and AuNP-KR13 (■).

FIG. 15A: DLS measurements of the produced AuNPs (Malvern Instruments-Zetasizer NS90), illustrating that the concentration of citric acid and the size of the particles have a linear dependency. FIG. 15B: DLS measurement for the 20 nm AuNP particles in comparison to the AuNP-KR13 conjugate showing a 2 nm shift in diameter.

FIG. 16C: p24 release profile of pseudovirus with VSV-G envelope in the presence of KR13 and AuNP-KR13 as a function of dose. Controls shown were lysed virus (treated with 1% Triton X-100) intact virus (no treatments) and p24 control (5 μL of 20 μg/ml).

FIGS. 18A-18C illustrate size-dependent measurements. FIG. 18A: Size dependent inhibition of infection of HOS.T4.R5 cells by recombinant viruses pseudotyped with the envelope for HIV-$1_{BaL}$ with differing diameter AuNP-KR13. Data were normalized to 100% infection activity without KR13. FIG. 18B: Size dependent release of p24 from recombinant viruses pseudotyped with the envelope for HIV-$1_{BaL}$ with differing diameter AuNP-KR13. Data were normalized to 100% lysed virus using 1% Triton-X. FIG. 18C: Plot (n=3) of $IC_{50}$s and $EC_{50}$s against AuNP-KR13 diameters with Farazdaghi-Harris and Parabola Model fits.

FIG. 20A: Inhibition of HIV-$1_{BaL}$ pseudotyped virus demonstrating decrease in viral inhibition with PEG tether. FIG. 20B: p24

Figures 20A, 20B:
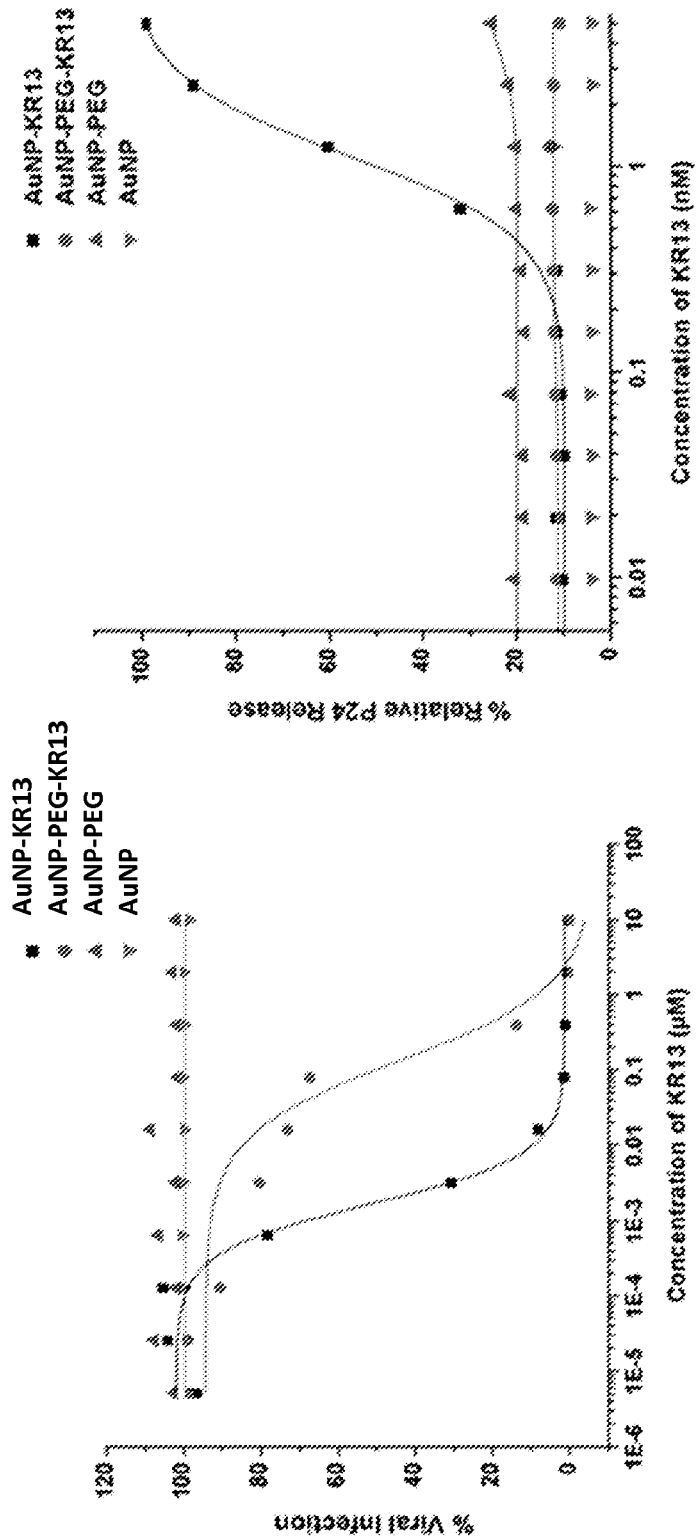
FIGS. 20A-20D illustrate the effect of flexible PEG tether (MW=5000 Da) between AuNP and KR13.
Figure 20D:
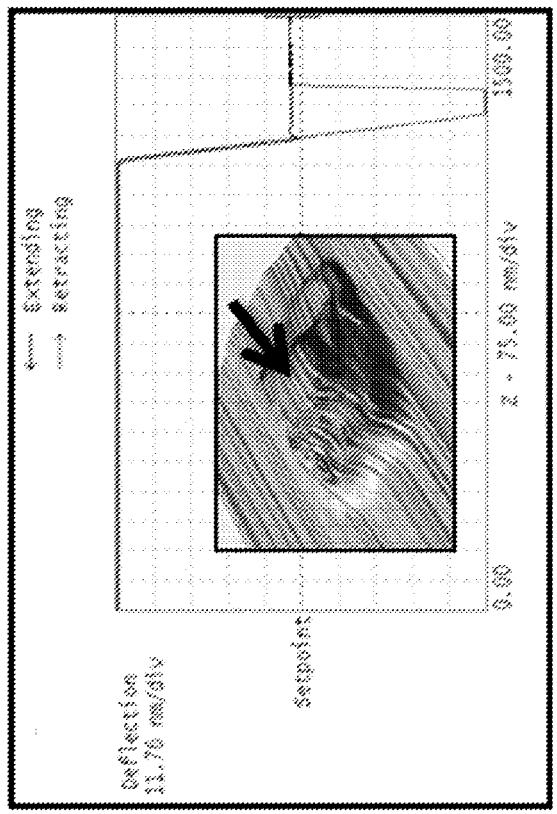
Figure 20C:
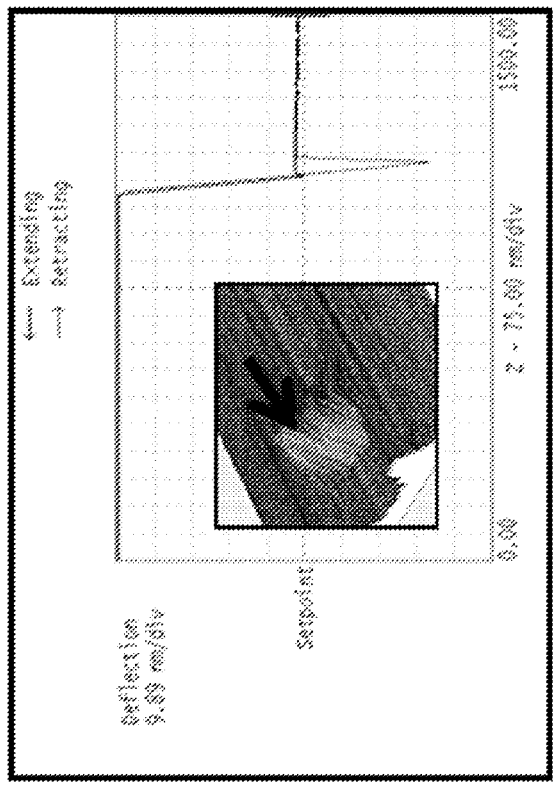

Release for AuNP-KR13 versus AuNP-PEG5000-KR13. Single point deformations on (FIG. 20C) AuNP and (FIG. 20D) AuNP-PEG are depicted with AFM micrograph insets. Arrows depict point at which loading occurred.

Figure 21:
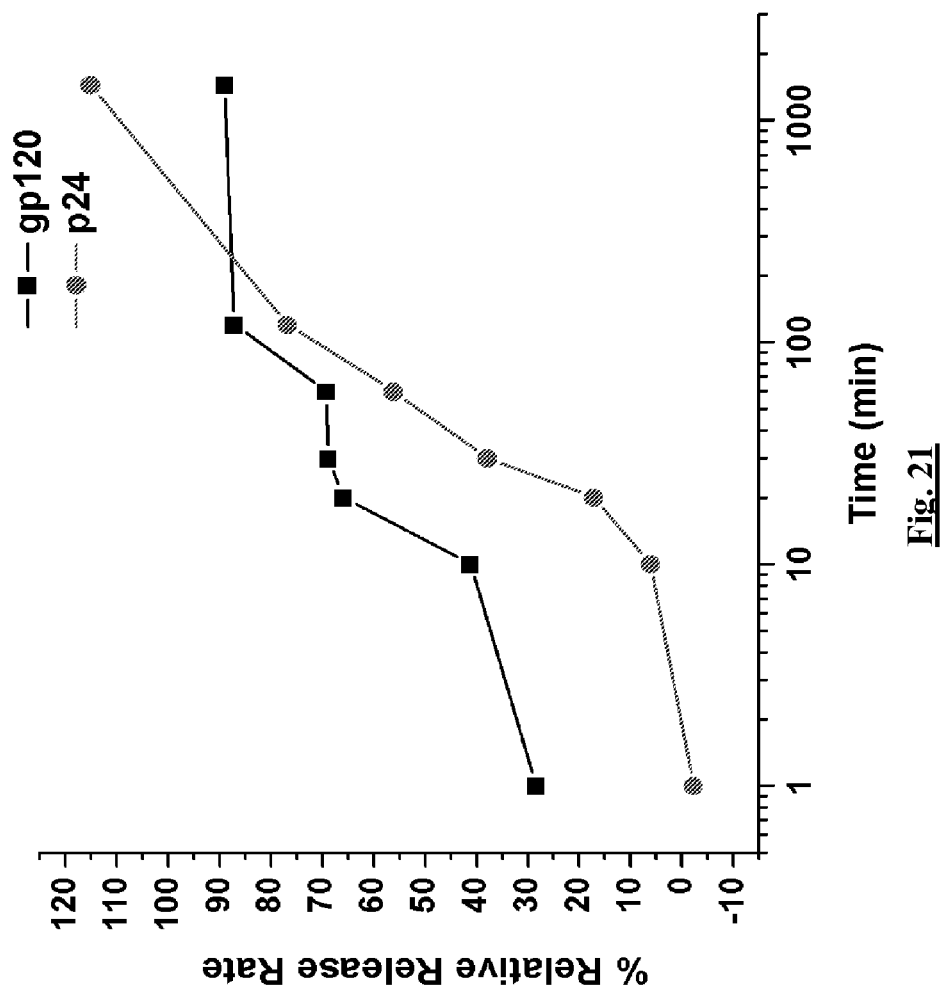

FIG. 21 is a graph illustrating that the ELISA assay of gp120 and p24 demonstrates a time dependent release when treated with AuNP-KR13 (diameter of 20 nm). All data were reported as percentage of total protein that was disrupted from virus using 1% Triton X.

FIGS. 22A-22D illustrate TEM analysis of viral morphology in the presence of AuNP-KR13. FIG. 22A and FIG. 22B illustrate representative cryo-TEM slices through a tomogram of HIV-1 BaL. Images in FIG. 22A and FIG. 22B were at the same scale. Scale bar: 50 nm. FIG. 22C and FIG. 22D illustrate representative TEM images from the lab stock of intact HIV-1 BAL pseudotyped virus in absence (FIG. 22C) and in the presence (FIG. 22D) of 20 nm AUNP-KR13. Statistical analysis was conducted on all the above. All samples used 100 nM of 20 nm AuNP-KR13 conjugates.

FIGS. 23A-23B illustrate hydrogel release of encapsulated AuNPs. FIG. 23A: Picture of hydrogels in 50 mM NaPOH$_4$ buffers of pH 3, 7 and 11 after 24 hours. FIG. 23B: Calculated percentage of AuNPs released into the buffered solution as determined by UV/Vis absorbance at 450 nm.

DETAILED DESCRIPTION OF THE INVENTION

The present invention relates to the unexpected discovery of novel gp-120-targeting triazole-peptide antagonists, which inhibit binding to both CD4 and co-receptor binding sites. The present invention further relates to a composition comprising gold nanoparticles to which the novel antagonists are attached. The present invention also related to a composition comprising gold nanoparticles to which a viral envelope protein binder is attached, wherein the binder is a small molecule, protein or antibody. The present invention further relates to a novel method of preparing compositions comprising gold nanoparticles with narrow particle size distribution, wherein the nanoparticles are conjugated to a thiol terminated compound selected from the group consisting of a peptide-triazole entry inhibitor and a viral envelope protein binder, wherein the binder is a small molecule, protein or antibody. In one non-limiting embodiment, the method of the invention allows for the synthesis of particles with a size distribution as narrow as ±4 nm.

This is the first report of the preparation and characterization of the nanoparticle-antagonist compositions of the invention. The pairing of these components allows for the preparation of a peptide-based inhibitor with significantly increased potency in blocking viral entry into CD4+CCR5+ cells (without toxicity) and destabilizing the HIV-1 envelope trimer. In a non-limiting aspect, potency enhancement of the peptide, small molecule compound or antibody is achieved by multivalent conjugation of the peptide, small molecule compound or antibody to the AuNPs.

As reported herein, the compositions of the invention demonstrated not only enhancement of antiviral activity in cell infection assays, but also the striking ability of disrupting the viral particles in the absence of cells. This unexpected finding has significant implications for both prevention and therapeutic treatment of viral infection, and in particular HIV-1 infection. Taken altogether, the results reported herein indicate that peptide-Au conjugates are useful as viral entry inhibitors.

DEFINITIONS

As used herein, each of the following terms has the meaning associated with it in this section.

Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, and organic chemistry are those well-known and commonly employed in the art.

As used herein, the articles "a" and "an" refer to one or to more than one (i.e. to at least one) of the grammatical object of the article. By way of example, "an element" means one element or more than one element.

As used herein, the term "about" is understood by persons of ordinary skill in the art and varies to some extent on the context in which it is used. As used herein when referring to a measurable value such as an amount, a temporal duration and the like, the term "about" is meant to encompass variations of ±20%, more preferably ±10%, more preferably ±5%, even more preferably ±1%, and still more preferably ±0.1% from the specified value, as such variations are appropriate to perform the disclosed methods.

As used herein, the term "HBTU" refers to O-benzotriazole-N,N,N',N'-tetramethyl-uronium-hexafluoro-phosphate As used herein, the term "HOBt" refers to 1-hydroxybenzotriazole.

As used herein, the term "DMF" refers to N,N-dimethylformamide.

As used herein, the term "DIPEA" refers to N,N-diisopropyl-ethylamine.

As used herein, the term "PT" refers to peptide triazole.

As used herein, the term "NP" refers to nanoparticle.

As used herein, the term "NBD-556" refers to N-(4-chlorophenyl)-N'-(2,2,6,6-tetramethyl-piperidin-4-yl)-oxalamide or a salt thereof.

As used herein, the term "NBD-557" refers to N-(4-bromophenyl)-N'-(2,2,6,6-tetramethyl-piperidin-4-yl)-oxalamide or a salt thereof.

As used herein the term "BMS-806' refers to (R)-1-(4-benzoyl-2-methylpiperazin-1-yl)-2-(4-methoxy-1H-pyrrolo[2,3-b]pyridin-3-yl)ethane-1,2-dione or a salt thereof.

As used herein, the terms "peptide," "polypeptide," or "protein" are used interchangeably, and refer to a compound comprised of amino acid residues covalently linked by peptide bonds. A protein or peptide must contain at least two amino acids, and no limitation is placed on the maximum number of amino acids that can comprise the sequence of a protein or peptide. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs and fusion proteins, among others. The polypeptides include natural peptides, recombinant peptides, synthetic peptides or a combination thereof. A peptide that is not cyclic has a N-terminus and a C-terminus. The N-terminus has an amino group, which may be free (i.e., as a NH$_2$ group) or appropriately protected (e.g., with a BOC or a Fmoc group). The C-terminus has a carboxylic group, which may be free (i.e., as a COOH group) or appropriately protected (e.g., as a benzyl or a methyl ester). A cyclic peptide does not necessarily have free N- or C-termini, since they are covalently bonded through an amide bond to form the cyclic structure.

As used herein, "natural amino acids" are represented by the full name thereof, by the three-letter code, as well as the one-letter code corresponding thereto, as indicated in the following table. The structure of amino acids and their abbreviations can also be found in the chemical literature, such as in Stryer, 1988, "Biochemistry", $3^{rd}$ Ed., W. H. Freeman and Co., New York.

| Full Name | Three-Letter Code | One-Letter Code |
|---|---|---|
| Alanine | Ala | A |
| Arginine | Arg | R |
| Asparagine | Asn | N |
| Aspartic Acid | Asp | D |
| Cysteine | Cys | C |
| Cystine | Cys-Cys | C-C |
| Glutamic Acid | Glu | E |
| Glutamine | Gln | Q |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

As used herein, the term "non-natural amino acid" corresponds to an amino acid that is not the L-isomer of one of the natural alpha-amino acids listed herein. Non-natural amino acids include, but are not limited to, the D-isomer of a natural amino acid, $H_2N$—$(CH_2CH_2O)_n$—$CH_2CH_2$—COOH (wherein MW varies from ~1000 Da to 10000 Da), $H_2N$—$(CH_2)_n$—COOH (wherein n is an integer that varies from 3 to 8), arginosuccinic acid, citrulline, cysteine sulfinic acid, 3,4-dihydroxy-phenylalanine, homocysteine, homoserine, ornithine, hydroxylysine, 4-hydroxy-proline, an N-Cbz-protected amino acid, 2,4-diaminobutyric acid, homoarginine, N-methyl-arginine, norleucine, N-methylaminobutyric acid, naphthylalanine, phenylglycine, beta-phenylproline, tert-leucine, 4-aminocyclohexyl-alanine, N-methyl-norleucine, 3,4-dehydroproline, N,N-dimethylaminoglycine, N-methylaminoglycine, 4-aminopiperidine-4-carboxylic acid, 6-aminocaproic acid (also known as Acp or 6-aminohexanoic acid), 6-aminocapramide (also known as $AcpNH_2$ or 6-aminohexanamide), beta-alanine (also known as bAla or βAla), $bAlaNH_2$ (or $βAlaNH_2$, and also known as 3-aminopropanamide), trans-4-(aminomethyl)-cyclohexanecarboxylic acid, 2-(aminomethyl)-benzoic acid, 3-(aminomethyl)-benzoic acid, 4-(aminomethyl)-benzoic acid, 1-aminocyclopentanecarboxylic acid, 1-aminocyclopropanecarboxylic acid, and 2-benzyl-5-aminopentanoic acid. Preferentially, the non-natural amino acid is selected from the group consisting of Acp, $AcpNH_2$, bAla and $bAlaNH_2$.

The term "antibody," as used herein, refers to an immunoglobulin molecule able to specifically bind to a specific epitope on an antigen. Antibodies can be intact immunoglobulins derived from natural sources or from recombinant sources and can be immunoreactive portions of intact immunoglobulins. Antibodies are typically tetramers of immunoglobulin molecules. The antibodies in the present invention may exist in a variety of forms including, for example, polyclonal antibodies, monoclonal antibodies, intracellular antibodies ("intrabodies"), Fv, Fab and $F(ab)_2$, as well as single chain antibodies (scFv) and humanized antibodies (Harlow et al., 1998, Using Antibodies: A Laboratory Manual, Cold Spring Harbor Laboratory Press, NY; Harlow et al., 1989, Antibodies: A Laboratory Manual, Cold Spring Harbor, N.Y.; Houston et al., 1988, Proc. Natl. Acad. Sci. USA 85:5879-5883; Bird et al., 1988, Science 242:423-426). As used herein, a "neutralizing antibody" is an immunoglobulin molecule that binds to and blocks, directly or indirectly, the biological activity of the antigen.

As used herein, the term "immunoglobulin" or "Ig" is defined as a class of proteins that function as antibodies. The five members included in this class of proteins are IgA, IgG, IgM, IgD, and IgE. IgA is the primary antibody that is present in body secretions, such as saliva, tears, breast milk, gastrointestinal secretions and mucus secretions of the respiratory and genitor-urinary tracts. IgG is the most common circulating antibody. IgM is the main immunoglobulin produced in the primary immune response in most mammals. It is the most efficient immunoglobulin in agglutination, complement fixation, and other antibody responses, and is important in defense against bacteria and viruses. IgD is the immunoglobulin that has no known antibody function, but may serve as an antigen receptor. IgE is the immunoglobulin that mediates immediate hypersensitivity by causing release of mediators from mast cells and basophils upon exposure to allergen.

The term "epitope" as used herein is defined as a small chemical molecule on an antigen that may elicit an immune response, inducing B and/or T cell responses. An antigen may have one or more epitopes. Most antigens have many epitopes; i.e., they are multivalent. In general, an epitope is roughly five amino acids and/or sugars in size. One skilled in the art understands that generally the overall three-dimensional structure, rather than the specific linear sequence of the molecule, is the main criterion of antigenic specificity and therefore distinguishes one epitope from another.

As used herein with respect to the compounds of the invention, "biologically active" means that the compounds elicit a biological response in a mammal that can be monitored and characterized in comparison with an untreated mammal. One possible biological response within the invention relates to the ability of the compound to avoid, reduce or treat HIV-1 infection in a mammal. In this particular case, the compound is administered to the mammal orally, nasally, rectally, intravaginally, parenterally, buccally, sublingually, intragastrically or topically. The mammal and the HIV-1 viral load level in its body are monitored as a function of time, and the observation of a measurable and dose-dependent change in HIV-1 infection rate or viral load in the body is evidence that the compound displays biological activity. This preferred biological response does not limit or restrict the disclosures or embodiments of the invention in any way.

As used herein, the term "viral envelope protein binder" refers to a small molecule, peptide or antibody that binds to at least one envelope protein of a virus.

As used herein, the term "gp120 binder" refers to a small molecule, peptide or antibody that binds to the envelope protein gp120 of HIV-1.

As used herein, the term "antiviral agent" means a composition of matter that, when delivered to a cell, is capable of preventing replication of a virus in the cell, preventing infection of the cell by a virus, or reversing a physiological effect of infection of the cell by a virus. Antiviral agents are well known and described in the literature. By way of example, AZT (zidovudine, Retrovir®, Glaxosmithkline, Middlesex, UK) is an antiviral agent that is thought to prevent replication of HIV in human cells.

As used herein, the term "treating" means ameliorating the effects of, or delaying, halting or reversing the progress of a disease or disorder. The word encompasses reducing the severity of a symptom of a disease or disorder and/or the frequency of a symptom of a disease or disorder.

As used herein, the term "medical intervention" means a set of one or more medical procedures or treatments that are required for ameliorating the effects of, delaying, halting or reversing a disease or disorder of a subject. A medical intervention may involve surgical procedures or not, depending on the disease or disorder in question. A medical intervention may be wholly or partially performed by a medical specialist, or may be wholly or partially performed by the subject himself or herself, if capable, under the supervision of a medical specialist or according to literature or protocols provided by the medical specialist.

As used herein, a "subject" or a "mammal" includes a human or a non-human mammal. Non-human mammals include, for example, livestock and pets, such as ovine, bovine, porcine, canine, feline and murine mammals. Preferably, the subject or mammal is human.

As used herein, the language "effective amount" or "therapeutically effective amount" refers to a non-toxic but sufficient amount of the composition used in the practice of the invention that is effective to treat, prevent or ameliorate HIV-1 infection in the body of a mammal. The desired treatment may be prophylactic and/or therapeutic. That result may be reduction and/or alleviation of the signs, symptoms, or causes of a disease or disorder, or any other desired alteration of a biological system. An appropriate therapeutic amount in any individual case may be determined by one of ordinary skill in the art using routine experimentation.

As used herein, a "prophylactic" or "preventive" treatment is a treatment administered to a subject who does not exhibit signs of a disease or disorder or exhibits only early signs of the disease or disorder for the purpose of decreasing the risk of developing pathology associated with the disease or disorder.

As used herein, a "therapeutic" treatment is a treatment administered to a subject who exhibits signs of pathology of a disease or disorder for the purpose of diminishing or eliminating those signs.

As used herein, a "pharmaceutically acceptable carrier" means a pharmaceutically acceptable material, composition or carrier, such as a liquid or solid filler, diluent, excipient, solvent or encapsulating material, involved in carrying or transporting a compound(s) of the present invention within or to the subject such that it may perform its intended function. Typically, such compounds are carried or transported from one organ, or portion of the body, to another organ, or portion of the body. Each carrier must be "acceptable" in the sense of being compatible with the other ingredients of the formulation, and not injurious to the patient. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; gar; buffering agents, such as magnesium hydroxide and aluminum hydroxide; alginic acid; pyrogen-free water; isotonic saline; Ringer's solution; ethyl alcohol; phosphate buffer solutions; diluent; granulating agent; lubricant; binder; disintegrating agent; wetting agent; emulsifier; coloring agent; release agent; coating agent; sweetening agent; flavoring agent; perfuming agent; preservative; antioxidant; plasticizer; gelling agent; thickener; hardener; setting agent; suspending agent; surfactant; humectant; carrier; stabilizer; and other non-toxic compatible substances employed in pharmaceutical formulations, or any combination thereof. As used herein, "pharmaceutically acceptable carrier" also includes any and all coatings, antibacterial and antifungal agents, and absorption delaying agents, and the like that are compatible with the activity of the compound, and are physiologically acceptable to the subject. Supplementary active compounds may also be incorporated into the compositions.

As used herein, the term "container" includes any receptacle for holding the pharmaceutical composition. For example, in one embodiment, the container is the packaging that contains the pharmaceutical composition. In other embodiments, the container is not the packaging that contains the pharmaceutical composition, i.e., the container is a receptacle, such as a box or vial that contains the packaged pharmaceutical composition or unpackaged pharmaceutical composition and the instructions for use of the pharmaceutical composition. Moreover, packaging techniques are well known in the art. It should be understood that the instructions for use of the pharmaceutical composition may be contained on the packaging containing the pharmaceutical composition, and as such the instructions form an increased functional relationship to the packaged product. However, it should be understood that the instructions can contain information pertaining to the compound's ability to perform its intended function, e.g., treating, ameliorating, or preventing shivering in a subject.

"Applicator," as the term is used herein, is used to identify any device including, but not limited to, a hypodermic syringe, a pipette, and the like, for administering the compounds and compositions used in the practice of the invention.

DESCRIPTION

The invention relates to a novel class of gp120-targeting triazole-peptide antagonists that inhibit both CD4 and co-receptor binding sites. The invention also relates to a novel composition comprising gold nanoparticles conjugated to the triazole-peptide antagonists. The invention further relates to a novel composition comprising gold nanoparticles conjugated to at least one viral envelope protein binder.

Figure 1:
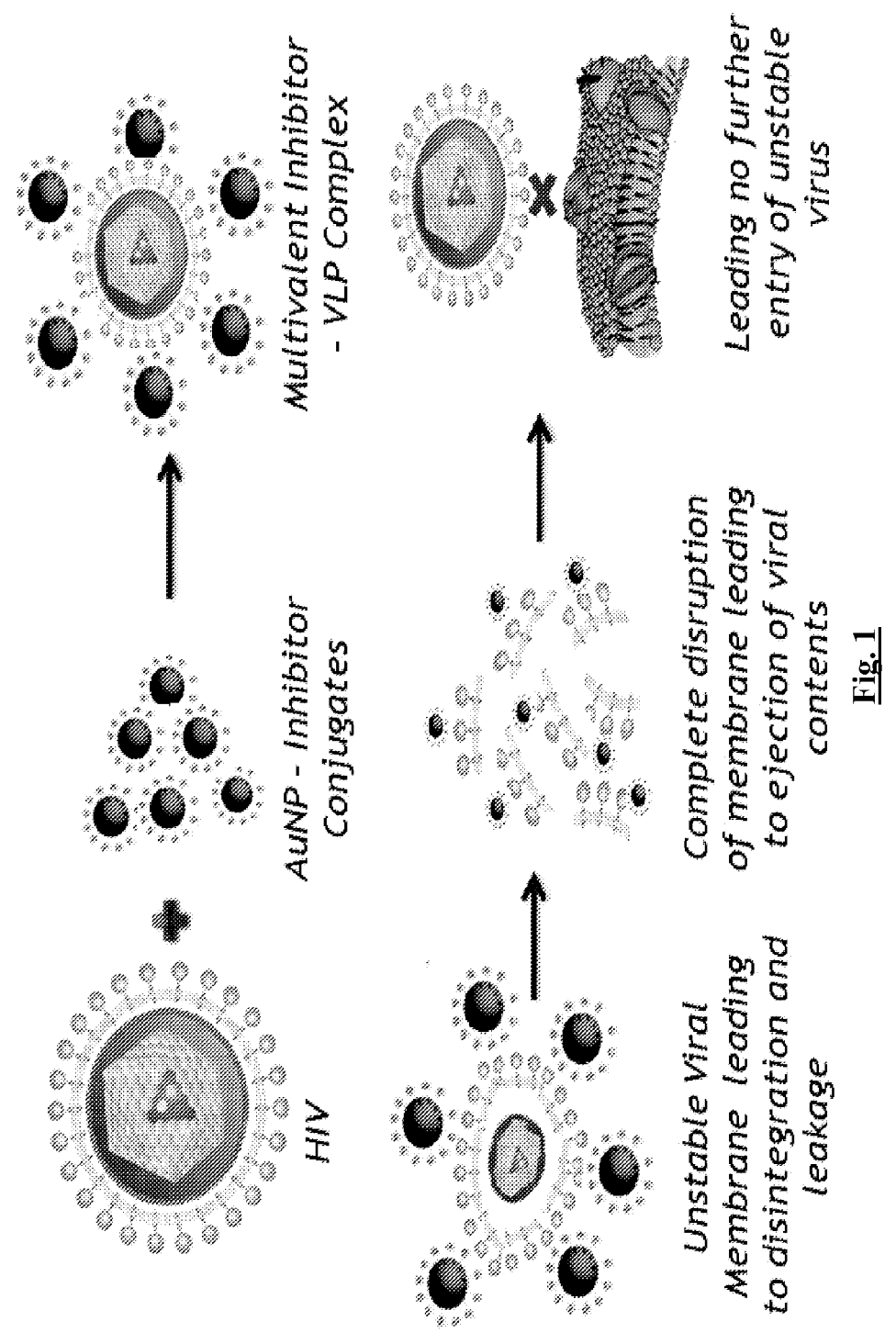

In a non-limiting aspect, the present work evaluated the antiviral activity of a modified HNG class of triazole-peptides containing a C-terminal cysteine, termed KR13, conjugated to gold nanoparticles (AuNPs). In the context of this disclosure, the terms "conjugated," "bound," "coordinated," or "complexed" are interchangeable. AuNPs (20 nm) were synthesized using a one-step aqueous method leading to particles with a narrow size distribution (±4 nm) as characterized using UV-Vis spectroscopy, dynamic light scattering (DLS) and transmission electron microscopy (TEM). The strong Au—S linkage allowed a highly multivalent conjugation of KR13 peptide to the AuNP with an estimated 85±5% coverage efficiency of the gold surface. Single-round viral cell infection assays were conducted in vitro using CD4-transfected human osteosarcoma cells and subtype B strain HIV-$1_{BaL}$ pseudovirus (CCR5 phenotype). These viral infection assays demonstrated that multivalent peptide-AuNP significantly improved the inhibition potency of the KR13 peptide alone. In addition, the conjugate was found to increase viral envelop shedding compared to peptide alone. WST-1 toxicity assays indicated that the conjugate had no toxic effects on the cultured cells when compared to unexposed controls. This work suggests that nanoparticle conjugation may increase the potency of a known gp120 antagonist in both inhibiting the virus-cell infection and inactivating the virus itself. The results also suggest the potential value of AuNP-peptide triazoles as microbicidal and therapeutic agents. Further optimization of multivalent peptide triazole-AuNPs may improve inhibitor potency, peptide stability and tissue targeting. In one aspect, the methodology disclosed herein is illustrated in FIG. 1.

Compositions of the Invention

The invention includes a composition comprising a peptide of formula (I) or a salt thereof:

(I), (SEQ ID NO: 1-$P_1$)
Arg Ile Asn Asn Ile X Trp Ser Glu Ala Met Met-$P_1$, wherein X is (2,4)-4-(4-ferrocenyl-1H-1,2,3-triazol-1-yl) pyrrolidine-2-carboxylic acid, and $P_1$ is a chemical moiety, wherein:

$P_1$ is linked to Arg Ile Asn Asn Ile X Tip Ser Glu Ala Met Met through a peptide bond, and $P_1$ comprises at least one thiol group.

In one embodiment, $P_1$ comprises at least one cysteine residue. In another embodiment, $P_1$ comprises at least one natural or unnatural amino acid. In yet another embodiment, $P_1$ is a peptide consisting of at least two natural or unnatural amino acids. In yet another embodiment, $P_1$ is βA Gln βA Cys-$NH_2$, wherein βA is beta-alanine. In yet another embodiment, the peptide of formula (I) is the compound of formula (II) or a salt thereof:

(II), (SEQ ID NO: 2)
Arg Ile Asn Asn Ile X Trp Ser Glu Ala Met Met βA Gln βA Cys-$NH_2$, wherein βA is beta-alanine In one embodiment, the composition further comprises at least one gold nanoparticle, wherein the at least one nanoparticle is complexed to the peptide of formula (I) through the at least one thiol group.

The invention also includes a composition comprising at least one gold nanoparticle, wherein the at least one nanoparticle is complexed to a binding molecule, or a salt thereof, selected from the group consisting of:

a peptide of formula (I) or a salt thereof:

(I), (SEQ ID NO: 1-$P_1$)
Arg Ile Asn Asn Ile X Trp Ser Glu Ala Met Met-$P_1$, wherein X is (2,4)-4-(4-ferrocenyl-1H-1,2,3-triazol-1-yl) pyrrolidine-2-carboxylic acid, and $P_1$ is linked to Arg Ile Asn Asn Ile X Trp Ser Glu Ala Met Met through a peptide bond;

a compound of formula $P_2$—$P_1$, wherein $P_2$ is selected from the group consisting of:

the compound of formula (III) [N-(4-chlorophenyl)-N'-(2, 2,6,6-tetramethyl-piperidin-4-yl)-oxalamide]:

(III)

the compound of formula (IV) [N-(4-bromophenyl)-N'-(2, 2,6,6-tetramethyl-piperidin-4-yl)-oxalamide]:

(IV)

and the compound of formula (V) [(R)-1-(4-benzoyl-2-methylpiperazin-1-yl)-2-(4-methoxy-1H-pyrrolo-[2,3-b]pyridin-3-yl)ethane-1,2-dione]:

(V)

wherein the NH group of the piperidinyl group in (III) or (IV), or the $N^1H$ group of the indole group in (V) is bound to $P_1$ through a peptide bond;

an anti-HIV-1-gp120 antibody selected from the group consisting of 17b, F105 and 2G12, wherein a carboxylic group or an amine group in the $F_c$ region of the antibody is optionally bound to $P_1$ through a peptide bond; and cyanovirin-N(SEQ ID NO:3), wherein a free amino group or carboxylate group is optionally bound to $P_1$ through a peptide bond;

wherein $P_1$ is a chemical moiety, wherein $P_1$ comprises at least one thiol group.

In one embodiment, the at least one nanoparticle has an average diameter of about 20 nm. In another embodiment, the composition further comprises at least one pharmaceutically acceptable carrier. In yet another embodiment, the composition further comprises at least one additional compound useful for treating viral infections. In yet another embodiment, the at least one additional compound is selected from the group consisting of antiviral combination drugs, entry and fusion inhibitors, integrase inhibitors, non-nucleoside reverse transcriptase inhibitors, nucleoside reverse transcriptase inhibitors, protease inhibitors, and combinations thereof. In yet another embodiment, the peptide is encapsulated in a hydrogel. In yet another embodiment, the hydrogel is pH-responsive. In yet another embodiment, the hydrogel comprises a polymerized mixture of methacrylic acid and PEG-monomethyl ether monomethacrylate.

The invention also includes a composition comprising a peptide relating to KR13, wherein one or more amino acid residues are replaced by one or more natural or non-natural amino acid residues of comparable polarity and hydrophobicity.

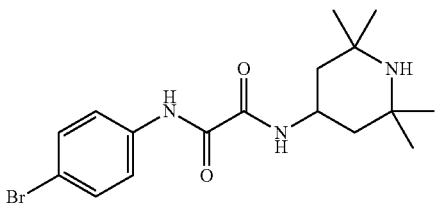

(IV)

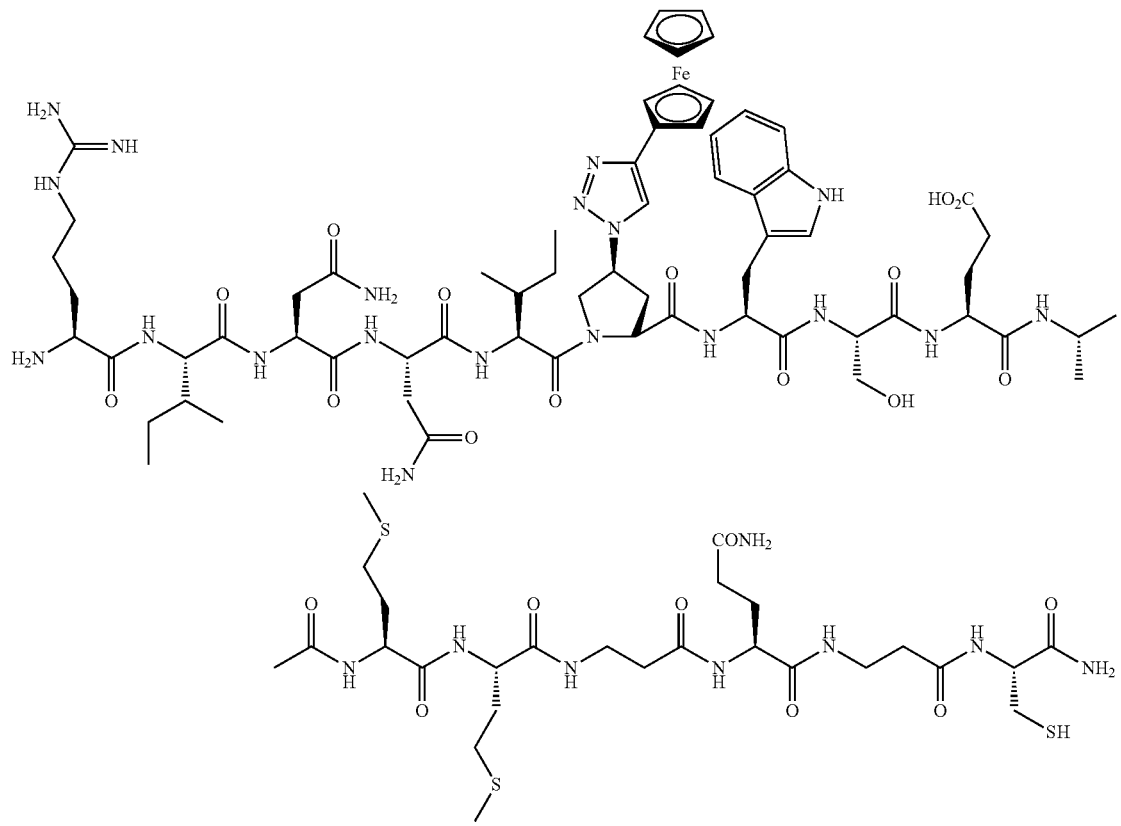

KR13

The compounds useful within the invention include N-4-chlorophenyl-N'-(2,2,6,6-tetramethyl-piperidin-4-yl)-oxalamide (III) and N-4-bromophenyl-N'-(2,2,6,6-tetramethyl-piperidin-4-yl)-oxalamide (IV), and analogs thereof.

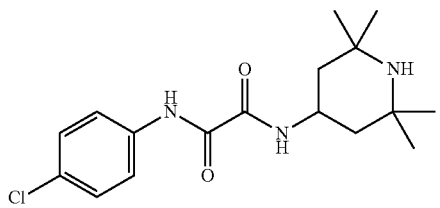

(III)

These compounds are a novel class of human immunodeficiency virus type 1 (HIV-1) entry inhibitors, blocking the gp120-CD4 interaction (Zhao et al., 2005, Virol. 339:213-225; Schön et al., 2006, Biochem. 45:10973-10980). In one aspect, these compounds may be conjugated to $P_1$ through a peptide bond between the NH group of the piperidine group on these compounds and a carboxylic group on $P_1$. The thiol group on $P_1$ may then be used to attach the conjugates to the gold nanoparticle.

The compounds useful within the invention include BMS-806 (V), also known as BMS-378806.

(V)

[Chemical structure of compound V]

BMS-806 was found to neutralize a broad panel of HIV-1 isolates with minimal cytotoxicity ($CC_{50}$>226 µM) (Lin et al., 2003, Proc. Natl. Acad. Sci. USA 100:11013-11018). The potential of BMS-806 to prevent infection was tested at the highest soluble concentration (5.5 mM) in macaques, with 6 of 8 animals remaining uninfected. No local irritation or inflammation was observed upon biopsy of the macaque vagina after multiple applications (Veazey et al., 2005, Nature 438:99-102). When macaques were challenged with virus 2-6 hours after application of BMS-806, 3 of 5 were protected.

Mechanistically, BMS-806 appears to inhibit viral entry by binding directly to gp120 (Guo et al., 2003, J. Virol. 77:10528-10536; Si et al., 2004, Proc. Natl. Acad. Sci. USA 101:5036-5041; Schön et al., 2006, Biochem. 45:10973-10980). Although there is some ambiguity about its mode of inhibition, BMS-806 appears to block early stages of HIV-1 entry by either preventing its interaction with CD4 (Lin et al., 2003, Proc. Natl. Acad. Sci. USA 100:11013-11018; Guo et al., 2003, J. Virol. 77:10528-10536) or preventing CD4-induced changes to gp120 that are necessary for the entry process to occur.

In one aspect, this compound may be conjugated to $P_1$ through a peptide bond between the $N^1H$ group of the indole group on (V) and a carboxylic group on $P_1$. The thiol group on $P_1$ may then be used to attach the conjugate to the gold nanoparticle. In case that an analog of BMS-806 lacking the indole ring is to be used within the methods of the invention, the piperazine ring of the analog may be chemically opened and the molecule may be coupled to $P_1$ through a peptide bond.

The antibodies useful within the invention include the anti-HIV-1-gp120 antibodies 17b, F105 and 2G12.

The 17b antibody binds to moderately well conserved conformation-dependent epitope of HIV-1 gp120. Binding of antibody is significantly enhanced when gp120 is bound to CD4. The antibody has neutralizing activity against several laboratory strains of HIV-1 and some primary isolates (Posner et al., 1993, J. Acquir. Immune Defic. Syndr. 6:7-14; Shuttner et al., 1993, AIDS 7:919-923; Sever et al., 1995, Pediatr. AIDS HIV Infect. 6:75-82; Trkola et al., 1996, Nature 384:184-187).

The F105 antibody reacts with a discontinuous, or conformational, gp120 epitope. This antibody binds to gp120 on the surface of IIIB, SF2, MN, RF, and CC-infected cells. It neutralizes SF2, IIIB, and MN infection at concentrations ranging from 140 ng/ml to 10 µg/ml (Posner et al., 1993, J. Acquir. Immune Defic. Syndr. 6:7-14).

The 2G12 antibody neutralizes SHIV variants HXBc2, KU2, 89.6, 89.6P and KB9 in MT-2 cells and laboratory HIV-1 strains IIIB and RF (weakly neutralizes MN and SF2), and a broad variety of primary isolates. The epitope is conformational and carbohydrate-dependent (Buchacher et al., 1994, AIDS Res Hum Retroviruses 10:359-369; Trkola et al., 1996, Nature 384:184-187).

The antibody may be conjugated to the gold nanoparticles through surface cysteine groups of the antibody. Alternatively, the antibody may be conjugated to $P_1$ through a peptide bond between a surface amino group of the antibody and a carboxylate group of $P_1$, or between a surface carboxylate of the antibody and an amino group of $P_1$. This conjugation may use standard peptide bond formation techniques, such as but not limited to EDC chemistry. The thiol group in $P_1$ may then be used to attach the resulting conjugate to the gold nanoparticle.

The proteins useful within the invention include cyanovirin-N(SEQ ID NO:3). Cyanovirin-N is a highly potent inhibitor of diverse laboratory adapted strains and clinical isolates of HIV-1, as well as HIV-2 and SIV (Boyd et al., 1997, Antimicrob. Agents Chemother. 41:1521-1530). The antiviral activity of cyanovirin-N is mediated, at least in part, through high affinity binding to gp120 (Boyd et al., 1997, Antimicrob. Agents Chemother. 41:1521-1530, Mori et al., 1997, Biochem. Biophys. Res. Comm. 238:218-222). Cyanovirin-N is currently under joint NCI/NIAID investigation as a broad-spectrum virucidal and therapeutic agent against HIV.

Cyanovirin-N may be conjugated to a gold nanoparticle through any free cysteine residue on cyanovirin-N itself. Alternatively, a free amino group (including its N-terminus) or a free carboxylate group (including its C-terminus) of cyanovirin-N may be conjugated to $P_1$ through a peptide bond. The resulting conjugate may be coupled to the gold nanoparticle through the thiol group in $P_1$.

Salts

The compositions described herein may form salts with acids or bases, and such salts are included in the present invention. In one embodiment, the salts are pharmaceutically acceptable salts. The term "salts" embraces addition salts of free acids or free bases that are compositions of the invention. The term "pharmaceutically acceptable salt" refers to salts that possess toxicity profiles within a range that affords utility in pharmaceutical applications. Pharmaceutically unacceptable salts may nonetheless possess properties such as high crystallinity, which have utility in the practice of the present invention, such as for example utility in process of synthesis, purification or formulation of compositions of the invention.

Suitable pharmaceutically acceptable acid addition salts may be prepared from an inorganic acid or from an organic acid. Examples of inorganic acids include hydrochloric, hydrobromic, hydriodic, nitric, carbonic, sulfuric, and phosphoric acids. Appropriate organic acids may be selected from aliphatic, cycloaliphatic, aromatic, araliphatic, heterocyclic, carboxylic and sulfonic classes of organic acids, examples of which include formic, acetic, propionic, succinic, glycolic, gluconic, lactic, malic, tartaric, citric, ascorbic, glucuronic, maleic, fumaric, pyruvic, aspartic, glutamic, benzoic, anthranilic, 4-hydroxybenzoic, phenylacetic, mandelic, embonic (pamoic), methanesulfonic, ethanesulfonic, benzenesulfonic, pantothenic, trifluoromethanesulfonic, 2-hydroxyethanesulfonic, p-toluenesulfonic, sulfanilic, cyclohexylaminosulfonic, stearic, alginic, β-hydroxybutyric, salicylic, galactaric and galacturonic acid. Examples of pharmaceutically unacceptable acid addition salts include, for example, perchlorates and tetrafluoroborates.

Suitable pharmaceutically acceptable base addition salts of compositions of the invention include, for example, metallic salts including alkali metal, alkaline earth metal and transition metal salts such as, for example, calcium, magnesium, potassium, sodium and zinc salts. Pharmaceutically acceptable base addition salts also include organic salts made from basic amines such as, for example, N,N'-dibenzylethylenediamine, chloroprocaine, choline, diethanolamine, ethylenediamine, meglumine (N-methylglucamine) and procaine. Examples of pharmaceutically unacceptable base addition salts include lithium salts and cyanate salts. All of these salts may be prepared from the corresponding composition by reacting, for example, the appropriate acid or base with the composition.

Methods of the Invention

The invention includes a method of preparing a derivatized gold nanoparticle, wherein the gold nanoparticle is complexed with a binding molecule or a salt thereof. The method comprises contacting a solution of the binding molecule with the nanoparticle, to generate a reaction system. The method further comprises stirring the reaction system for an amount of time, whereby the derivatized gold nanoparticle is formed. The method further comprises isolating the derivatized gold nanoparticle from the reaction system.

In one embodiment, the binding molecule is selected from the group consisting of:

a peptide of formula (I) or a salt thereof:

```
                                        (I; SEQ ID NO: 1-P₁)
Arg Ile Asn Asn Ile X Trp Ser Glu Ala Met Met-P₁,
``` wherein X is (2,4)-4-(4-ferrocenyl-1H-1,2,3-triazol-1-yl) pyrrolidine-2-carboxylic acid, and $P_1$ is linked to Arg Ile Asn Asn Ile X Trp Ser Glu Ala Met Met through a peptide bond;

a compound of formula $P_2$—$P_1$, wherein $P_2$ is selected from the group consisting of:

the compound of formula (III) [N-(4-chlorophenyl)-N'-(2,2,6,6-tetramethyl-piperidin-4-yl)-oxalamide]:

(III)

the compound of formula (IV) [N-(4-bromophenyl)-N'-(2,2,6,6-tetramethyl-piperidin-4-yl)-oxalamide]:

(IV)

and
the compound of formula (V) [(R)-1-(4-benzoyl-2-methylpiperazin-1-yl)-2-(4-methoxy-1H-pyrrolo-[2,3-b]pyridin-3-yl)ethane-1,2-dione]:

(V)

wherein the NH group of the piperidinyl group in (III) or (IV), or the $N^1H$ group of the indole group in (V) is bound to $P_1$ through a peptide bond;

an anti-HIV-1-gp120 antibody selected from the group consisting of 17b, F105 and 2G12, wherein a carboxylic group or an amine group in the $F_c$ region of the antibody is optionally bound to $P_1$ through a peptide bond; and cyanovirin-N(SEQ ID NO:3), wherein a free amino group or carboxylate group is optionally bound to $P_1$ through a peptide bond;

wherein $P_1$ is a chemical moiety, wherein $P_1$ comprises at least one thiol group, wherein the nanoparticle is complexed to the binding molecule through a thiol group in the binding molecule.

In one embodiment, $P_1$ comprises at least one cysteine residue. In another embodiment, $P_1$ is βA Gln βA Cys-NH₂, wherein βA is beta-alanine. In yet another embodiment, the peptide of formula (I) is the compound of formula (II) or a salt thereof:

```
(II),                                   (SEQ ID NO: 2)
Arg Ile Asn Asn Ile X Trp Ser Glu Ala Met Met βA
Gln βA Cys-NH₂,
``` wherein βA is beta-alanine. In yet another embodiment, the at least one nanoparticle has an average diameter of about 20 nm.

The invention also includes a method of promoting virolysis of a virus in a mammal. The method comprises administering to the mammal a therapeutically effective amount of a composition comprising at least one pharmaceutically acceptable carrier and at least one gold nanoparticle, wherein the at least one gold nanoparticle is complexed to a binding molecule selected from the group consisting of:

a peptide of formula (I) or a salt thereof:

```
                                        (I; SEQ ID NO: 1-P₁)
Arg Ile Asn Asn Ile X Trp Ser Glu Ala Met Met-P₁,
``` wherein X is (2,4)-4-(4-ferrocenyl-1H-1,2,3-triazol-1-yl) pyrrolidine-2-carboxylic acid, and $P_1$ is linked to Arg Ile Asn Asn Ile X Trp Ser Glu Ala Met Met through a peptide bond;

a compound of formula P$_2$—P$_1$, wherein P$_2$ is selected from the group consisting of:
the compound of formula (III) [N-(4-chlorophenyl)-N'-(2,2,6,6-tetramethyl-piperidin-4-yl)-oxalamide]:

(III)

the compound of formula (IV) [N-(4-bromophenyl)-N'-(2,2,6,6-tetramethyl-piperidin-4-yl)-oxalamide]:

(IV)

and
the compound of formula (V) [(R)-1-(4-benzoyl-2-methylpiperazin-1-yl)-2-(4-methoxy-1H-pyrrolo-[2,3-b]pyridin-3-yl)ethane-1,2-dione]:

(V)

wherein the NH group of the piperidinyl group in (III) or (IV), or the N$^1$H group of the indole group in (V) is bound to P$_1$ through a peptide bond;
an anti-HIV-1-gp120 antibody selected from the group consisting of 17b, F105 and 2G12, wherein a carboxylic group or an amine group in the F$_c$ region of the antibody is optionally bound to P$_1$ through a peptide bond; and
cyanovirin-N(SEQ ID NO:3), wherein a free amino group or carboxylate group is optionally bound to P$_1$ through a peptide bond;
wherein P$_1$ is a chemical moiety, wherein P$_1$ comprises at least one thiol group;
wherein the nanoparticle is complexed to the binding molecule through a thiol group in the binding molecule;
whereby virolysis of the virus in the mammal is promoted.
The invention further includes a method of reducing the rate of or preventing entry of a virus into a cell of a mammal.

The method comprises administering to the mammal a therapeutically effective amount of a composition comprising at least one pharmaceutically acceptable carrier and at least one gold nanoparticle, wherein the at least one gold nanoparticle is complexed to a binding molecule selected from the group consisting of:
a peptide of formula (I) or a salt thereof:

(I),                      (SEQ ID NO: 1-P$_1$)
Arg Ile Asn Asn Ile X Trp Ser Glu Ala Met Met-P$_1$, wherein X is (2,4)-4-(4-ferrocenyl-1H-1,2,3-triazol-1-yl) pyrrolidine-2-carboxylic acid, and P$_1$ is linked to Arg Ile Asn Asn Ile X Trp Ser Glu Ala Met Met through a peptide bond;
a compound of formula P$_2$—P$_1$, wherein P$_2$ is selected from the group consisting of:
the compound of formula (III) [N-(4-chlorophenyl)-N'-(2,2,6,6-tetramethyl-piperidin-4-yl)-oxalamide]:

(III)

the compound of formula (IV) [N-(4-bromophenyl)-N'-(2,2,6,6-tetramethyl-piperidin-4-yl)-oxalamide]:

(IV)

and
the compound of formula (V) [(R)-1-(4-benzoyl-2-methylpiperazin-1-yl)-2-(4-methoxy-1H-pyrrolo-[2,3-b]pyridin-3-yl)ethane-1,2-dione]:

(V)

wherein the NH group of the piperidinyl group in (III) or (IV), or the $N^1H$ group of the indole group in (V) is bound to $P_1$ through a peptide bond;

an anti-HIV-1-gp120 antibody selected from the group consisting of 17b, F105 and 2G12, wherein a carboxylic group or an amine group in the $F_c$ region of the antibody is optionally bound to $P_1$ through a peptide bond; and cyanovirin-N(SEQ ID NO:3), wherein a free amino group or carboxylate group is optionally bound to $P_1$ through a peptide bond;

wherein $P_1$ is a chemical moiety, wherein $P_1$ comprises at least one thiol group;

wherein the nanoparticle is complexed to the binding molecule through a thiol group in the binding molecule;

whereby the entry of the virus into the cell of the mammal is prevented or takes place at a reduced rate as compared to an untreated mammal.

The invention also includes a method of preventing, reducing or treating infection of a virus in a mammal. The method comprises administering to the mammal a therapeutically effective amount of a composition comprising at least one pharmaceutically acceptable carrier and at least one gold nanoparticle, wherein the at least one gold nanoparticle is complexed to a binding molecule selected from the group consisting of:

a peptide of formula (I) or a salt thereof:

(I),                                    (SEQ ID NO: 1-$P_1$)
Arg Ile Asn Asn Ile X Trp Ser Glu Ala Met Met-$P_1$, wherein X is (2,4)-4-(4-ferrocenyl-1H-1,2,3-triazol-1-yl)pyrrolidine-2-carboxylic acid, and $P_1$ is linked to Arg Ile Asn Asn Ile X Trp Ser Glu Ala Met Met through a peptide bond;

a compound of formula $P_2$—$P_1$, wherein $P_2$ is selected from the group consisting of:

the compound of formula (III) [N-(4-chlorophenyl)-N'-(2,2,6,6-tetramethyl-piperidin-4-yl)-oxalamide]:

(III)

the compound of formula (IV) [N-(4-bromophenyl)-N'-(2,2,6,6-tetramethyl-piperidin-4-yl)-oxalamide]:

(IV)

and
the compound of formula (V) [(R)-1-(4-benzoyl-2-methylpiperazin-1-yl)-2-(4-methoxy-1H-pyrrolo-[2,3-b]pyridin-3-yl)ethane-1,2-dione]:

(V)

wherein the NH group of the piperidinyl group in (III) or (IV), or the $N^1H$ group of the indole group in (V) is bound to $P_1$ through a peptide bond;

an anti-HIV-1-gp120 antibody selected from the group consisting of 17b, F105 and 2G12, wherein a carboxylic group or an amine group in the $F_c$ region of the antibody is optionally bound to $P_1$ through a peptide bond; and cyanovirin-N(SEQ ID NO:3), wherein a free amino group or carboxylate group is optionally bound to $P_1$ through a peptide bond;

wherein $P_1$ is a chemical moiety, wherein $P_1$ comprises at least one thiol group;

wherein the nanoparticle is complexed to the binding molecule through a thiol group in the binding molecule;

whereby the infection of the virus in the mammal is prevented, reduced or treated.

The invention further includes a method of promoting virolysis of a virus in a mammal. The method comprises administering to the mammal a therapeutically effective amount of a composition comprising at least one pharmaceutically acceptable carrier and a peptide of formula (I) or a salt thereof:

(I),                                    (SEQ ID NO: 1-$P_1$)
Arg Ile Asn Asn Ile X Trp Ser Glu Ala Met Met-$P_1$, wherein:
X is (2,4)-4-(4-ferrocenyl-1H-1,2,3-triazol-1-yl)pyrrolidine-2-carboxylic acid, and
$P_1$ is linked to Arg Ile Asn Asn Ile X Trp Ser Glu Ala Met Met through a peptide bond;
wherein $P_1$ is a chemical moiety, wherein $P_1$ comprises at least one thiol group; whereby virolysis of the virus in the mammal is promoted.

The invention also includes a method of reducing the rate of or preventing entry of a virus into a cell of a mammal. The method comprises administering to the mammal a therapeutically effective amount of a composition comprising at least one pharmaceutically acceptable carrier and a peptide of formula (I) or a salt thereof:

(I),                                    (SEQ ID NO: 1-$P_1$)
Arg Ile Asn Asn Ile X Trp Ser Glu Ala Met Met-$P_1$, wherein:
X is (2,4)-4-(4-ferrocenyl-1H-1,2,3-triazol-1-yl)pyrrolidine-2-carboxylic acid, and
$P_1$ is linked to Arg Ile Asn Asn Ile X Trp Ser Glu Ala Met Met through a peptide bond; wherein $P_1$ is a chemical moiety, wherein $P_1$ comprises at least one thiol group; whereby the entry of the virus into the cell of the mammal is prevented or takes place at a reduced rate as compared to an untreated mammal.

The invention further includes a method of preventing, reducing or treating infection of a virus in a mammal. The method comprises administering to the mammal a therapeutically effective amount of a composition comprising at least one pharmaceutically acceptable carrier and a peptide of formula (I) or a salt thereof:

(I),                                        (SEQ ID NO: 1-P₁)
Arg Ile Asn Asn Ile X Trp Ser Glu Ala Met Met-P₁, wherein:

X is (2,4)-4-(4-ferrocenyl-1H-1,2,3-triazol-1-yl)pyrrolidine-2-carboxylic acid, and P₁ is linked to Arg Ile Asn Asn Ile X Trp Ser Glu Ala Met Met through a peptide bond;

wherein P₁ is a chemical moiety, wherein P₁ comprises at least one thiol group; whereby the infection of the virus in the mammal is prevented, reduced or treated.

In one embodiment, the virus is HIV-1, influenza, ebola or dengue. In another embodiment, the virus is HIV-1. In yet another embodiment, P₁ comprises at least one cysteine residue. In yet another embodiment, P₁ is βA Gln βA Cys-NH₂, wherein βA is beta-alanine. In yet another embodiment, the peptide of formula (I) is the compound of formula (II) or a salt thereof:

(II),                                       (SEQ ID NO: 2)
Arg Ile Asn Asn Ile X Trp Ser Glu Ala Met Met βA
Gln βA Cys-NH₂, wherein βA is beta-alanine. In yet another embodiment, the composition further comprises at least one gold nanoparticle, wherein the at least one nanoparticle is complexed to the peptide of formula (I) through the at least one thiol group. In yet another embodiment, the at least one nanoparticle has an average diameter of about 20 nm. In yet another embodiment, the mammal is further administered at least one additional compound useful for treating viral infections. In yet another embodiment, the at least one additional compound is selected from the group consisting of antiviral combination drugs, entry and fusion inhibitors, integrase inhibitors, non-nucleoside reverse transcriptase inhibitors, nucleoside reverse transcriptase inhibitors, protease inhibitors, and combinations thereof. In yet another embodiment, the at least one additional compound and the peptide are co-formulated. In yet another embodiment, the peptide is encapsulated in a hydrogel. In yet another embodiment, the hydrogel is pH-responsive. In yet another embodiment, the hydrogel comprises a polymerized mixture of methacrylic acid and PEG-monomethyl ether monomethacrylate. In yet another embodiment, the composition is administered orally, nasally, rectally, intravaginally, parenterally, buccally, sublingually, intragastrically or topically to the mammal. In yet another embodiment, the mammal is human.

Antibodies and Equivalents Useful within the Methods of the Invention

Using conventional techniques, the skilled artisan may utilize the nucleotide and amino acid sequences for the envelope proteins described herein to prepare antigenic peptides for use in generating corresponding anti-envelope protein antibodies. Alternatively, the skilled artisan may utilize commercially available antibodies against the envelope proteins and use them within the limits of the invention. The skilled artisan may also obtain commercially available antibodies against the envelope proteins and modify them as wished, by methods such as coupling to other antibodies, partial digestion, pegylation or covalent modification. This modified antibody may then be utilized within the limits of the invention as needed.

The antibodies used in the practice of the present invention may be polyclonal or monoclonal. Monoclonal antibodies are preferred. The antibody is preferably a chimeric antibody. For human use, the antibody is preferably a humanized chimeric antibody.

It may be appreciated that the anti-envelope protein antibody used in the practice of the invention may be monovalent, divalent or polyvalent in order to achieve envelope protein binding. Monovalent immunoglobulins are dimers (HL) formed of a hybrid heavy chain associated through disulfide bridges with a hybrid light chain. Divalent immunoglobulins are tetramers (H2L2) formed of two dimers associated through at least one disulfide bridge.

The invention also includes functional equivalents of the antibodies described herein. Functional equivalents have binding characteristics comparable to those of the antibodies, and include, for example, hybridized and single chain antibodies, as well as fragments thereof. Methods of producing such functional equivalents are disclosed in PCT Application No. WO 1993/21319 and No. WO 1989/09622. Functional equivalents include polypeptides with amino acid sequences substantially the same as the amino acid sequence of the variable or hypervariable regions of the antibodies raised against envelope proteins according to the practice of the present invention.

Functional equivalents of the anti-envelope protein antibodies further include fragments of antibodies that have the same, or substantially the same, binding characteristics to those of the whole antibody. Such fragments may contain one or both Fab fragments or the F(ab')₂ fragment. Preferably the antibody fragments contain all six complement determining regions of the whole antibody, although fragments containing fewer than all of such regions, such as three, four or five complement determining regions, are also functional. The functional equivalents are members of the IgG immunoglobulin class and subclasses thereof, but may be or may combine any one of the following immunoglobulin classes: IgM, IgA, IgD, or IgE, and subclasses thereof. Heavy chains of various subclasses, such as the IgG subclasses, are responsible for different effector functions and thus, by choosing the desired heavy chain constant region, hybrid antibodies with desired effector function are produced. Preferred constant regions are gamma 1 (IgG1), gamma 2 (IgG2 and IgG), gamma 3 (IgG3) and gamma 4 (IgG4). The light chain constant region can be of the kappa or lambda type.

The monoclonal antibodies may be advantageously cleaved by proteolytic enzymes to generate fragments retaining the envelope protein binding site. For example, proteolytic treatment of IgG antibodies with papain at neutral pH generates two identical so-called "Fab" fragments, each containing one intact light chain disulfide-bonded to a fragment of the heavy chain (Fc). Each Fab fragment contains one antigen-combining site. The remaining portion of the IgG molecule is a dimer known as "Fc". Similarly, pepsin cleavage at pH 4 results in the so-called F(ab')2 fragment.

Single chain antibodies or Fv fragments are polypeptides that consist of the variable region of the heavy chain of the antibody linked to the variable region of the light chain, with or without an interconnecting linker Thus, the Fv comprises an antibody combining site.

Hybrid antibodies may be employed. Hybrid antibodies have constant regions derived substantially or exclusively from human antibody constant regions and variable regions derived substantially or exclusively from the sequence of the variable region of a monoclonal antibody from each stable hybridoma.

Methods for preparation of fragments of antibodies are known to those skilled in the art. See, Goding, "Monoclonal Antibodies Principles and Practice", Academic Press (1983), p. 119-123. Fragments of the monoclonal antibodies containing the antigen binding site, such as Fab and F(ab')2 fragments, may be preferred in therapeutic applications, owing to their reduced immunogenicity. Such fragments are less immunogenic than the intact antibody, which contains the immunogenic Fc portion. Hence, as used herein, the term "antibody" includes intact antibody molecules and fragments thereof that retain antigen binding ability.

When the antibody used in the practice of the invention is a polyclonal antibody (IgG), the antibody is generated by inoculating a suitable animal with an envelope protein or a fragment thereof. Antibodies produced in the inoculated animal that specifically bind the envelope protein are then isolated from fluid obtained from the animal. Anti-envelope protein antibodies may be generated in this manner in several non-human mammals such as, but not limited to, goat, sheep, horse, rabbit, and donkey. Methods for generating polyclonal antibodies are well known in the art and are described, for example in Harlow et al. (In: Antibodies, A Laboratory Manual, 1988, Cold Spring Harbor, N.Y.). These methods are not repeated herein as they are commonly used in the art of antibody technology.

When the antibody used in the methods used in the practice of the invention is a monoclonal antibody, the antibody is generated using any well-known monoclonal antibody preparation procedures such as those described, for example, in Harlow et al. (supra) and in Tuszynski et al. (Blood 1988, 72:109-115). Given that these methods are well known in the art, they are not replicated herein. Generally, monoclonal antibodies directed against a desired antigen are generated from mice immunized with the antigen using standard procedures as referenced herein. Monoclonal antibodies directed against full length or fragments of target structure may be prepared using the techniques described in Harlow et al. (supra).

The effects of sensitization in the therapeutic use of animal-origin monoclonal antibodies in the treatment of human disease may be diminished by employing a hybrid molecule generated from the same Fab fragment, but a different Fc fragment, than contained in monoclonal antibodies previously administered to the same subject. It is contemplated that such hybrid molecules formed from the anti-target-structure monoclonal antibodies may be used in the present invention. The effects of sensitization are further diminished by preparing animal/human chimeric antibodies, e.g., mouse/human chimeric antibodies, or humanized (i.e. CDR-grafted) antibodies. Such monoclonal antibodies comprise a variable region, i.e., antigen binding region, and a constant region derived from different species. By "chimeric" antibody is meant an antibody that comprises elements partly derived from one species and partly derived from at least one other species, e.g., a mouse/human chimeric antibody.

Chimeric animal-human monoclonal antibodies may be prepared by conventional recombinant DNA and gene transfection techniques well known in the art. The variable region genes of a mouse antibody-producing myeloma cell line of known antigen-binding specificity are joined with human immunoglobulin constant region genes. When such gene constructs are transfected into mouse myeloma cells, the antibodies produced are largely human but contain antigen-binding specificities generated in mice. As demonstrated by Morrison et al., 1984, Proc. Natl. Acad. Sci. USA 81:6851-6855, both chimeric heavy chain V region exon (VH)-human heavy chain C region genes and chimeric mouse light chain V region exon (VK)-human K light chain gene constructs may be expressed when transfected into mouse myeloma cell lines. When both chimeric heavy and light chain genes are transfected into the same myeloma cell, an intact H2L2 chimeric antibody is produced. The methodology for producing such chimeric antibodies by combining genomic clones of V and C region genes is described in the above-mentioned paper of Morrison et al., and by Boulianne et al. (Nature 1984, 312:642-646). Also see Tan et al. (J. Immunol. 1985, 135: 3564-3567) for a description of high level expression from a human heavy chain promotor of a human-mouse chimeric K chain after transfection of mouse myeloma cells. As an alternative to combining genomic DNA, cDNA clones of the relevant V and C regions may be combined for production of chimeric antibodies, as described by Whitte et al. (Protein Eng. 1987, 1:499-505) and Liu et al. (Proc. Natl. Acad. Sci. USA 1987, 84:3439-3443).

For examples of the preparation of chimeric antibodies, see the following U.S. Pat. Nos. 5,292,867; 5,091,313; 5,204, 244; 5,202,238; and 5,169,939. The entire disclosures of these patents, and the publications mentioned in the preceding paragraph, are incorporated herein by reference. Any of these recombinant techniques are available for production of rodent/human chimeric monoclonal antibodies against envelope proteins.

To further reduce the immunogenicity of murine antibodies, "humanized" antibodies have been constructed in which only the minimum necessary parts of the mouse antibody, the complementarity-determining regions (CDRs), are combined with human V region frameworks and human C regions (Jones et al., 1986, Nature 321:522-525; Verhoeyen et al., 1988, Science 239:1534-1536; Hale et al., 1988, Lancet 2:1394-1399; Queen et al., 1989, Proc. Natl. Acad. Sci. USA 86:10029-10033). The entire disclosures of the aforementioned papers are incorporated herein by reference. This technique results in the reduction of the xenogeneic elements in the humanized antibody to a minimum. Rodent antigen binding sites are built directly into human antibodies by transplanting only the antigen binding site, rather than the entire variable domain, from a rodent antibody. This technique is available for production of chimeric rodent/human anti-envelope protein antibodies of reduced human immunogenicity.

Combination Therapies

The compositions of the invention are useful in the methods of the invention in combination with one or more additional compounds useful for treating viral infections, such as but not limited to HIV infections. These additional compounds may comprise compounds or compositions identified herein, or compounds (e.g., commercially available compounds) known to treat, prevent, or reduce the symptoms of viral infections.

In non-limiting examples, the compositions of the invention may be used in combination with one or more of the following anti-HIV drugs:

HIV Combination Drugs:

efavirenz, emtricitabine or tenofovir disoproxil fumarate (Atripla®/BMS, Gilead); lamivudine or zidovudine (Combivir®/GSK); abacavir or lamivudine (Epzicom®/GSK); abacavir, lamivudine or zidovudine (Trizivir®/GSK); emtricitabine, tenofovir disoproxil fumarate (Truvada®/Gilead).

Entry and Fusion Inhibitors:
maraviroc (Celsentri®, Selzentry®/Pfizer); pentafuside or enfuvirtide (Fuzeon®/Roche, Trimeris).

Integrase Inhibitors:
raltegravir or MK-0518 (Isentress®/Merck).

Non-Nucleoside Reverse Transcriptase Inhibitors:
delavirdine mesylate or delavirdine (Rescriptor®/Pfizer); nevirapine (Viramune®/Boehringer Ingelheim); stocrin or efavirenz (Sustiva®/BMS); etravirine (Intelence®/Tibotec).

Nucleoside Reverse Transcriptase Inhibitors:
lamivudine or 3TC (Epivir®/GSK); FTC, emtricitabina or coviracil (Emtriva®/Gilead); abacavir (Ziagen®/GSK); zidovudina, ZDV, azidothymidine or AZT (Retrovir®/GSK); ddI, dideoxyinosine or didanosine (Videx®/BMS); abacavir sulfate plus lamivudine (Epzicom®/GSK); stavudine, d4T, or estavudina (Zerit®/BMS); tenofovir, PMPA prodrug, or tenofovir disoproxil fumarate (Viread®/Gilead).

Protease Inhibitors:
amprenavir (Agenerase®/GSK, Vertex); atazanavir (Reyataz®/BMS); tipranavir (Aptivus®/Boehringer Ingelheim); darunavir (Prezist®/Tibotec); fosamprenavir (Telzir®, Lexiva®/GSK, Vertex); indinavir sulfate (Crixivan®/Merck); saquinavir mesylate (Invirase®/Roche); lopinavir or ritonavir (Kaletra®/Abbott); nelfinavir mesylate (Viracept®/Pfizer); ritonavir (Norvir®/Abbott).

A synergistic effect may be calculated, for example, using suitable methods such as, for example, the Sigmoid-$E_{max}$ equation (Holford & Scheiner, 19981, Clin. Pharmakokinet 6:429-453), the equation of Loewe additivity (Loewe & Muischnek, 1926, Arch. Exp. Pathol Pharmacol. 114: 313-326) and the median-effect equation (Chou & Talalay, 1984, Adv. Enzyme Regul. 22:27-55). Each equation referred to above may be applied to experimental data to generate a corresponding graph to aid in assessing the effects of the drug combination. The corresponding graphs associated with the equations referred to above are the concentration-effect curve, isobologram curve and combination index curve, respectively.

Administration/Dosage/Formulations

Routes of administration of any of the compositions of the invention include oral, nasal, rectal, intravaginal, parenteral (e.g., IM, IV and SC), buccal, sublingual or topical. The regimen of administration may affect what constitutes an effective amount. The therapeutic formulations may be administered to the subject either prior to or after the onset of a viral infection. Further, several divided dosages, as well as staggered dosages may be administered daily or sequentially, or the dose may be continuously infused, or may be a bolus injection. Further, the dosages of the therapeutic formulations may be proportionally increased or decreased as indicated by the exigencies of the therapeutic or prophylactic situation.

Administration of the compositions of the present invention to a subject, preferably a mammal, more preferably a human, may be carried out using known procedures, at dosages and for periods of time effective to treat a viral infection in the subject. An effective amount of the therapeutic compound necessary to achieve a therapeutic effect may vary according to factors such as the state of the disease or disorder in the subject; the age, sex, and weight of the subject; and the ability of the therapeutic compound to treat a viral infection in the subject. Dosage regimens may be adjusted to provide the optimum therapeutic response. For example, several divided doses may be administered daily or the dose may be proportionally reduced as indicated by the exigencies of the therapeutic situation. A non-limiting example of an effective dose range for a therapeutic compound useful within the invention is from about 1 and 5,000 mg/kg of body weight/per day. One of ordinary skill in the art would be able to study the relevant factors and make the determination regarding the effective amount of the therapeutic compound without undue experimentation.

Actual dosage levels of the active ingredients in the pharmaceutical compositions of this invention may be varied so as to obtain an amount of the active ingredient that is effective to achieve the desired therapeutic response for a particular subject, composition, and mode of administration, without being toxic to the subject.

In particular, the selected dosage level depends upon a variety of factors, including the activity of the particular compound employed, the time of administration, the rate of excretion of the compound, the duration of the treatment, other drugs, compounds or materials used in combination with the compound, the age, sex, weight, condition, general health and prior medical history of the subject being treated, and like factors well, known in the medical arts.

A medical doctor, e.g., physician or veterinarian, having ordinary skill in the art may readily determine and prescribe the effective amount of the pharmaceutical composition required. For example, the physician or veterinarian may start doses of the compounds useful within the invention employed in the pharmaceutical composition at levels lower than that required in order to achieve the desired therapeutic effect and gradually increase the dosage until the desired effect is achieved.

In one embodiment, it is especially advantageous to formulate the compound in dosage unit form for ease of administration and uniformity of dosage. Dosage unit form as used herein refers to physically discrete units suited as unitary dosages for the subjects to be treated; each unit containing a predetermined quantity of therapeutic compound calculated to produce the desired therapeutic effect in association with the required pharmaceutical vehicle. The dosage unit forms of the invention are dictated by and directly dependent on the unique characteristics of the therapeutic compound and the particular therapeutic effect to be achieved, and the limitations inherent in the art of compounding/formulating such a therapeutic compound for the treatment of an HIV-1 infection in a subject.

In one embodiment, the compositions of the invention are formulated using one or more pharmaceutically acceptable excipients or carriers. In one embodiment, the pharmaceutical compositions of the invention comprise a therapeutically effective amount of a compound useful within the invention and a pharmaceutically acceptable carrier.

The language "pharmaceutically acceptable carrier" includes a pharmaceutically acceptable salt, pharmaceutically acceptable material, composition or carrier, such as a liquid or solid filler, diluent, excipient, solvent or encapsulating material, involved in carrying or transporting a compound(s) of the present invention within or to the subject such that it may perform its intended function. Typically, such compounds are carried or transported from one organ, or portion of the body, to another organ, or portion of the body. Each salt or carrier must be "acceptable" in the sense of being compatible with the other ingredients of the formulation, and not injurious to the subject.

The carrier may be a solvent or dispersion medium containing, for example, water, ethanol, polyol (for example, glycerol, propylene glycol, and liquid polyethylene glycol, and the like), suitable mixtures thereof, and vegetable oils. The proper fluidity may be maintained, for example, by the use of a coating such as lecithin, by the maintenance of the required particle size in the case of dispersion and by the use of surfactants. Prevention of the action of microorganisms may be achieved by various antibacterial and antifungal agents, for example, parabens, chlorobutanol, phenol, ascorbic acid, thimerosal, and the like. In many cases, it will be preferable to include isotonic agents, for example, sugars, sodium chloride, or polyalcohols such as mannitol and sorbitol, in the composition. Prolonged absorption of the injectable compositions may be brought about by including in the composition an agent which delays absorption, for example, aluminum monostearate or gelatin. In one embodiment, the pharmaceutically acceptable carrier is not DMSO alone.

In one embodiment, the compositions of the invention are administered to the subject in dosages that range from one to five times per day or more. In another embodiment, the compositions of the invention are administered to the subject in range of dosages that include, but are not limited to, once every day, every two, days, every three days to once a week, and once every two weeks. It is readily apparent to one skilled in the art that the frequency of administration of the various combination compositions of the invention varies from individual to individual depending on many factors including, but not limited to, age, disease or disorder to be treated, gender, overall health, and other factors. Thus, the invention should not be construed to be limited to any particular dosage regime and the precise dosage and composition to be administered to any subject are determined by the attending physical taking all other factors about the subject into account.

Compounds useful within the invention for administration may be in the range of from about 1 mg to about 10,000 mg, about 20 mg to about 9,500 mg, about 40 mg to about 9,000 mg, about 75 mg to about 8,500 mg, about 150 mg to about 7,500 mg, about 200 mg to about 7,000 mg, about 3050 mg to about 6,000 mg, about 500 mg to about 5,000 mg, about 750 mg to about 4,000 mg, about 1 mg to about 3,000 mg, about 10 mg to about 2,500 mg, about 20 mg to about 2,000 mg, about 25 mg to about 1,500 mg, about 50 mg to about 1,000 mg, about 75 mg to about 900 mg, about 100 mg to about 800 mg, about 250 mg to about 750 mg, about 300 mg to about 600 mg, about 400 mg to about 500 mg, and any and all whole or partial increments therebetween.

In some embodiments, the dose of a compound useful within the invention is from about 1 mg and about 2,500 mg. In some embodiments, a dose of a compound useful within the invention used in compositions described herein is less than about 10,000 mg, or less than about 8,000 mg, or less than about 6,000 mg, or less than about 5,000 mg, or less than about 3,000 mg, or less than about 2,000 mg, or less than about 1,000 mg, or less than about 500 mg, or less than about 200 mg, or less than about 50 mg. Similarly, in some embodiments, a dose of a second compound (i.e., an HIV-1 antiviral) as described herein is less than about 1,000 mg, or less than about 800 mg, or less than about 600 mg, or less than about 500 mg, or less than about 400 mg, or less than about 300 mg, or less than about 200 mg, or less than about 100 mg, or less than about 50 mg, or less than about 40 mg, or less than about 30 mg, or less than about 25 mg, or less than about 20 mg, or less than about 15 mg, or less than about 10 mg, or less than about 5 mg, or less than about 2 mg, or less than about 1 mg, or less than about 0.5 mg, and any and all whole or partial increments therebetween.

In one embodiment, the present invention is directed to a packaged pharmaceutical composition comprising a container holding a therapeutically effective amount of a compound useful within the invention, alone or in combination with a second pharmaceutical agent; and instructions for using the compound to treat, prevent, or reduce one or more symptoms of an HIV-1 infection in a subject.

Granulating techniques are well known in the pharmaceutical art for modifying starting powders or other particulate materials of an active ingredient. The powders are typically mixed with a binder material into larger permanent free-flowing agglomerates or granules referred to as a "granulation." For example, solvent-using "wet" granulation processes are generally characterized in that the powders are combined with a binder material and moistened with water or an organic solvent under conditions resulting in the formation of a wet granulated mass from which the solvent must then be evaporated.

Melt granulation generally consists in the use of materials that are solid or semi-solid at room temperature (i.e. having a relatively low softening or melting point range) to promote granulation of powdered or other materials, essentially in the absence of added water or other liquid solvents. The low melting solids, when heated to a temperature in the melting point range, liquefy to act as a binder or granulating medium. The liquefied solid spreads itself over the surface of powdered materials with which it is contacted, and on cooling, forms a solid granulated mass in which the initial materials are bound together. The resulting melt granulation may then be provided to a tablet press or be encapsulated for preparing the oral dosage form. Melt granulation improves the dissolution rate and bioavailability of an active (i.e. drug) by forming a solid dispersion or solid solution.

U.S. Pat. No. 5,169,645 discloses directly compressible wax-containing granules having improved flow properties. The granules are obtained when waxes are admixed in the melt with certain flow improving additives, followed by cooling and granulation of the admixture. In certain embodiments, only the wax itself melts in the melt combination of the wax(es) and additives(s), and in other cases both the wax(es) and the additives(s) will melt.

The present invention also includes a multi-layer tablet comprising a layer providing for the delayed release of one or more compounds useful within the invention, and a further layer providing for the immediate release of a medication for HIV-1 infection. Using a wax/pH-sensitive polymer mix, a gastric insoluble composition may be obtained in which the active ingredient is entrapped, ensuring its delayed release.

Formulations may be employed in admixtures with conventional excipients, i.e., pharmaceutically acceptable organic or inorganic carrier substances suitable for oral, parenteral, nasal, intravenous, subcutaneous, enteral, or any other suitable mode of administration, known to the art. The pharmaceutical preparations may be sterilized and if desired mixed with auxiliary agents, e.g., lubricants, preservatives, stabilizers, wetting agents, emulsifiers, salts for influencing osmotic pressure buffers, coloring, flavoring and/or aromatic substances and the like. They may also be combined where desired with other active agents, e.g., other analgesic agents. For oral application, particularly suitable are tablets, dragees, liquids, drops, suppositories, or capsules, caplets and gelcaps. The compositions intended for oral use may be prepared according to any method known in the art and such compositions may contain one or more agents selected from the group consisting of inert, non-toxic pharmaceutically excipients that are suitable for the manufacture of tablets. Such excipients include, for example an inert diluent such as lactose; granulating and disintegrating agents such as cornstarch; binding agents such as starch; and lubricating agents such as magnesium stearate. The tablets may be uncoated or they may be coated by known techniques for elegance or to delay the release of the active ingredients. Formulations for oral use may also be presented as hard gelatin capsules wherein the active ingredient is mixed with an inert diluent.

The term "container" includes any receptacle for holding the pharmaceutical composition. For example, in one embodiment, the container is the packaging that contains the pharmaceutical composition. In other embodiments, the container is not the packaging that contains the pharmaceutical composition, i.e., the container is a receptacle, such as a box or vial that contains the packaged pharmaceutical composition or unpackaged pharmaceutical composition and the instructions for use of the pharmaceutical composition. Moreover, packaging techniques are well known in the art. It should be understood that the instructions for use of the pharmaceutical composition may be contained on the packaging containing the pharmaceutical composition, and as such the instructions form an increased functional relationship to the packaged product. However, it should be understood that the instructions may contain information pertaining to the compound's ability to perform its intended function, e.g., treating, preventing, or reducing an HIV-1 infection in a subject.

The compounds for use in the invention may be formulated for administration by any suitable route, such as for oral or parenteral, for example, transdermal, transmucosal (e.g., sublingual, lingual, (trans)buccal, (trans)urethral, vaginal (e.g., trans- and perivaginally), (intra)nasal and (trans)rectal), intravesical, intrapulmonary, intraduodenal, intragastrical, intrathecal, subcutaneous, intramuscular, intradermal, intra-arterial, intravenous, intrabronchial, inhalation, and topical administration.

Suitable compositions and dosage forms include, for example, tablets, capsules, caplets, pills, gel caps, troches, dispersions, suspensions, solutions, syrups, granules, beads, transdermal patches, gels, powders, pellets, magmas, lozenges, creams, pastes, plasters, lotions, discs, suppositories, liquid sprays for nasal or oral administration, dry powder or aerosolized formulations for inhalation, compositions and formulations for intravesical administration and the like. It should be understood that the formulations and compositions that would be useful in the present invention are not limited to the particular formulations and compositions that are described herein.

Oral Administration:

For oral administration, the compositions of the invention may be in the form of tablets or capsules prepared by conventional means with pharmaceutically acceptable excipients such as binding agents (e.g., polyvinylpyrrolidone, hydroxypropylcellulose or hydroxypropylmethylcellulose); fillers (e.g., cornstarch, lactose, microcrystalline cellulose or calcium phosphate); lubricants (e.g., magnesium stearate, talc, or silica); disintegrates (e.g., sodium starch glycollate); or wetting agents (e.g., sodium lauryl sulphate). If desired, the tablets may be coated using suitable methods and coating materials such as OPADRY™ film coating systems available from Colorcon, West Point, Pa. (e.g., OPADRY™ OY Type, OYC Type, Organic Enteric OY-P Type, Aqueous Enteric OY-A Type, OY-PM Type and OPADRY™ White, 32K18400). Liquid preparation for oral administration may be in the form of solutions, syrups or suspensions. The liquid preparations may be prepared by conventional means with pharmaceutically acceptable additives such as suspending agents (e.g., sorbitol syrup, methyl cellulose or hydrogenated edible fats); emulsifying agent (e.g., lecithin or acacia); non-aqueous vehicles (e.g., almond oil, oily esters or ethyl alcohol); and preservatives (e.g., methyl or propyl p-hydroxy benzoates or sorbic acid).

Parenteral Administration:

For parenteral administration, the compositions of the invention may be formulated for injection or infusion, for example, intravenous, intramuscular or subcutaneous injection or infusion, or for administration in a bolus dose and/or continuous infusion. Suspensions, solutions or emulsions in an oily or aqueous vehicle, optionally containing other formulatory agents such as suspending, stabilizing and/or dispersing agents may be used.

Additional Administration Forms:

Additional dosage forms of this invention include dosage forms as described in U.S. Pat. Nos. 6,340,475, 6,488,962, 6,451,808, 5,972,389, 5,582,837, and 5,007,790. Additional dosage forms of this invention also include dosage forms as described in U.S. Patent Applications Nos. 2003/0147952, 2003/0104062, 2003/0104053, 2003/0044466, 2003/0039688, and 2002/0051820. Additional dosage forms of this invention also include dosage forms as described in PCT Applications Nos. WO 03/35041, WO 03/35040, WO 03/35029, WO 03/35177, WO 03/35039, WO 02/96404, WO 02/32416, WO 01/97783, WO 01/56544, WO 01/32217, WO 98/55107, WO 98/11879, WO 97/47285, WO 93/18755, and WO 90/11757.

Controlled Release Formulations and Drug Delivery Systems:

In certain embodiments, the formulations of the present invention may be, but are not limited to, short-term, rapid-offset, as well as controlled, for example, sustained release, delayed release and pulsatile release formulations.

The term sustained release is used in its conventional sense to refer to a drug formulation that provides for gradual release of a drug over an extended period of time, and that may, although not necessarily, result in substantially constant blood levels of a drug over an extended time period. The period of time may be as long as a month or more and should be a release which is longer that the same amount of agent administered in bolus form.

For sustained release, the compounds may be formulated with a suitable polymer or hydrophobic material which provides sustained release properties to the compounds. As such, the compounds for use the method of the invention may be administered in the form of microparticles, for example, by injection or in the form of wafers or discs by implantation.

In a preferred embodiment of the invention, the compounds useful within the invention are administered to a subject, alone or in combination with another pharmaceutical agent, using a sustained release formulation.

The term delayed release is used herein in its conventional sense to refer to a drug formulation that provides for an initial release of the drug after some delay following drug administration and that may, although not necessarily, include a delay of from about 10 minutes up to about 12 hours.

The term pulsatile release is used herein in its conventional sense to refer to a drug formulation that provides release of the drug in such a way as to produce pulsed plasma profiles of the drug after drug administration.

The term immediate release is used in its conventional sense to refer to a drug formulation that provides for release of the drug immediately after drug administration.

As used herein, short-term refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes and any or all whole or partial increments thereof after drug administration after drug administration.

As used herein, rapid-offset refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes, and any and all whole or partial increments thereof after drug administration.

Dosing:

The therapeutically effective amount or dose of a compound of the present invention will depend on the age, sex and weight of the subject, the current medical condition of the subject and the nature of the infection by an HIV-1 being treated. The skilled artisan will be able to determine appropriate dosages depending on these and other factors.

A suitable dose of a compound of the present invention may be in the range of from about 0.01 mg to about 5,000 mg per day, such as from about 0.1 mg to about 1,000 mg, for example, from about 1 mg to about 500 mg, such as about 5 mg to about 250 mg per day. The dose may be administered in a single dosage or in multiple dosages, for example from 1 to 4 or more times per day. When multiple dosages are used, the amount of each dosage may be the same or different. For example, a dose of 1 mg per day may be administered as two 0.5 mg doses, with about a 12-hour interval between doses.

It is understood that the amount of compound dosed per day may be administered, in non-limiting examples, every day, every other day, every 2 days, every 3 days, every 4 days, or every 5 days.

The compounds for use in the method of the invention may be formulated in unit dosage form. The term "unit dosage form" refers to physically discrete units suitable as unitary dosage for subjects undergoing treatment, with each unit containing a predetermined quantity of active material calculated to produce the desired therapeutic effect, optionally in association with a suitable pharmaceutical carrier. The unit dosage form may be for a single daily dose or one of multiple daily doses (e.g., about 1 to 4 or more times per day). When multiple daily doses are used, the unit dosage form may be the same or different for each dose.

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

It is to be understood that, wherever values and ranges are provided herein, the description in range format is merely for convenience and brevity and should not be construed as an inflexible limitation on the scope of the invention. Accordingly, all values and ranges encompassed by these values and ranges are meant to be encompassed within the scope of the present invention. Moreover, all values that fall within these ranges, as well as the upper or lower limits of a range of values, are also contemplated by the present application. The description of a range should be considered to have specifically disclosed all the possible sub-ranges as well as individual numerical values within that range and, when appropriate, partial integers of the numerical values within ranges. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

The following examples further illustrate aspects of the present invention. However, they are in no way a limitation of the teachings or disclosure of the present invention as set forth herein.

EXAMPLES

The invention is now described with reference to the following Examples. These Examples are provided for the purpose of illustration only, and the invention is not limited to these Examples, but rather encompasses all variations that are evident as a result of the teachings provided herein.

Materials:

All Fmoc-protected α- and β-amino acids, O-benzotriazole-N,N,N',N'-tetramethyl-uronium hexafluorophosphate (HBTU), 1-hydroxybenzotriazole (HOBt), Rink amide resin {(4-(2',4'-dimethoxyphenyl-Fmoc-aminomethyl)phenoxy resin) with a 0.55 mmol/g substitution}, N,N-dimethylformamide (DMF), pyridine and N,N-diisopropylethylamine (DIPEA) were purchased from Chem-Impex International Inc.

Ethynylferrocene and copper(I) iodide (CuI) were purchased from Sigma-Aldrich (St. Louis, Mo.) and used without further purification. Fmoc-cis-4-azidoproline was synthesized starting with commercially available trans-Hyp-OH.

Gold(III) chloride hydrate and citric acid were purchased from Sigma-Aldrich, bis(p-sulfonatophenyl)phenylphosphine dehydrate dipotassium salt (BSPP) was purchased from Strem Chemicals. AuNPs (20 nm) were purchased from BD International Ted Pella.

Modified human osteosarcoma cells (HOS.T4.R5) engineered to express CD4 and CCR5, as well as pNL4-3.Luc R-E-, were obtained from Dr. Nathaniel Landau (Connor et al., 1995, Virology 206:935-944).

The HOS.T4.R5 cells were grown in DMEM supplemented with 10% FBS, 2.5% HEPES, 1% penicillin-streptomycin, 2% L-Glut and 1 mg of puromycin. 293T (human embryonic kidney) cells were obtained from American Type Culture Collection and grown in the same growth medium as the HOS.T4.R5 cells but without the antibiotic (puromycin).

The plasmid for HIV-1BaL gp160 was a gift from Dr. Julio Martin-Garcia (Drexel University College of Medicine, Philadelphia, Pa.). pHEF-VSVG plasmid was obtained through the AIDS Research and Reference Reagent Program, Division of AIDS, NIAID, NIH from Dr. Lung-Ji Chang. 10 mM phosphate buffer was prepared using monosodium phosphate, monohydrate and disodium phosphate heptahydrate to reach pH 7.2. All other materials were obtained from Fisher Scientific.

Synthesis of KR13-Peptide Triazole Inhibitors

Figure 10:
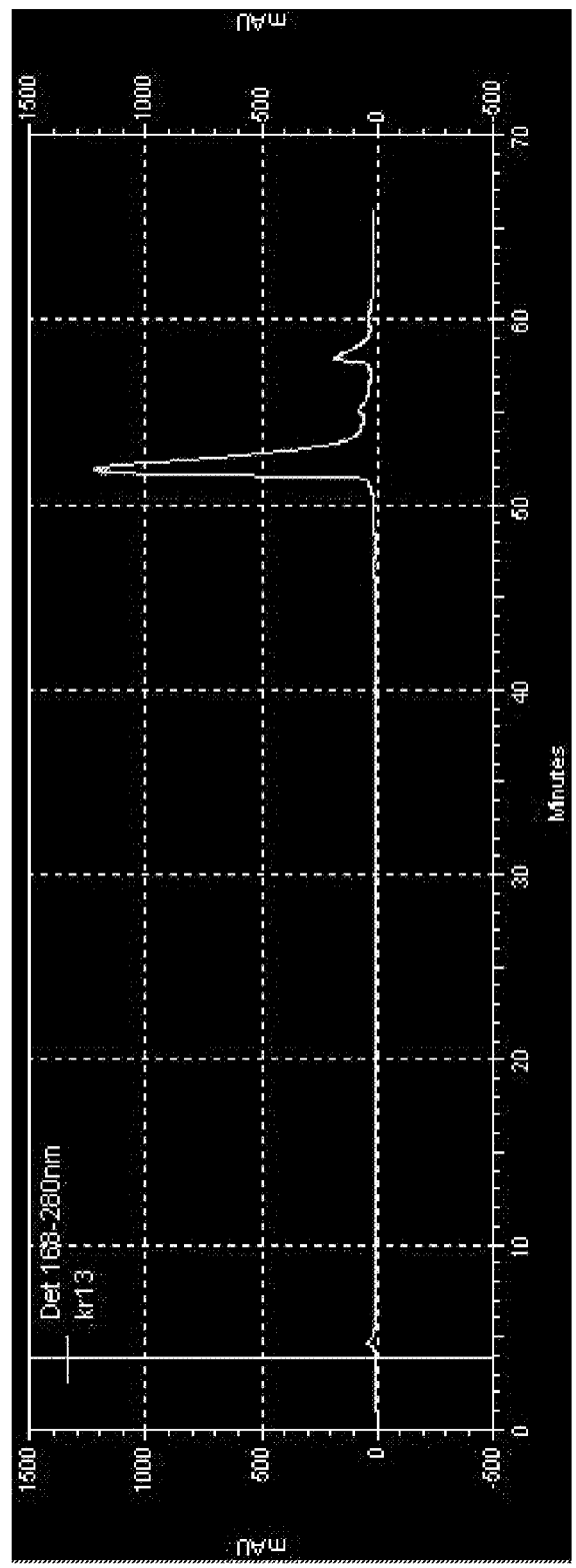
FIG. 10 is a graph illustrating the HPLC profile of KR13 (VYDAC-C18 analytical column, 5-95% acetonitrile-water in 0.1% TFA).
Figure 11:
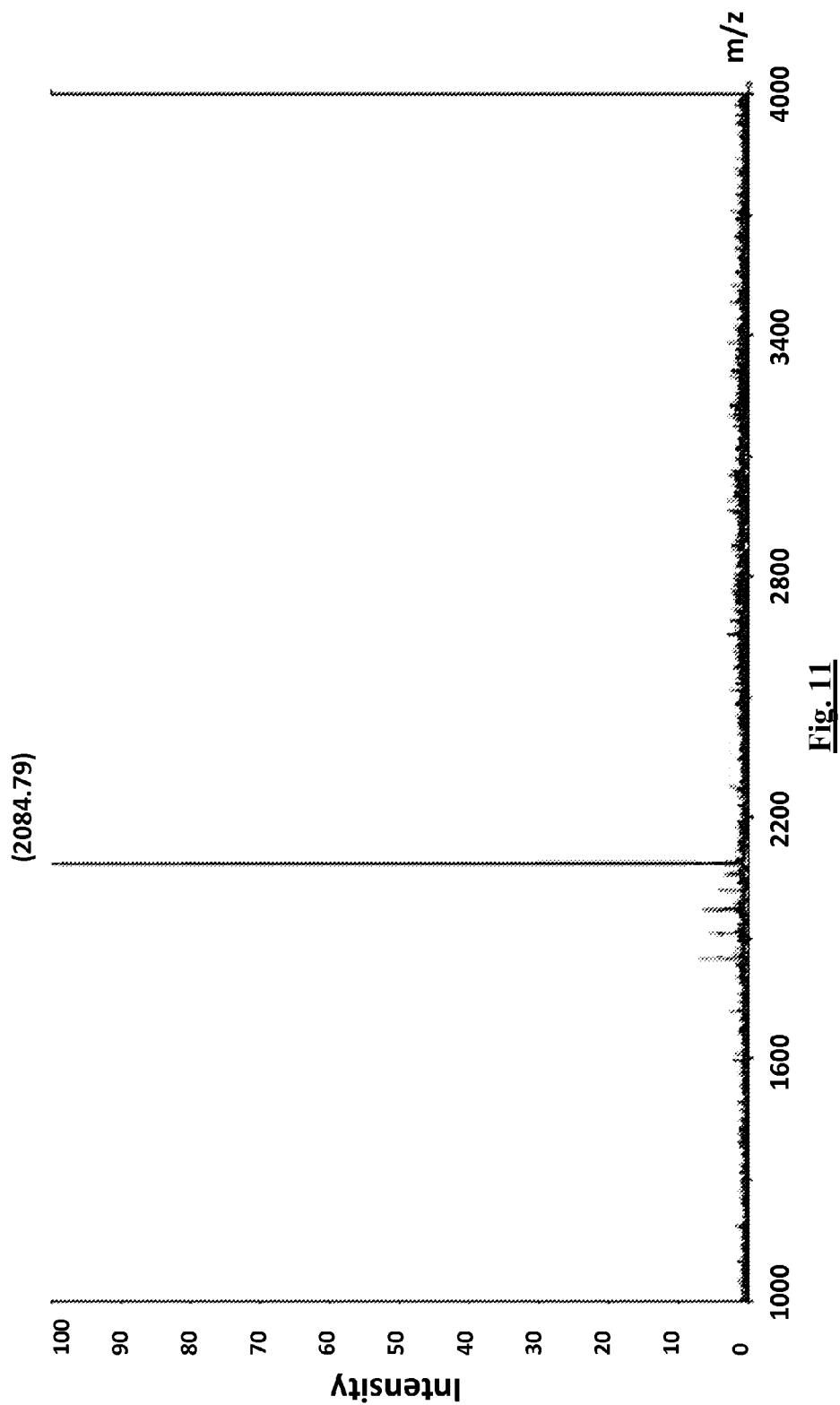
FIG. 11 illustrates the MALDI-TOF spectrum of KR13. m/z observed: 2084.79 [M+H]+($M_{cal}$=2083.5 Da) (data from Wistar Inc.).

Peptide KR13 (SEQ ID NO:2) was synthesized by manual solid phase synthesis using Fmoc chemistry on a Rink amide resin at 0.25 mmol scale. The [3+2] cycloaddition of azide and ethynylferrocene was carried out by copper-catalyzed resin method (Gopi et al., 2006, Chem Med Chem 1:54-57). Once the synthesis was complete, the peptide was removed from solid-phase resin using a cleavage cocktail mixture of 95:2:2:1 trifluoroacetic acid (TFA)/1,2-ethanedithiol/water/thioanisole for 3 hours. Crude peptide was isolated by precipitation into 20 volumes of cold ether and purified by reverse-phase HPLC (Beckmann Coulter) on a C18 column with a linear gradient of 5-95% of acetonitrile/water in 0.1% TFA (FIG. 10). The final purified peptide was confirmed by MALDI-TOF-MS, m/z of KR13: 2084.79 [M+H]+ ($M_{cal}$=2083.5 Da) (FIG. 11).

Peptide Characterization and Optical Biosensor Binding Assays

Figure 12A:
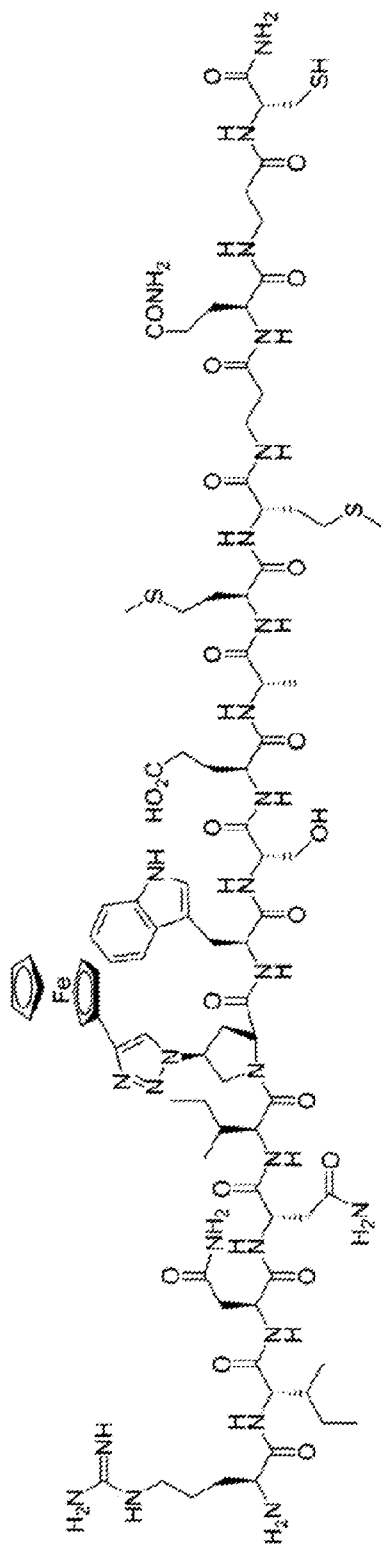
FIGS. 12A-12E illustrate the binding activity of peptide triazole KR13, and the AuNP conjugate derived from this peptide.
Figure 12B:
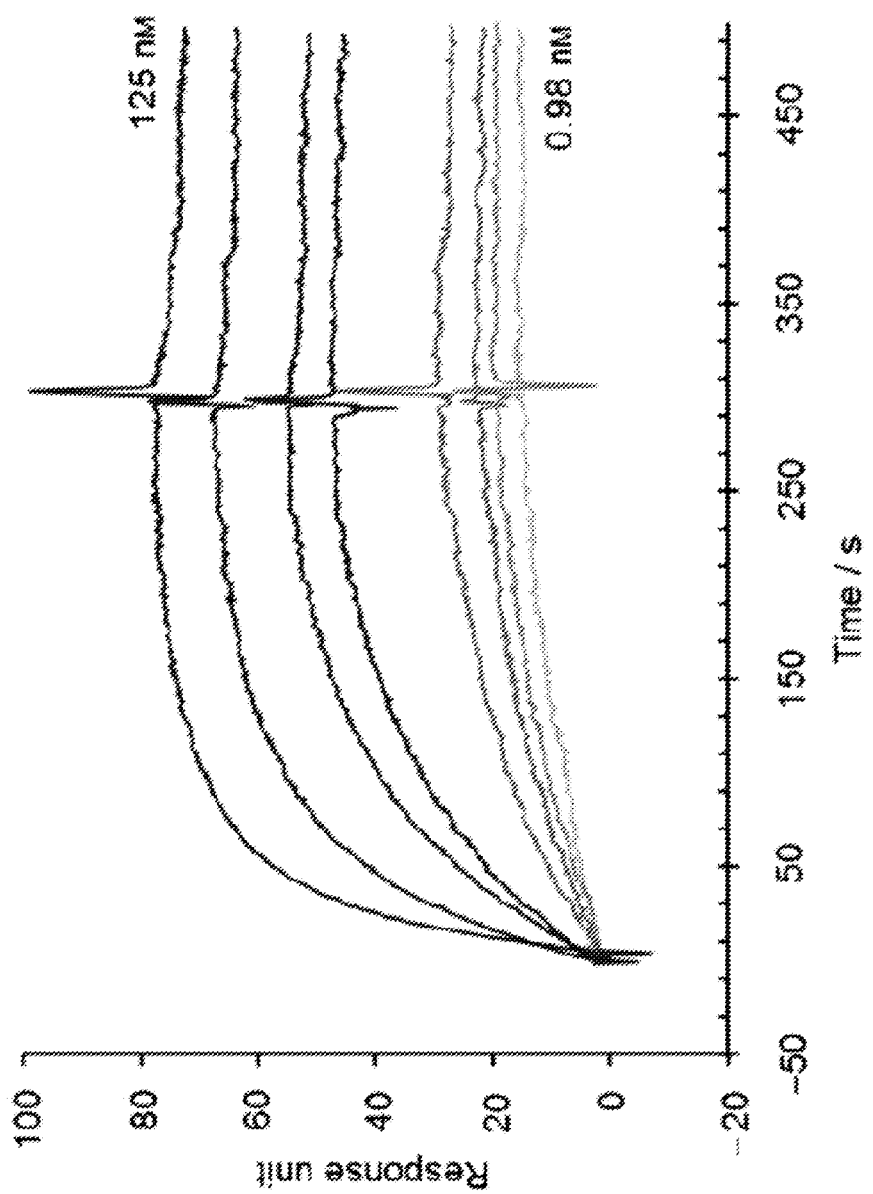
Figure 12C:
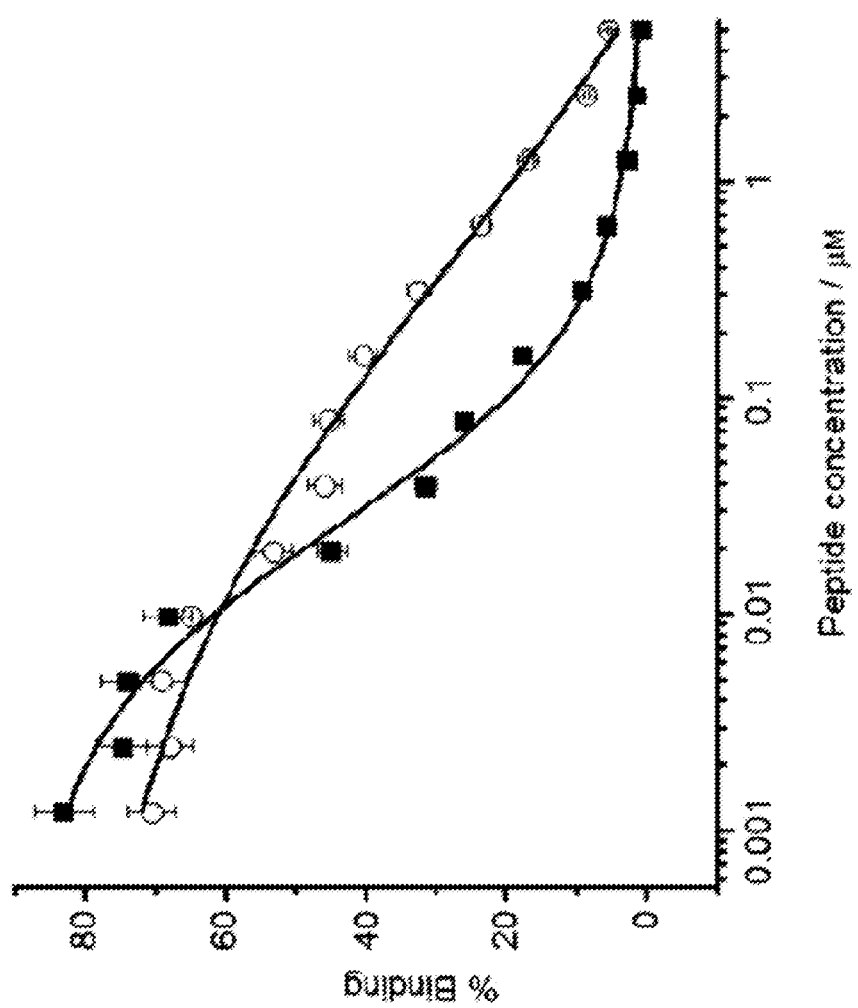

The effects of KR13 peptide on gp120 binding of sCD4 and mAb 17b were measured by competition ELISA (enzyme linked immunosorbent assay) (FIG. 12C). In a typical assay, HIV-1$_{YU-2}$ gp120 (100 ng) was immobilized on a 96-well microtiter plate overnight at 4° C., followed by three times washing with PBST buffer (1×PBS with 0.1% Tween-20 v/v), followed by blocking with 3% BSA (bovine serum albumin) in 1×PBS for 2 h. Serial dilutions of peptide (5 µM to 0.001 µM) were pre-mixed with 0.1 µg/ml sCD4, and the mixture was added to the plate in triplicate (65 µl/well) and incubated for 1 hour. The plate was washed three times with PBST followed by 1 hour incubation with biotinylated anti-CD4 antibody (65 µl/well) (eBioscience). The PBST wash step was repeated, followed by 1 hour incubation with streptavidin-bound horseradish peroxidase (AnaSpec) at 1:3000 dilution and 65 µl/well.

The above experiment was repeated using serial dilutions of peptide (5 µM to 0.001 µM) mixed with mAb 17b (protein A purified) at 0.1 µg/ml. After 1 h incubation followed by washing three times, goat-anti-human-HRP antibody (Chemcon) was added and incubated for 1 hour. The extent of HRP conjugate binding was detected in both assays by adding o-phenylenediamine (200 µL/well) (Sigma-Aldrich) reagent for 30 min, followed by measuring optical density (OD) at 450 nm using a microplate reader (Molecular Devices). All incubations were done at room temperature unless otherwise mention and the samples were loaded in triplicate.

Surface plasmon resonance (SPR) interaction analyses were performed on a Biacore 3000 optical biosensor (GE Healthcare) (FIG. 12B). The experiment was carried out at 25° C. using standard 1×PBS, pH 7.3, with 0.005% Tween-20. A CM5 sensor chip was derivatized by amine coupling by using N-ethyl-N-(3-dimethylamino-propyl)carbodiimide/N-hydroxysuccinimide1 with HIV-1$_{YU-2}$ gp120 (Fc2 cell) and as a control surface, mAb 2B6R (antibody to human IL-5 receptor α, Fc1 cell). For direct binding experiments, HIV-1$_{YU-2}$ gp120 was immobilized on the sensor surface (~5500 RU); peptide analyte in PBS buffer (concentration range of 125 nM to 0.98 nM) was passed over the surface at a flow rate of 50 µL/min, with a 5-min association phase and a 5-min dissociation phase. Regeneration of the surface was achieved by a single 5 s pulse of 10 mM glycine, pH 1.5. Data analysis was performed using BIAEvaluation 4.0 software (GE). A double reference subtraction was performed for each data set to account for non-specific binding. The steady state affinity analysis was performed by plotting data of association equilibrium value selected from 10 sec before dissociation phase for each concentration versus peptide concentration (FIG. 12B).

General Methods for Gold Nanoparticle (AuNP) Synthesis and Characterization

The citrate reduction method developed by Frens et al. (Nature 1973, 241:2) was modified in order to synthesize size-controlled stable monodispersed AuNPs.

In one embodiment, 300 µl of 1% HAuCl$_4$ was added to 30 ml of 18 µm filtered water and heated to 150° C. in an Erlenmeyer flask for 1 hour. Subsequently 700 µl, 600 µl, 500 µl, 450 µl, 400 µl of 1% citric acid was added into the flask in order to obtain 10 nm, 20 nm, 25 nm, 30 nm and 40 nm respectively. The solution was stirred vigorously for 15 min and gradually a color change was observed from light yellow to deep purple to wine red.

In another embodiment, for 20 nm AuNPs, 1% HAuCl$_4$ (300 µl) was added to 18 µm filtered water (total volume, 30 ml) and heated to 100° C. in an Erlenmeyer flask for 1 hour, followed by addition of 1% citric acid (600 µl).

Figure 12D:
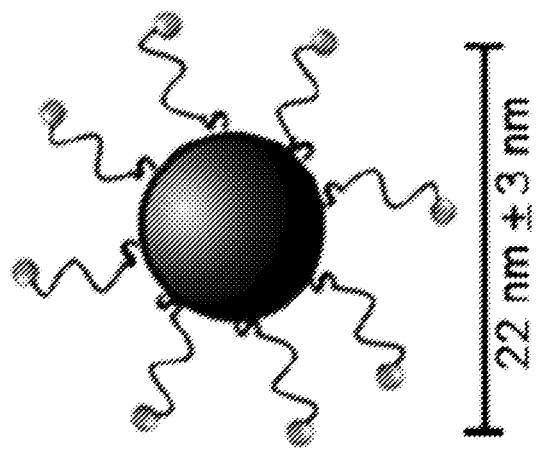
Figure 12E:
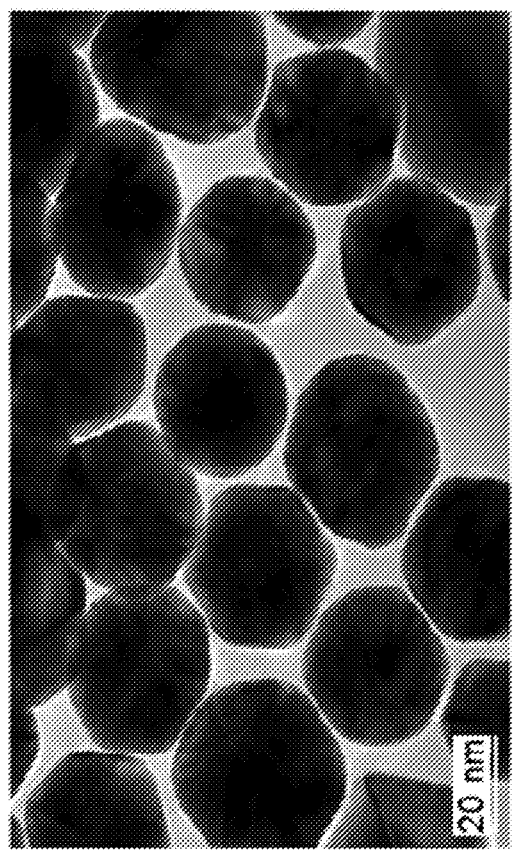

The solution was then cooled to room temperature, and BSPP (15 mg) was added into the synthesized particles (in a non-limiting embodiment, for stabilization) and stirred overnight at room temperature. The produced particles were further washed with phosphate buffer at pH 7 and concentrated using the Millipore 100,000 kDa filter. The particle size was obtained using dynamic light scattering (DLS) in the Zetasizer NS90 (Malvern Instruments), and the particle concentration was calculated using the absorbance reading at 450 nm ($A_{450}$) and at the surface plasmon resonance absorbance Aspr. This method was adopted from Haiss et al., 2007, Anal Chem 79:4215-4221. The 20 nm AuNP particle morphology was characterized using transmission electron microscopy (TEM) (FIG. 12E). Sample was prepared by adding a drop of the AuNP solution onto a carbon grid film and allowed to evaporate. TEM bright field images were taken on a JEM 2100 operated at 200 kV.

AuNP Conjugation and Validation of Stability

The peptide-nanoparticle conjugation was conducted by adding a predetermined stabilizing concentration of KR13 to the synthesized AuNP and incubating under vigorous stirring at room temperature for 30 minutes. The thiol group present in the carboxyl terminus was used for covalent linkage to the Au. The hemolytic bond energy of a thiol group to a gold surface is approximately 40 kcal·mol$^{-1}$, and the reaction that takes place is an oxidative addition of the thiol bond to the gold surface.

In one embodiment, KR13 in phosphate buffer was added dropwise into a stabilized AuNP solution, at a molar ratio of 1:1000 of peptide:AuNP. This ratio was predetermined by conducting a nanoparticle flocculation/aggregation assay. The reaction lasted for 30 minutes under vigorous stirring at room temperature in a parafilm sealed glass vial. The conjugated particles were spun down for 15 minutes at 14,000 rpm, and the pellet was resuspended in phosphate buffer. Conjugation efficiency was calculated by an absorbance difference method using the UV-spectrophotometer.

The conjugate was purified by several washes in phosphate buffer (pH 7.2) using ultracentrifugation and further filtration on a 0.2 µm filter. The conjugation efficiency was calculated using amino acid analysis of the conjugate.

Figure 8:
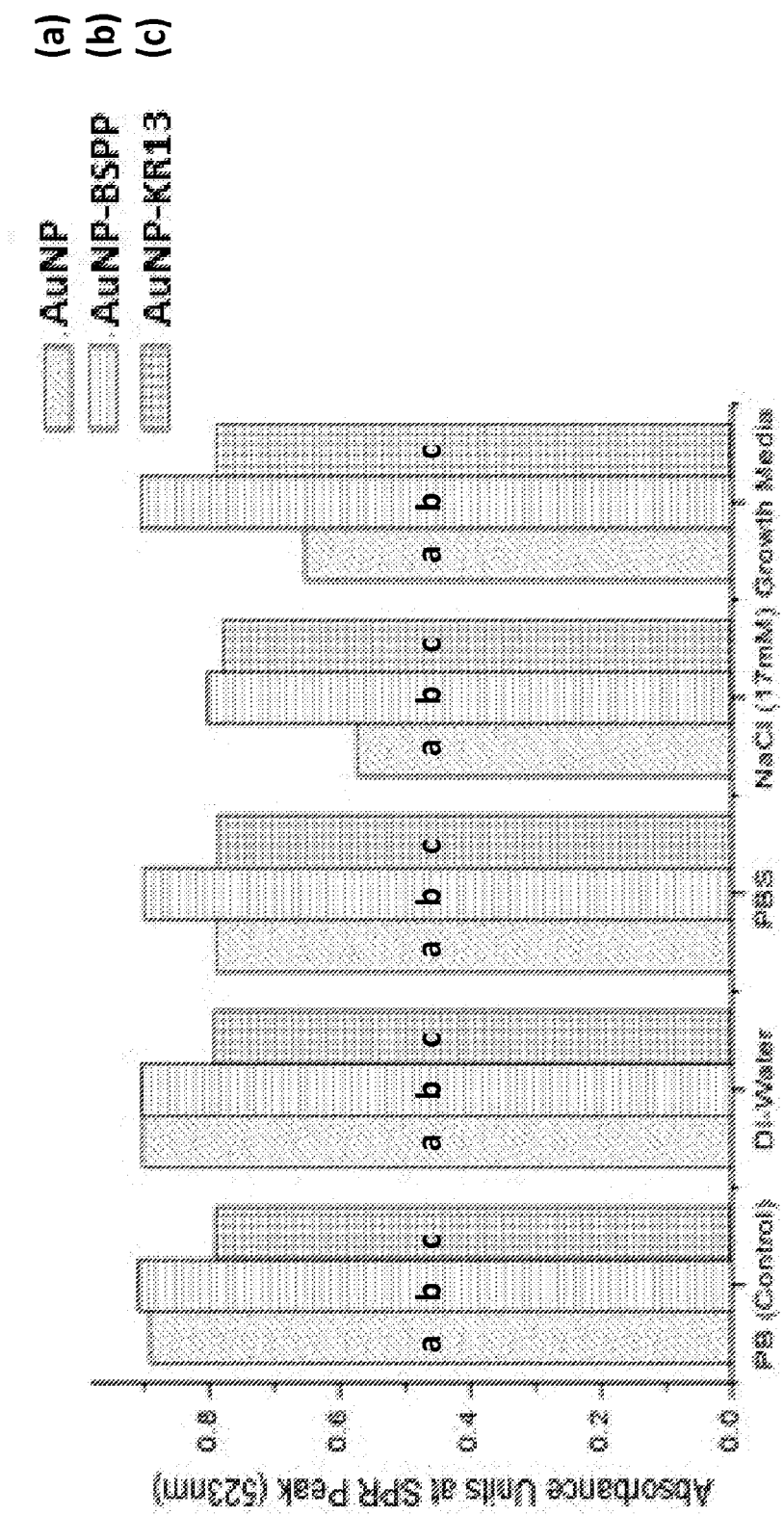
FIG. 8 is a bar graph illustrating the absorbance peaks of the AuNP, AuNP-KR13, as well as AuNP:BSPP at distinct physiological conditions, phosphate buffer (PB), DI-water, PBS, NaCl (17 mM) and HOS.T4.R5 growth media. The x-axis shows the distinct incubation buffers for the samples, and the y-axis shows the absorbance reading at SPR for the control AuNPs. Samples were incubated for 1 hour prior to reading.
Figure 9:
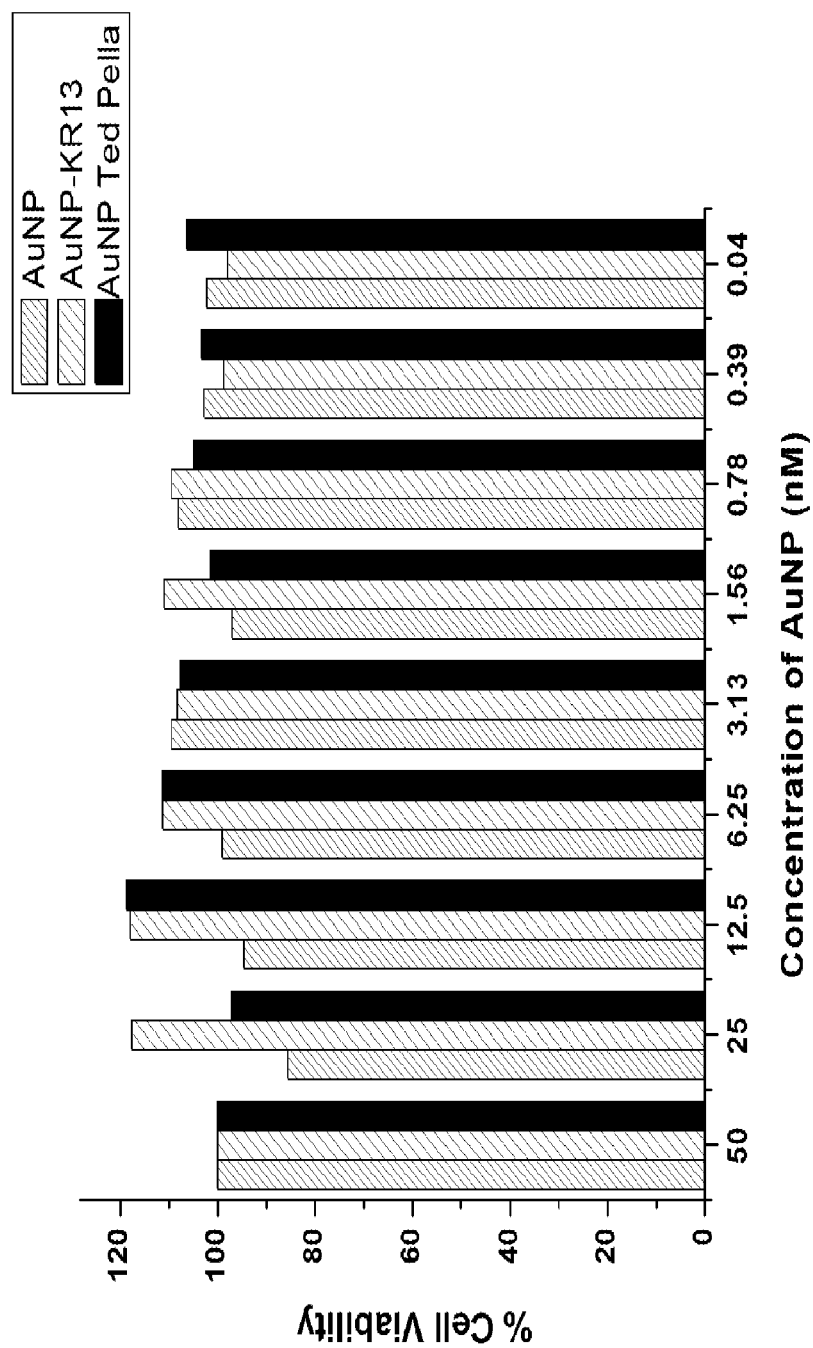
FIG. 9 is a bar graph illustrating the results of the cytotoxicity assay (WST-1) after incubation of the respective particles for 48 hours with HOS.T4.R5 cells prior to measurements. Percent (%) cell viability was calculated by using the control as 100% viability for each series. Statistical significance set at $p<0.05$ and obtained at $n=3$, $p<<0.005$.

A stability study was conducted comparing AuNP-citrate stabilized, AuNP-BSPP stabilized, as well as unstabilized AuNP-peptide conjugates (FIG. 8). All particles were incubated for 1 hour in deionized water, PBS, NaCl (17 mM), and HOS.T4.R5 cell growth media. The tests were designed to test the aggregation of the various AuNP-peptide conjugates under physiologic conditions. As a control phosphate buffer at pH 7.0 was used, and Aspr of the AuNP was measured using a UV-Vis spectrophotometer. The shift of the absorbance values suggests aggregation of the AuNP particles.

Figure 13A:
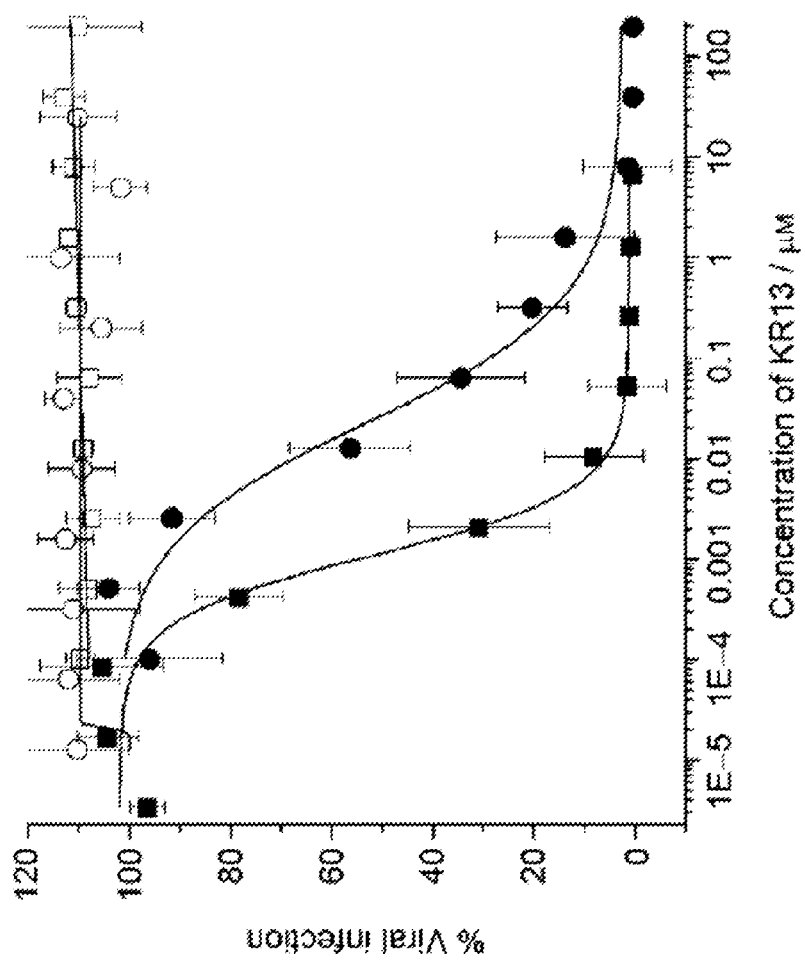
FIGS. 13A-13B illustrate inhibition of single-round cell infection by KR13 (circles) and AuNP-KR13 (squares) using the luciferase assay.
Figure 13B:
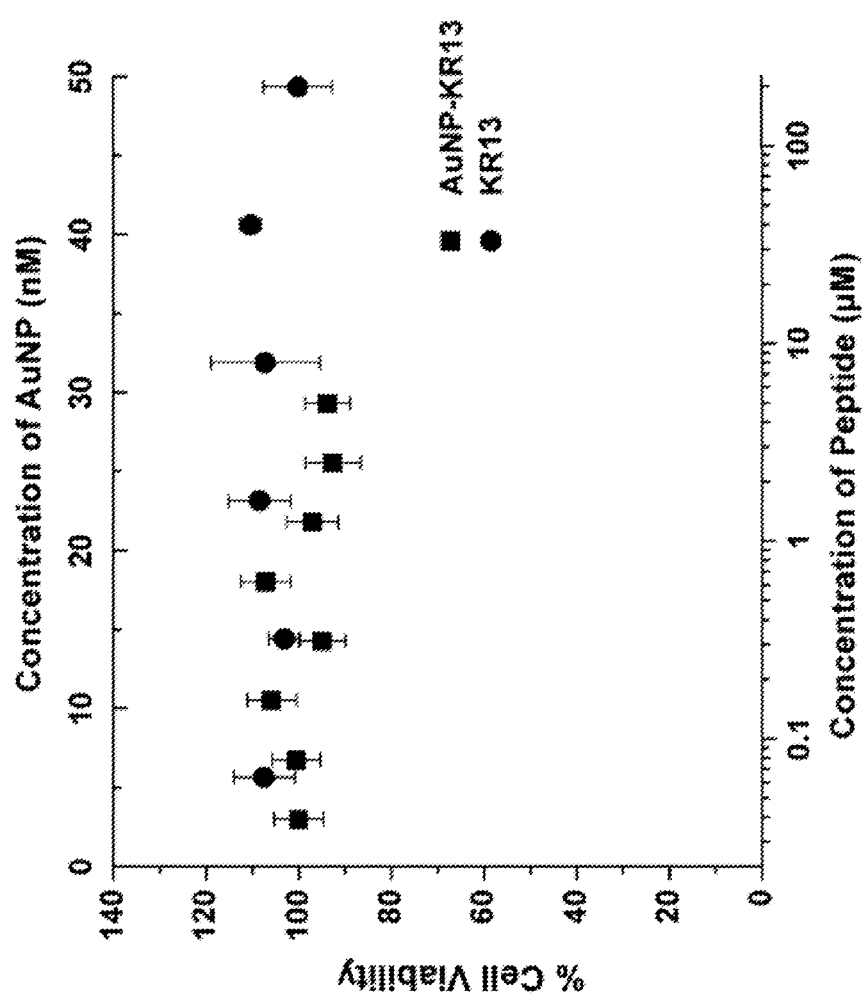

To further validate in-vitro stability, a cytotoxicity test was conducted. Modified human osteosarcoma cells (HOS.T4.R5) were seeded at 10,000 cells per well in a 96 well plate. After 24 hours, they were exposed to AuNPs, AuNP-peptide conjugates and Ted-Pella 20 nm particles (positive control), suspended in phosphate buffer at pH 7.0, at an initial concentration of 50 nM determined using UV Vis spectrometer. Toxicity was tested 48 hours post-addition using the tetrazolium salt premix reagent, WST-1 from Takara Bio Inc., following the manufacturer's protocol. The formazan product was measured using a microplate reader at 460 nm (Molecular Devices) (FIG. 13B).

Production of Single-Round Recombinant Luciferase Producing HIV-1 Virus Like Particles (VLPs)

The recombinant virus consisted of the pro-viral envelope plasmid sequence corresponding to the CCR5 targeting HIV-1BaL strain or a VSV (vesicular stomatitis virus) pseudotype, and the backbone sequence corresponded to an envelope-deficient pNL4-3-Fluc+env− provirus (Cocklin et al., 2007, J. Virol. 81:3645-3648).

Envelope DNA (4 μg) and the backbone DNA (8 μg) were co-transfected into the 293T (human embryonic kidney) cells using FuGene 6 as the transfection reagent following the manufacturer's protocol. Fourteen hours post-transfection the medium was changed, and subsequently the pseudovirus-containing medium supernatants were collected at 24 hour intervals for 72 hours. The pseudovirus-containing supernatant was cleared of cell debris by filtration using a 0.45 μm pore size filter, followed by low speed centrifugation. Purification of the pseudovirus was conducted by loading filtered cell supernatant in a Beckman UltraClear™ Tube, followed by an underlay of 20% sucrose (1 ml) cushion using a syringe. The samples were centrifuged at 30,000 rpm for 120 minutes at 4° C. (Beckman rotor SW41). The viral titers were determined by measuring viral infection on a monolayer of HOS.T4.R5 cells (modified human osteosarcoma cells (HOS.T4.R5) engineered to express CD4 and CCR5) (data not shown). The VLPs were aliquoted and stored at −80° C. until further use.

Viral Inhibition Detection Using Luciferase Reporter Assay System

In order to compare the viral inhibition caused by AuNP-KR13 conjugates to the inhibition of KR13 alone, the luciferase reporter assay was used. The infection of the VLP supernatant was predetermined using the luciferase system, and the infectious dilution of the VLP was pre-incubated with serial dilution of the inhibitor for 30 minutes at 37° C.

Modified human osteosarcoma cells engineered to express CD4 and CCR5 (HOS.T4.R5), as well as the vector for pNL4-3.Luc R-E, were provided (Connor et al., 1995, Virology 206:935-944). The recombinant virus consisted of the pro-viral envelope plasmid sequence corresponding to the CCR5 targeting HIV-$1_{BaL}$ strain and the backbone sequence corresponding to an envelope-deficient pNL4-3-Fluc+env− provirus. The single-round pseudoviral infection luciferase reporter assay was conducted as previously described (Umashankara et al., 2010, Chem Med Chem 5:1871-1879). Non-linear regression analysis with Origin V.8.1 (Origin Lab) was used to obtain the $IC_{50}$ values. All experiments were performed at least in triplicate, and results were expressed as relative infection with respect to cells infected with virus in the absence of inhibitor (100% infected).

HOS.T4.R5 cells seeded at 10,000 cells per well were incubated for 24 hours, followed by addition of the pre-incubated inhibitor-VLP complex. 48 hours post-infection the luciferase assay was used for detection. The cells were lysed by incubating with 50 μl of passive lysis buffer (Promega) per well for 5 minutes, followed by quick freeze and thaw cycles. Luciferase assays were performed using 1 mM D-luciferin salt (Anaspec) as substrate and detected on a 1450 Microbeta Liquid Scintillation and Luminescence Counter (Wallac and Jet). Non-linear regression analysis was used with Origin V.8.1 (Origin Lab) and $IC_{50}$ values were estimated. All experiments were performed at least in triplicate and results were expressed as relative infection with respect to cells infected with virus in the absence of inhibitor (100% infected).

To check the specificity of AuNP:KR13 to the HIV-1 envelope, a VSVG (vesicular stomatitis virus) pseudotype was used. VSV works through an endocytosis mechanism and has a more robust envelope than HIV-1; the inhibitors should not be actively binding to this envelope if they are indeed specific to HIV-1. The luciferase assay was conducted as explained above, and the results were read 48 hours post infection. The analysis was conducted as previously described and plotted using Origin V.8.1 (Origin Lab).

Viral Stability Assay

The stability of the VLP during the viral inhibition was tested by conducting a p24 release assay. GAG leakage of the VLP in the presence of KR13:AuNP was compared KR13 alone. This assay was conducted best mimicking the viral assay conditions above for better comparison. An equal volume of intact VLP (HIV-1Bal NL4) purified through the sucrose cushion was added to a series of samples that contained a 1:5 serial dilution of both AuNP:KR13 conjugate as well as KR13 alone at working concentrations determined from the viral assay above. As controls lysed virus (using 1% triton X followed by boiling), intact virus as well as p24 was used. All the prepared samples were incubated 30 minutes prior to clarifying spin. The supernatants were boiled with the SDS loading buffer for 5 minutes and run through a 12% SDS non-reducing polyacrylamide gel. The proteins were transferred to a Western blot in order to detect p24. Proteins were transferred to polyvinylidine diflouride membrane (Millipore, Billerica, Mass.), and detected using an anti-rabbit p24 antibody and an anti-rabbit IGg HRP secondary antibody.

Figure 7:
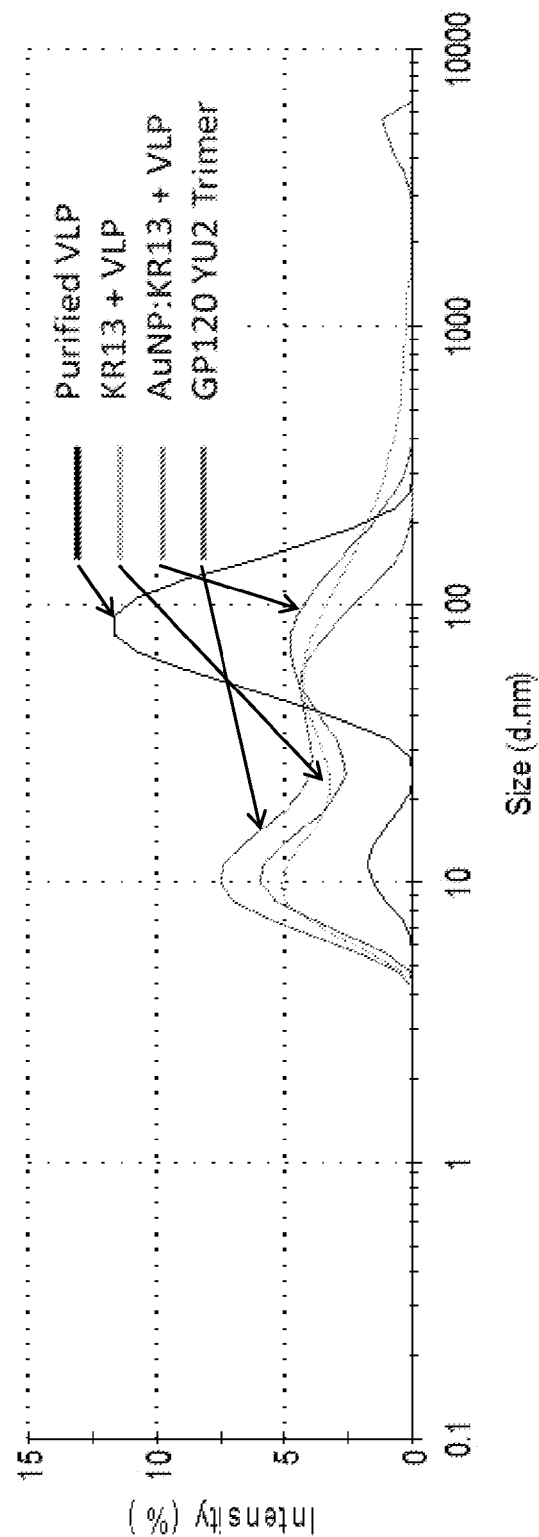
FIG. 7 illustrates the DLS measurements of purified virus like particle (VLP), with KR13 as well as AuNP:KR13 conjugate. The inhibitor and the VLP were incubated for 30 minutes prior to spin down.

To validate the results the stability of the VLP was also tested using DLS. In order to check whether addition of inhibitor leads to viral disruption and hence change in diameter of the virus. As controls, intact purified VLP as well as YU2 GP120 trimer was used. The inhibitor and VLP were incubated for 30 minutes prior to diameter testing using DLS (FIG. 7).

p24 Release Assay

Figure 16A:
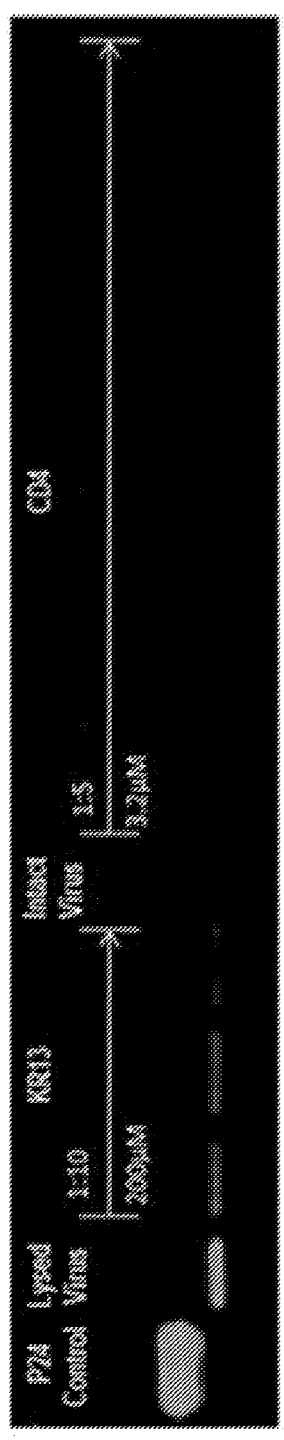
FIGS. 16A-16C illustrate Western blot gel images showing p24 release as a function of dose of (FIG. 16A) sCD4 and (FIG. 16B) HNG156 from HIV-1BaL envelope pseudovirus.
Figure 16B:
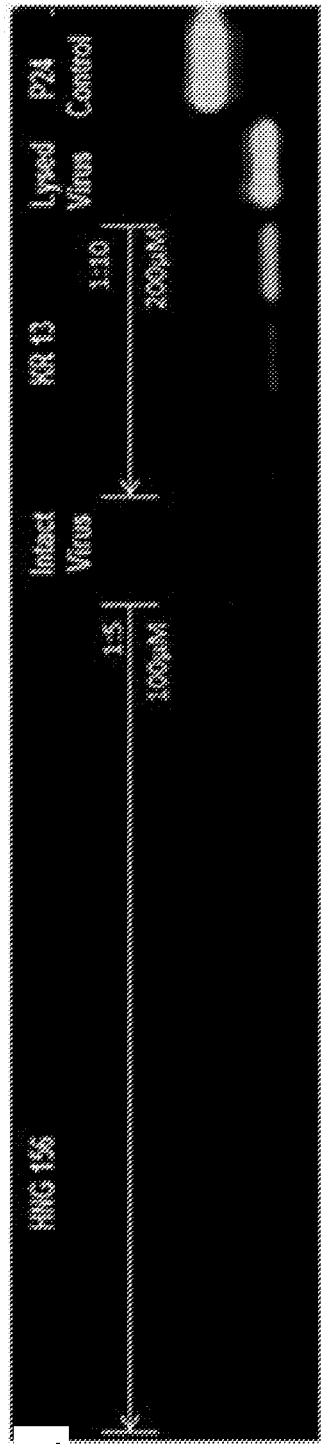

Two sets of p24 release assay experiments were conducted. First, in order to compare the virucidal effect of KR13 and AuNP-KR13 conjugate to other ligands, cell-free p24 release from the virion in the presence of sCD4 and HNG156 were conducted (FIGS. 16A-16B). Further, the specificity of the virucidal effect was characterized by conducting p24 release assay using pseudovirus with VSV-G envelope with the same backbone as the HIV-1BaL strain (FIG. 16C).

The stability of the VLP during the viral inhibition by KR13 and AuNP-KR13 was compared using a p24 release assay, conducted under conditions to best mimic the viral assay conditions. An equal volume of intact VLP (HIV-$1_{BaL}$), purified through the sucrose cushion, was added to a series of samples that contained a 1:5 serial dilution of both AuNP-KR13 conjugates and KR13 alone at working concentrations determined from the viral assay above. Lysed virus (using 1% Triton X-100 followed by heating at 95° C.), intact virus as well as p24 protein were used as controls. The inhibitor was incubated with purified virus for 30 minutes followed by a 2-hour centrifugation at 4° C. and 13,200 rpm (Eppendorf Centrifuge 5415R). The supernant was collected, and the p24 content was quantified by Western blot analysis using the LiCor IR detection system (Experimental Section). Rabbit anti-p24 (abcam) and goat anti-rabbit IgG conjugated with IRDye® 800CW (LiCor Biosciences) were used as the primary and secondary antibodies respectively. Lysed virus controls were prepared by heating the virus with 1% Triton X-100 for 5 minutes at 95° C. followed by supernatant collection as the test samples. Further, all the gels had a KR13 control that had three serial dilution of KR13 treated with the same HIV-$1_{BaL}$ strain of purified pseudovirus. Image J software tool was used in order to quantify the band intensities.

Figure 16C:
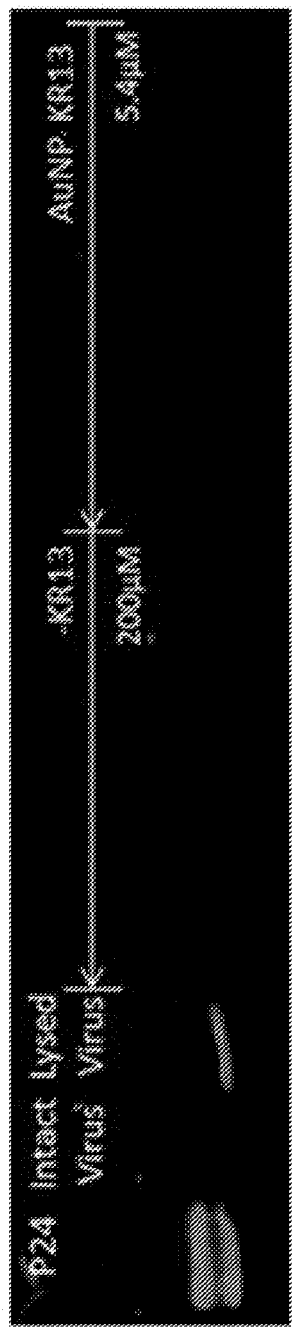

FIGS. 16A-16C illustrate data with serial dilutions of the inhibitor incubated with HIV-1BaL or VSV-G pseudovirus, followed by Western blot analysis as described elsewhere herein. The results demonstrated that neither HNG156 nor sCD4 led to any p24 release even at the highest concentrations used. Further, the VSV-G control experiment, which was conducted using inhibitors KR13 and AuNP-KR13, did not show any p24 leakage.

Example 1

AuNP Synthesis and Conjugation with KR13

The peptide triazole denoted KR13 (FIG. 12A), containing a Cys-SH group, was synthesized. In one embodiment, this cysteine-containing derivative was selected because the introduced SH group facilitates conjugation to the AuNP carriers. In addition, the extension contained β-Ala residues for spacing and a Gln residue for potential side chain modifications.

KR13 was prepared by manual solid phase synthesis using Fmoc chemistry on a Rink amide resin at 0.25 mmol scale (Gopi et al., 2006, Chem Med Chem 1:54-57). The amino acid sequence of KR13 is RINNIXWSEAMMβAQβAC-NH$_2$, where X is ferrocenyltriazole-Pro. The ferrocenyl group was found in earlier studies (Gopi et al., 2006, Chem Med Chem 1:54-57; Gopi et al., 2008, J. Med. Chem. 51:2638-2647) to lead to optimized peptide triazole potency and was retained here to evaluate the impact of multivalency with this high-efficacy derivative.

Direct binding of the peptide triazole to immobilized HIV-1$_{YU2}$gp120 was measured as previously described (Gopi et al., 2006, Chem Med Chem 1:54-57) using surface plasmon resonance (SPR) with a Biacore 3000 optical biosensor (GE Healthcare). Steady state analysis was conducted using the method of Morton and coworkers (Myszka et al., 1998, Biophys. J. 75:583-594; Morton et al., 1994, J. Mol. Recogn. 7:47-55) (FIG. 12B). KR13 activity was characterized by testing competitive inhibition of soluble CD4 and mAb 17b binding to HIV-1$_{YU2}$gp120 through Enzyme Linked Immunosorbent Assay (ELISA). The molecular interaction analyses showed that HNG156 analog (KR13) retained high affinity gp120 binding (FIG. 12B) and the dual receptor site competition (FIG. 12C) functions of HNG156 (Gopi et al., 2008, J. Med. Chem. 51:2638-2647; Gopi et al., 2009, J. Mol. Recogn. 22:169-174).

Multivalent gold nanoparticle (AuNP) conjugates of KR13 were prepared (FIG. 12D) to test the possibility of enhanced antiviral activity by nanoconjugates. The AuNPs were synthesized using a modified citrate reduction method to obtain size-controlled, stable and monodisperse AuNPs (Frens, 1973, Nature (London), Phys. Sci 241(2):20-22). Characterization of these particles was conducted using UV-Vis spectroscopy, dynamic light scattering (DLS) and transmission electron microscopy (TEM). The controlled size distribution afforded particles with average particle size ±4 nm. The method allowed easy particle size alteration by changing citric acid concentration. The particles were stabilized using phosphine compounds.

Figure 2:
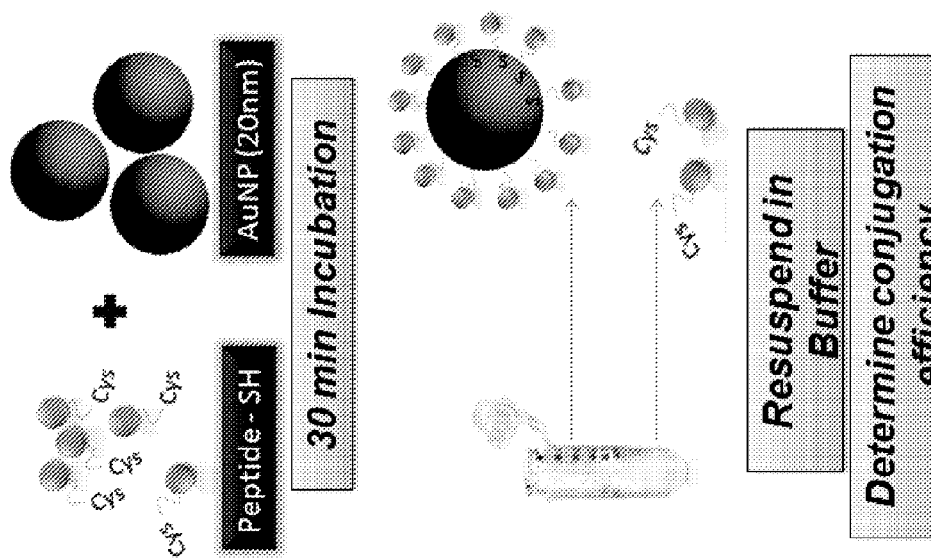
FIG. 2 illustrates the conjugation of peptides to a gold nanoparticle.
Figure 3:
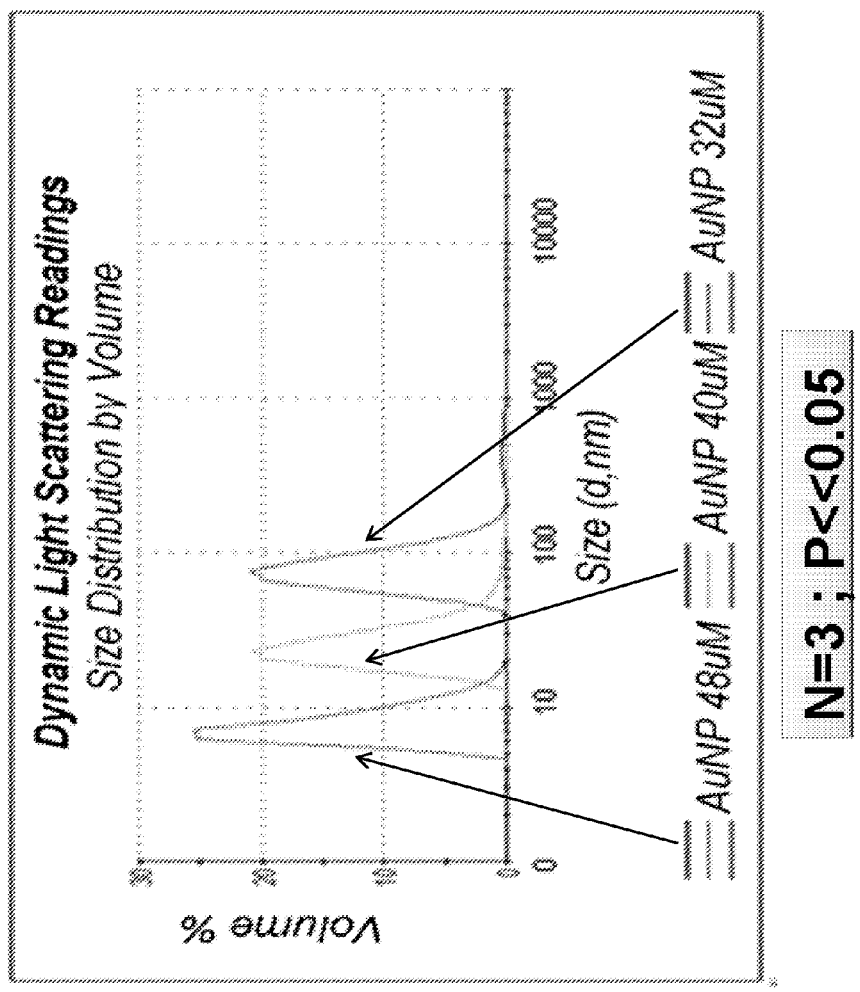
FIG. 3 illustrates dynamic light scattering readings.

The peptide (KR13) was conjugated to the AuNP using a direct gold-thiol covalent link by incubating the peptide and AuNP at room temperature for 30 minutes. The ratio of KR13:AuNP was pre-determined by conducting a flocculation/aggregation assay using 10% NaCl. Further, the conjugation efficiency was calculated after each wash during filtration of the product using indirect absorbance measurements. FIG. 2 illustrates the conjugation schematic.

The AuNP-KR13 was purified by filtration and ultracentrifugation, and the extent of peptide triazole conjugation on AuNPs was determined using amino acid analysis. The size and extent of polydispersity of the AuNP-KR13 conjugates were measured using Transmission Electron Microscopy (TEM) with a JEM 2100 operated at 200 kV, and Dynamic Light Scattering (DLS) with a Zetasizer NS90 (Malvern Instruments). The TEM image is shown in FIG. 12E. The sizes of the synthesized AuNPs using various concentration of citric acid were compared using the DLS to the expected calculated sizes (control) as well as the AuNPs synthesized (Frens, 1973, Nature (London), Phys. Sci 241(2):20-22). TEM image of the 20 nm particles were also taken for further validation of the size controlled synthesis, and showed very narrow distribution.

Example 2

Validation of AuNP-KR13 Stability and Cytotoxicity

The stability of AuNP-KR13 conjugates at physiologic conditions was determined by testing their aggregation at conditions mimicking physiologic environment. The study was conducted in media and included incubation at 37° C. Gold nanoparticles in phosphate buffer at pH 7.0 (where agglomeration is known to occur) served as the positive control. Particle aggregation was indicated when there was a shift in the absorbance at surface plasmon resonance ($A_{spr}$) of the 20 nm stabilized gold nanoparticles. No aggregation was observed for the BSPP stabilized gold-peptide stabilized particle respectively under all the conditions including high salt concentration (NaCl 17 mM). Unstabilized AuNPs did show aggregation under high salt concentrations and hence are not stable (FIG. 8).

Figure 4:
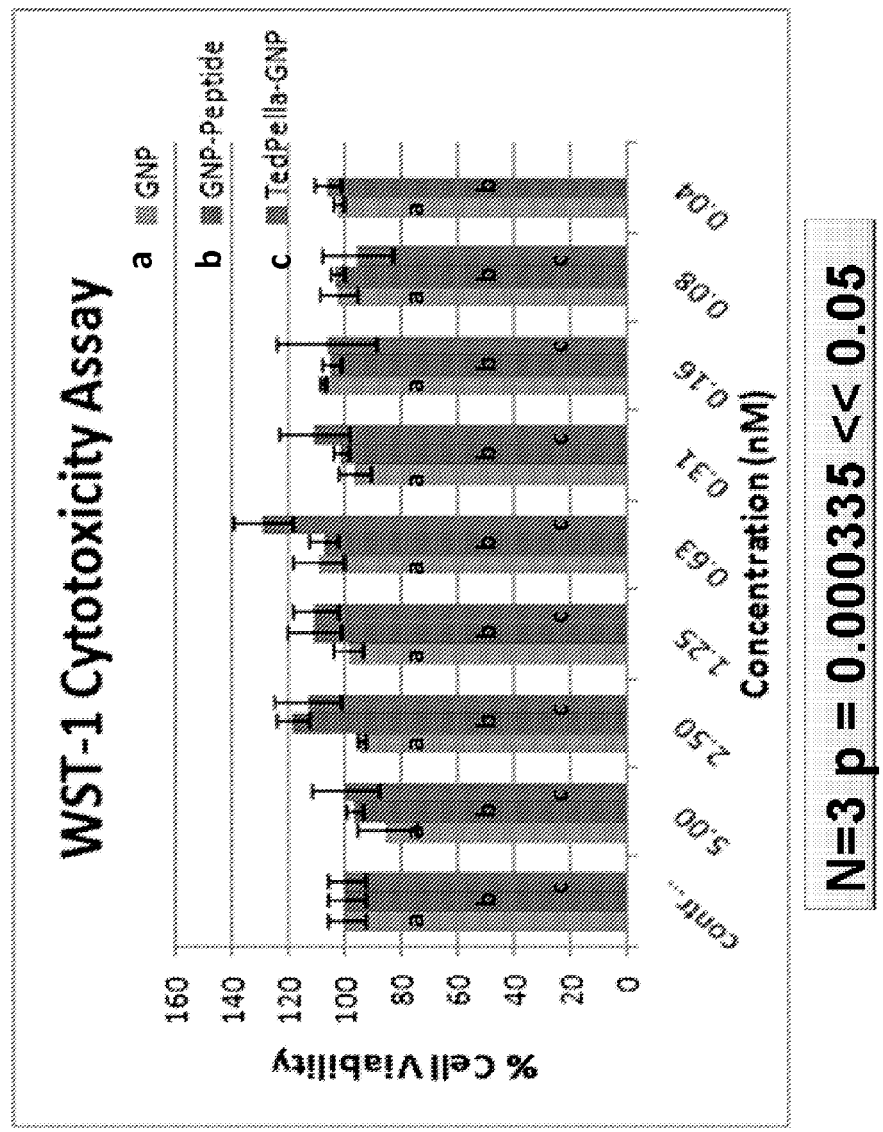
FIG. 4 is a bar graph illustrating WST-1 cytotoxicity assay results.
Figure 5:
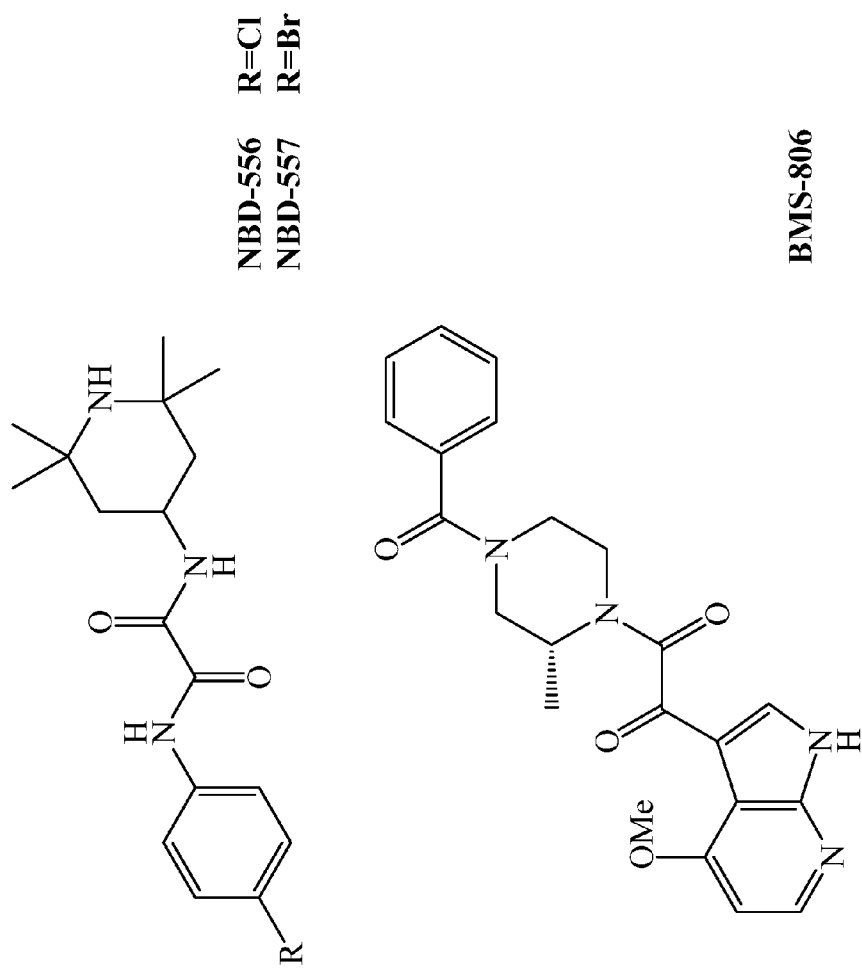
FIG. 5 illustrates the structure of compounds NBD-556, NBD-557 and BMS-806.

Cytotoxicity tests were conducted using the Takara WST-1 premix, which is a tetrazolium salt (WST-1) cleaved to a soluble formazan dye by the succinate-tetrazolium reductases (present in the mitochondrial respiratory chain and active only in viable cells). Therefore, the formazan dye detected using the Microplate reader at 460 nm directly correlates to the number of metabolically active cells. Results from cytotoxicity tests performed 48 hours prior to addition of the particles are shown in FIG. 4. Commercially available 20 nm AuNPs are used as control (Ted Pella Inc.). These results suggested that both AuNP as well as AuNP-KR13 conjugates had no significant difference from the control Ted Pella AuNP and hence the AuNPs were not cytotoxic to the HOS.T4.R5 cells.

Example 3

Viral Inhibition Detection Using Luciferase Reporter Assay

The HIV-1 viral entry inhibition potencies of KR13 and AuNP-KR13 conjugates were compared using a single-round pseudoviral infection luciferase reporter assay as previously described (Umashankara et al., 2010, Chem Med Chem 5:1871-1879). The profiles for inhibition of infection of modified human osteosarcoma cells (HOS.T4.R5) engineered to express CD4 and CCR5 receptor and co-receptor respectively by pseudotyped HIV-1$_{BaL}$ are illustrated in FIGS. 13A-13B. Compared to peptide triazole alone, the AuNP-KR13 conjugate exhibited a close to 25-fold enhancement of infection inhibition activity, IC$_{50}$ values were 23±6 nM and 1±0.1 nM, respectively, for KR13 alone and AuNP-KR13 conjugate. The lack of inhibition of cell infection by control VSV-G pseudotype virus (FIG. 13A) shows that the viral inhibitions of both KR13 and AuNP-KR13 are specific for HIV-1 envelope. No significant cytotoxicity was observed for either KR13 or AuNP-KR13 (FIG. 13B).

Further to demonstrate the specificity of the AuNP: KR13 conjugate, VSV control was used for the viral assay. Western blot analysis was used to test for viral disruption. HIV-$1_{BAL\_NL4}$ pseudotype virus was used for this study at working dilution. VLP and inhibitor were incubated for 30 minutes at 37° C. Clarifying spin was conducted prior to gel transfer. The primary antibody was sheep anti-gp120 antibody (D7324) and the secondary antibody was anti-sheep—HRP.

FIGS. 13A-13B illustrate the plot obtained from the VSV control assay, which was conducted in the same way as the inhibitory assay. There was no statistically significant difference in the percentage infected even at the highest concentration of the inhibitor. This clearly showed that both KR13 as well as the AuNP:KR13 conjugate were specific binders to the gp120 envelope, and hence in the future can be used a microbicide that targets the gp120 envelop specifically.

Figure 6:
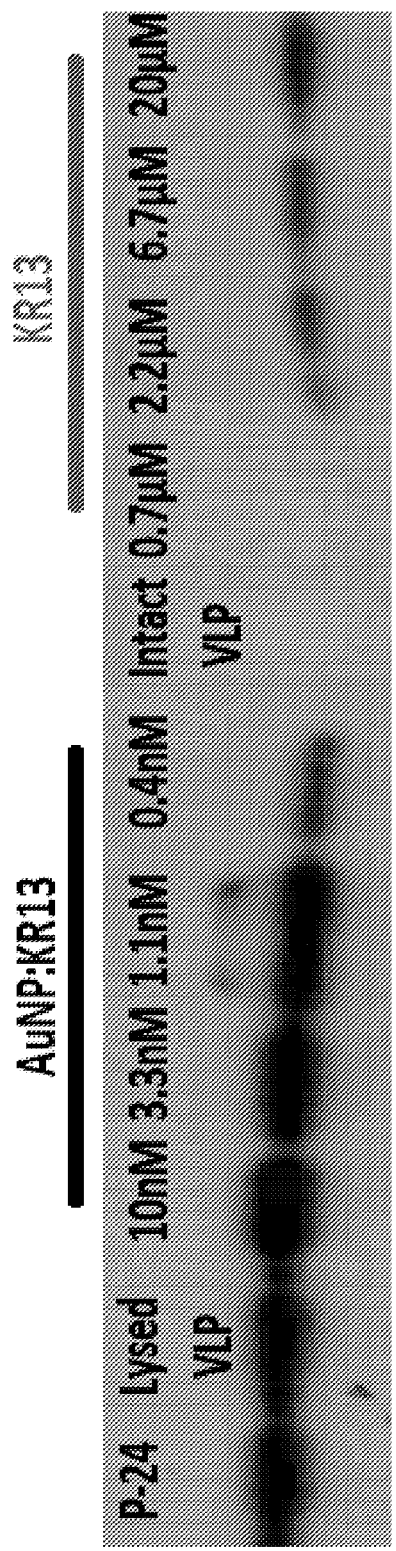
FIG. 6 illustrates the Western blot that indicates p24 release from the intact VLP upon addition of the KR13 as well as the AuNP:KR13 conjugate. The VLP and the inhibitor were incubated for 30 min at 37° C. As a positive control, the VLP was lysed using 1% Triton X and boiled at 100° C.

FIG. 6 illustrates the shedding analysis, as evaluated using the densitometry protocol from Image J after calibration. The inset showed the Western blot itself from which the densitometry was done. It was clearly seen that the lysed virus has the maximum amount of gp120 shedding and hence serves as a positive control. While the intact virus still does have some shedding, the AuNP:KR13 did show an increase in shedding compared to the KR13 alone. However, both these inhibitors did not completely shed the viral envelop.

FIG. 7 illustrates the validation of the viral instability caused by the inhibitor using DLS. The intact virus was approximately 90-100 nm showing consistency. Both KR13 and AuNP:KR13 showed viral disruption, which was observed by the drop in the peak at approximately 90-100 nm and a rise in the peak at 10-14 nm, which is matching with the GP120-YU2 trimer peak.

Example 4

Further Characterization of the AuNP Conjugate

The effects of KR13 and AuNP-KR13 on the virus particle itself were evaluated by measuring release of the nucleocapsid protein p24. This was done to understand the effects of the inhibitors on the virus in the earliest stages of HIV-1 infection. Capsid protein release from virus pseudoparticles was detected by incubating the inhibitor with purified pseudovirus for 30 minutes at 37° C., followed by detection of release of p24 in the supernatant using Western blot analysis with an Odyssey Infrared Imaging System (Li-Cor). For this p24 release analysis, the positive control was 1% Triton X-100 detergent-lysed pseudovirus, and the negative control was mock treated intact virus. Western blot analyses (FIG. 14A) revealed concentration-dependent p24 release by both KR13 and AuNP-KR13. Quantitation of p24 band intensities, obtained with Image J software, enabled assessment of $IC_{50}$ values (FIG. 14B) and showed that the hierarchy of disruption potencies was similar to that found (FIGS. 13A-13B) for inhibition of cell infection. The absolute $IC_{50}$ values, obtained for p24 release dose response data fitted using Origin Pro 8, were 866±55 nM and 15.6±2 nM, respectively, for KR13 and AuNP-KR13.

A similar relationship of potency enhancement was observed in the pseudoviral infectivity assay (FIGS. 13A-13B). p24 release induced by KR13 and AuNP-KR13 was specific to the interaction of the peptide with HIV-1 gp120 by showing no effect with VSV-G pseudotyped virus.

Figure 14A:
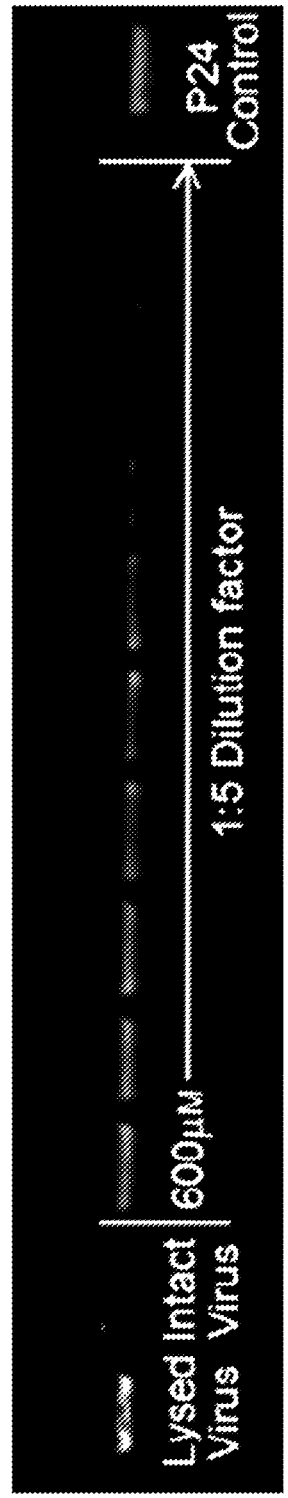
FIGS. 14A-14C illustrate Gag p24 release from HIV1BaL pseudotype virus caused by KR13 and AuNP-KR13. Western blot gel images illustrate p24 release as a function of dose of (FIG. 14A) KR13 alone and (FIG. 14B) AuNP-KR13. Controls shown are lysed virus (treated with 1% Triton X-100), intact virus (no treatments), and p24 control (5 μL of 20 μg·mL⁻¹). The highest concentration of KR13 in both cases is indicated, with subsequent lanes corresponding to sequential 1:5-fold dilutions indicated by arrows.
Figure 14B:
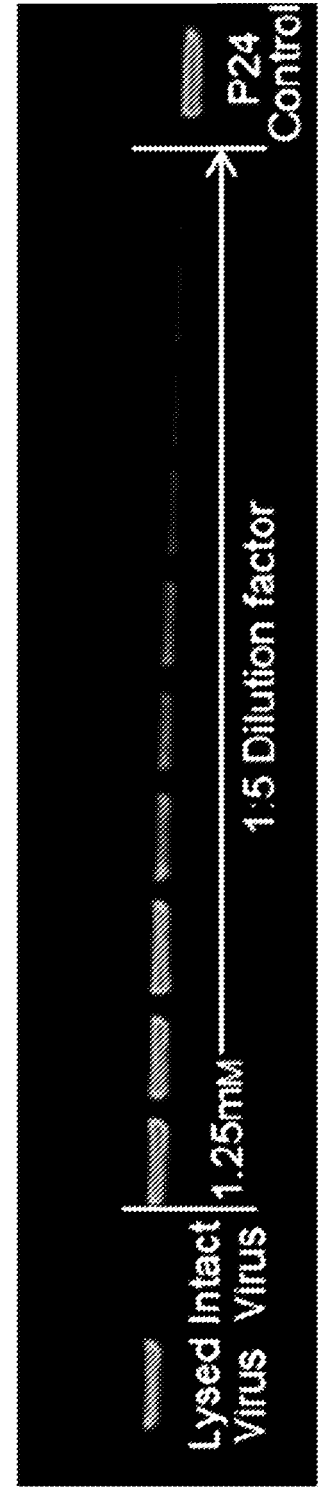
Figure 14C:
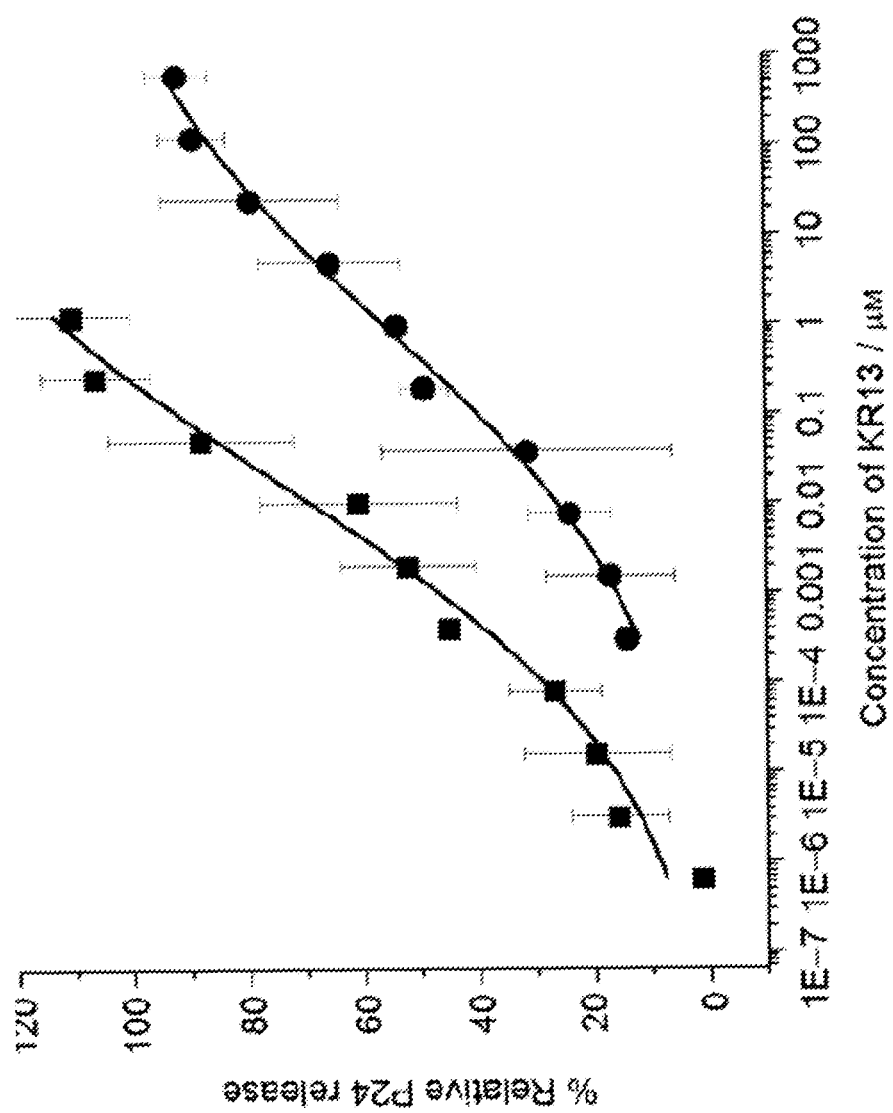
Figures 15A, 15B:
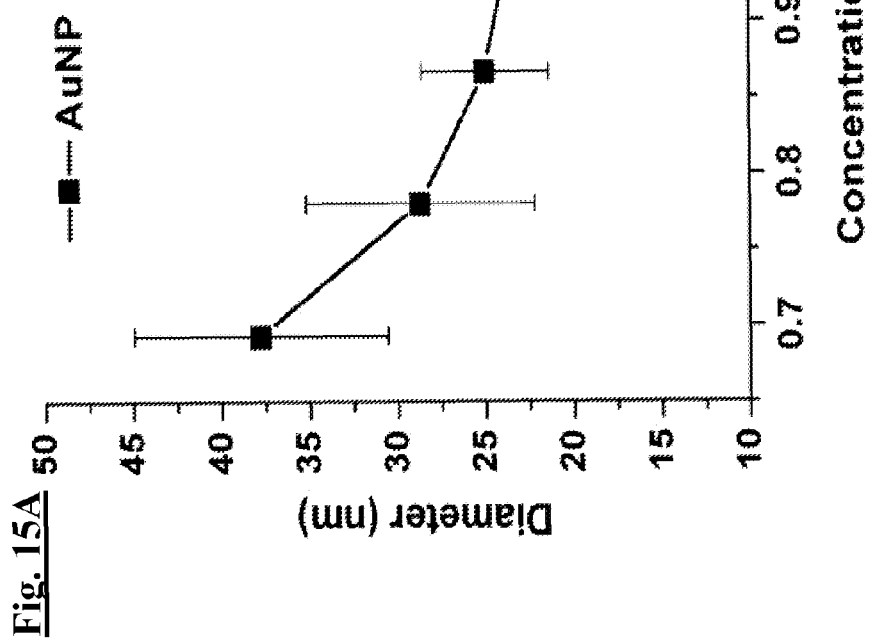
FIGS. 15A-15B illustrate dynamic light scattering (DLS) results.

The current study has established that modified peptide triazoles, which inhibit cell infection by HIV-1 pseudoviruses, are also capable of disrupting virus particles in the absence of cells. Results from p24 analysis of treated pseudotyped viruses demonstrated that the intra-virion capsid protein was indeed released in a dose dependent manner by the peptide triazole KR13 (FIG. 14A). This release was enhanced by multivalent display of KR13 on gold nanoparticles (FIG. 14B). Furthermore, the magnitudes of dose responses of p24 release by the free peptide and AuNP-KR13 had a similar trend (AuNP-KR13>>KR13) to that observed for inhibition of cell infection by these compounds (FIG. 14C). Hence, cell-independent virus particle disruption may be at least part of the mechanism of inhibition of cell infection exhibited by the modified peptide triazoles tested. However, for inhibitors that cause rupture, the relative importance of virus rupture and direct receptor binding inhibition in the overall antiviral effect is yet to be determined. Furthermore, at this stage, the physical mechanism by which the virus particle is disrupted to release p24 may not be defined. In preliminary dynamic light scattering analysis, peptide-treated pseudovirus preparations appear to have reduced diameter, which could indicate either virion collapse or fragmentation.

The results suggest that the inhibition potency of the peptide-triazole inhibitor is enhanced by conjugating them to AuNPs and making them multivalent. It is possible that there is a higher local concentration of the peptide available at a particular viral envelop available for binding. The amino acid analysis conducted on the AuNP:KR13 suggests that the KR13/AuNP ratio is 1:72. Therefore, there are approximately 100 peptides surrounding one 20 nm sized AuNP; in comparison the diameter of a single viral envelop spike is approximately determined to be 14 nm. It is also theorized that the virion has the spikes organized in an icosahedral symmetry. Therefore, through ultrastructural studies an intact virus particle should have approximately 72 spikes, and, if assuming the structure of the AuNP is a perfect sphere, the maximum number of KR13 peptide facing an individual viral particle can be estimated to be 115 per monomer. The assumptions made are that 50% of the spikes are facing out and also there are a total of 1000 KR13 peptides around one AuNP. This calculation therefore suggests that this system creates a high local concentration of the peptide.

The viral efficacy is reduced as seen from the gp120 shredding assay (FIG. 6B) when both AuNP: KR13 as well as KR13 is introduced. Without wishing to be limited by theory, this may happen due to the disruption of the metastable virus. This effect is clearly enhanced when using the AuNP conjugate because of its structural integrity as well as large surface area. Since AuNP has also a strong chemical stability, it may act as a steric stabilizer of the viral envelope. The strong structural backbone of the conjugate, along with more KR13 on one spike, may lead to a much more increased viral envelop disruption and eventually inactivation of the virus. The anti-viral potency enhancement caused by this multivalent conjugate (FIGS. 13A-13B) may be brought about by a combination of the high local concentration of ligand as well as the structural rigidity provided by the gold NP of the AuNP conjugate, leading to a much better virucide.

The inhibitory potency can be potentially further enhanced by alteration of the conjugation chemistry. For example, one could increase the size of the conjugate, leading to a larger and more active AuNP (due to the increased number of KR13 surface area coverage). In one embodiment, the diameter should not be >120 nm, since the diameter of the HIV-1 virus is approximately 120 nm including the envelope. Also, further increase in size of the AuNP above that of the HIV-1 viral diameter might lead as better inhibition, but this large size might cause some cytotoxicity to the cells in vitro due to gravitational settling. Another approach would be to space out the peptide on the AuNP, leading to much lower local steric hindrance, and hence a much more efficient inhibitor composition. It could be important to investigate the mechanism by which these multivalent inhibitors act on the virus leading to its inhibition. Hence, it could be relevant to understand the time-dependent disruption of the viral envelop by these multivalent conjugates, as well as the leakage of Gag proteins from the viral core (p24, p17 and p2'7). Since the AuNPs have an optical visualization characteristic, they have an advantage compared to other multivalent compositions: visual tracking of the virus on cell surface using dark field microscopy. Overall this composition not only represents an entire class of multivalent-virucides targeting the viral envelope but also disrupts the virus before binding to cell receptor (CD4). Hence this composition has great potential as a candidate for HAART.

In one aspect, the methods disclosed herein allowed the size controlled synthesis of AuNPs with narrow size distribution and the successful syntheses of non-toxic AuNP-peptide conjugates with known coverage and stable in physiological conditions. Pseudoviral infection assay in vitro showed that these conjugates have approximately 25 fold increase in inhibition of viral entry compared to peptide alone. Pseudoviral disruption study showed that the AuNP/KR13 conjugate not only increased the peptide potency but also led to disruption of the virus, allowing for faster inactivation of the virus.

Cell-free virucidal action by peptide triazole variants has significant implications for the potential uses of this type of inhibitor in AIDS prevention and treatment. One possible role is as an early-acting microbicide that destroys the functional virus particle before encounter and consequent infection of host cells. Therapeutically, the peptides could help clear viruses in circulation. Suppressing the amount of circulating virus could decrease virus spread from infected to uninfected individuals. Therapeutic intervention of this type may ultimately benefit from optimized formulations that enable adequate delivery and metabolic stability.

Observations made in this work suggest that multivalent display of peptide triazoles may be important for the virucidal effect against HIV-1 virus. An impressive enhancement of p24 release was shown with AuNP/KR13 conjugate, which contains an average of 72 moles of peptides attached per mole of nanoparticle. Since the Cys-SH group of KR13 in the AuNP-KR13 conjugate is coordinated to gold, the virucidal functions of peptide and conjugate are unlikely to be due to the free sulfhydryl component per se. On the other hand, KR13 alone has the potential to dimerize to a disulfide crosslinked dimer, and this latter could be the agent causing p24 release in unconjugated KR13. Supporting this idea, the parent peptide triazole HNG156, while being a strong inhibitor of cell infection by virus, did not appear to elicit significant, dose-dependent p24 release. Neither AuNP alone nor AuNP attached to thiol-polyethylene glycol were able to elicit antiviral or virucidal actions against the virus particle (data not shown). In one aspect, formation of stable dimers and other well-defined multivalent peptide triazoles are important objectives to pursue going forward for developing peptide triazoles as virucidal agents.

The ability to exert ligand-specific, cell-free virucidal effects on HIV-1 particles by the gp120 targeting peptide triazoles may be related to the ability to induce Env conformational changes in an intrinsically metastable virus. The HIV-1 infection process is driven by a cell entry machine in which virus and host cell proteins engage in a sequence of interactions and conformational changes, leading to virus-host cell fusion. A major and apparently obligatory phase of this process is the large-scale, receptor-induced conformational rearrangement of Env protein that enables exposure of fusogenic components on the virus surface (Sattentau et al., 1993, Philos. Trans. Royal Soc. B, 342:59-66; Fass, 2003, Adv. Protein Chem. 64:325-362; Liu et al., 2003, Peptides 24:1303-1313; Cerutti et al., 2010, J. Biol. Chem. 285:25743-25752). Prior data have shown that soluble CD4 and CD4-mimicking small molecules, both of which can exert large conformational changes in Env gp120 similar to those induced by cellular CD4, are able to inactivate the virus in a time-dependent manner in the absence of cells (Haim et al., 2009, PLoS Pathog. 5:e1000360). Further, polyvalent CD4 has been observed by cryoelectron tomography to crosslink simian immunodeficiency virus particles with associated virion rupture (Bennett et al., 2007, J. Biol. Chem. 282: 27754-27759). The current work indicates that modified peptide triazole allosteric inhibitors—an emerging class of gp120 antagonists that exert substantial conformational effects on the Env gp120 protein—can cause cell-free disruption of HIV-1 virus particles, leading to their inactivation. In the peptide triazole case, this inactivation is specific for an allosteric site unique to HIV-1 virions and leads to ligand-specific virus particle rupture. Such cell-free virucidal action through specific inhibitor attack on the conformationally metastable viral envelope machine opens up new directions for HIV-1 treatment and prevention.

In summary, the modified peptide triazole inhibitors described herein target HIV-1 gp120 to physically disrupt virus particles in the absence of host cells. At conditions similar to those at which the peptide triazole KR13 inhibited HIV-$1_{BaL}$ pseudovirus infection of HOS.T4.R5 cells, it also caused release of HIV-1 gag p24 when incubated with virus alone. Both inhibition of cell infection and p24 release were enhanced substantially by multivalent display of KR13 on gold nanoparticles. Virucidal function of the modified peptide triazoles argues for their potential use as microbicidal and therapeutic agents to suppress the progression and spread of AIDS. The results also suggest that ligand-specific pathogen rupture may be possible for other viruses such as influenza, ebola and dengue, which contain metastable prefusion surface protein complexes (Kielian & Rey, 2006, Nat. Rev. Microbiol. 4:67-76).

Example 5

Characterization of AuNP Conjugates

The studies described herein help understand the fundamental spatial and rigidity characteristics of peptide triazole AuNPs that can be modulated to promote virucidal function; the molecular and physical transitions of the HIV-1 virion Env that occur in NP-induced virolysis; the relationship of virolysis to virus cell entry; and the potential of stabilizing the peptide triazole AuNPs to improve their usefulness at sites of therapeutic or microbicidal intervention. The studies have the following objectives:

Determine Rules of Spatial Geometry and Surface Rigidity of Gold Nanoparticle—Peptide Triazole (AuNP-PT) that Promote Cell-Free HIV-1 Virolysis:

Using coordinated virus infection and p24 leakage assays, the effects on virus particles of multivalent AuNP-PT nanoparticles of distinct sizes and surface densities of peptide triazole are determined to identify geometries of AuNP-PT that lead to maximum virucidal effects. Additionally, the effects of NP surface rigidity, using AuNPs with PT attached through variably flexible linkers, are determined.

Determine the Relationship Between AuNP-PT Induced HIV-1 Virolysis and the Virus Cell Fusion Process that Leads to Infection:

To better understand the intrinsic mechanism of virolysis, the time-dependence of effects of AuNP-PTs on molecular and physical transitions that occur in the metastable HIV-1 virion are measured, including gp120 shedding (ELISA), release of intraviral components (ELISA for p24, enzymatic activity for HIV-1 RT), loss of membrane integrity (TEM) and loss of cell infection activity. In order to relate these effects to those of cell infection, the impact of Env mutations on the virolytic effect by AuNP-PTs versus their impact on infection are compared. In addition, the extent to which AuNP-PT causes exposure of Env protein epitopes that are expected to arise during fusion and cell infection is examined.

Establish Fundamental Stability and Cell Transport Properties of AuNP-KR13 Nanocompositions:

Modifications of AuNP-PTs that result in stabilized forms for the mucosal environment are evaluated, and the ability to transport such forms across gut and vaginal epithelial cells, as well as their effects on host antimicrobial responses, is established. Stabilization by hydrogel encapsulation is also evaluated. The effect of virucidal NP on host defensin and secretory leukocyte protease inhibitor expression by gut and vaginal epithelial cells is analyzed. These data are used as a predictor for penetration of mucosal layers and activity at sites of virus infection and proliferation in vaginal and gut-associated lymphoid tissue.

Overall, this work derives principles for designing multivalent Env-targeting NPs to enable virucidal actions that are specific for HIV-1. The NPs help expand understanding of the extent to which the Env metastability, which is critical for pathogenic host cell entry, can be hijacked for therapeutic and microbicide functions. The results provide precedent for how other gp120 inhibitor-NP compositions may be devised for HIV-1 virus inactivation, as well as how ligand-specific pathogen rupture may potentially be achieved for other viruses (such as influenza, ebola and dengue) that contain metastable prefusion surface protein complexes.

As described elsewhere herein, the peptide triazole KR13 (Arg Ile Asn Asn Ile X Trp Ser Glu Ala Met Met βA Gln βA Cys-NH$_2$, X=ferrocenyltriazolePro), containing a free cysteine group, was attached to AuNP nanoparticles to yield a multivalent conjugate. KR13 itself has a somewhat greater antiviral activity than HNG156 (Bastian et al., 2011, Chem Med Chem 6, 1335-1339). 20 nm monodisperse AuNPs were synthesized using a modified citrate reduction method, and KR13 was conjugated to the AuNP using a direct gold-thiol covalent link (FIG. 2). The HIV-1 viral entry inhibition potencies of KR13 and AuNP-KR13 conjugates were compared using a single-round pseudoviral infection luciferase reporter assay using lab synthesized pseudoviruses. The effects of KR13 and AuNP-KR13 on the virus particle itself were tested by measuring release of the nucleocapsid protein p24 using Western blot analysis of cell-free virion inhibition. Compared to KR13, AuNP-KR13 conjugate exhibited enhanced infection inhibition activity, with IC$_{50}$ value of 1±0.1 nM and 23±6 nM respectively (Bastian et al., 2011, Chem Med Chem 6:1335-1339). The lack of inhibition of cell infection by control VSV-G pseudotype virus demonstrated that the viral inhibition by AuNP-KR13 was specific for HIV-1 envelope. There was no significant in vitro cytotoxicity observed for AuNP-KR13. Strikingly, Western blot analyses revealed a concentration dependent p24 release by AuNP-KR13. This effect was not seen at all with VSV-G pseudotype, nor was it seen by the monovalent HNG156. Hence, AuNP-KR13 was able to target HIV-1 gp120 to physically disrupt virus particles in the absence of host cells. KR13 on its own could cause virolysis, though with lower potency than AuNP-KR13, while HNG156 could not. Without using to be limited by theory, KR13 may form disulfide-containing dimers, and this bivalent peptide form leads to the somewhat greater antiviral potency of KR13 versus HNG156 as well as the p24 release activity of KR13. KR13 with its CysSH grouped blocked was no longer virolytic.

Example 6

Nanoparticle Technology Used to Design Virolytic Agents for Delivery and Treatment The results with KR13 and AuNP-KR13 suggest that specific virolytic agents are possible and that AuNP-KR13 provides a high potency lead opportunity to expand understanding of this potential. Defining the fundamental properties of AuNP-KR13 and its derivatives may help guide the design of a new class of anti-HIV-1 agents that could inactivate viruses in situ. However, there is still much to be investigated about the virolytic function disclosed herein.

Spatial Properties of NP-PT (Nanoparticle-Peptide Triazole) Conjugates

The spatial characteristics of size of the AuNPs and related peptide triazole density of KR13 on the AuNP surface could be important determinants of events that occur at the virus-NP interface, yet the spatial properties at provide optimum activity may be further investigated at this stage.

Nanoparticle-PT Surface Rigidity

Tethering peptide triazole to AuNPs through such linkers as PEG (polyethylene glycol) could enhance or suppress the ability of the AuNP-KR13 to induce the virolytic activity depending on the roles of NP surface constraint versus ligand adaptability. Linkers between NP surface and peptide triazoles may be incorporated with variable lengths and degrees of flexibility.

Proof of Principle for Demonstration of Stabilization and Transport of AuNP-PTs

The PTs disclosed herein may be susceptible to proteolysis. Hence, there is a need for approaches to protect AuNP-KR13 (for example, by hydrogel encapsulation for controlled release) and enables protected/released AuNP-PT compositions to penetrate mucosal cells that represent important sites of viral infection and T cell loss.

Relationship of the HIV-1 Virolytic Process to Virus-Cell Fusion

The PT-induced lysis of HIV-1 triggered by multivalent NP compositions may well rely on the intrinsic metastability of the mature virus and of the Env protein spike on the virus. At the same time, metastability is likely important in the cell entry process itself, through receptor-induced rearrangements in the spike protein of the envelope as a part of the virus-cell fusion mechanism. It may thus be that virolysis and fusion both involve common intrinsic properties of the virus. Understanding molecular events of virolysis by AuNP-KR13 could provide insights into the features of the virus and Env spike that would make them vulnerable to antagonist actions leading to virus inactivation.

Overall, these studies allow to: (1) obtain design guidelines for virolytic AuNP-PT compositions, (2) relate the virolytic approach of HIV-1 killing to fundamental properties the virus uses for cell entry and (3) establish proof-of-principle demonstration for the ability to stabilize and transport virolytic AuNP-PT compositions to sites important to control virus infection and proliferaton.

Example 7

Studies

HIV-1 Specific Virolysis as a Preventative or Therapeutic Strategy

The present studies define a new family of agents able to specifically lyse HIV-1 in the absence of host cells. Such agents could inactivate virus at the earliest stages of HIV-1 exposure, in a different manner than complement-mediated lysis, which requires a cascade of host cell interactions (Sullivan et al., 1996, J. Immunol. 157:1791-1798; Asa-Chapman et al., 2005, J. Virol. 79:2823-28300). Cell free virolytic agents that can lyse HIV-1 by either viral membrane penetration or lipid degradation were previously reported. These include small molecule LJ001 (Wolf et al., 2010, Proc. Natl. Acad. Sci. USA 107:3157-31620), C5A, a peptide from NS5A protein of hepatitis C virus (Bobardt et al., 2008, Proc. Natl. Acad. Sci. USA 105:5525-5530) and phospholipase $A_2$-X (Kim et al., 2007, J. Virol. 81:1444-1450). Importantly, though, these previously described agents are general rather than HIV-1 specific, since they target virus-like membranes and hence affect other viruses and potentially host cell domains enriched in cholesterol and phosphocholine. The approach herein specifically targets HIV envelope specifically.

Activation of Immune System Via p24 Release In Situ

The ability of AuNP-KR13 to induce p24 release and introduce gold-based nanoparticles at localized sites of HIV-1 accumulation opens up the possibility to prime the immune system for cytotoxic T-lymphocyte response at sites of infection. Directed T-cell responses are crucial for the control of HIV infection (Hober et al., 1999, Scand. J. Immunol. 50:83-90; Masemola et al., 2004, J. Virol. 78:3233-3243; Martinez-Picado et al., 2006, J. Virol. 80:3617-3623; Zuniga et al., 2006, J. Virol. 80:3122-3125; Kiepiela et al., 2007, Nature Medicine 13:46-53; Ndongala et al., 2009, Clin. Immunol. 131:277-287), while Gag p24 from HIV-1 is a strong inducer of directed T-cell responses (Hober et al., 1999, Scand. J. Immunol. 50:83-90; Masemola et al. 2004, J. Virol. 78:3233-3243; Zuniga et al., 2006, J. Virol. 80:3122-3125; Kiepiela et al., 2007, Nature Medicine 13:46-53; Ndongala et al., 2009, Clin. Immunol. 131, 277-287). Immune responses to p24 have also been associated with establishing the viral load set point for patients (Masemola et al., 2004, J. Virol. 78:3233-3243), as well as driving the selection of escape mutants toward epitopes with decreased fitness (Martinez-Picado et al., 2006, J. Virol. 80:3617-3623). Gold nanoparticles themselves have been found to activate the immune system (Tomii & Masugi, 1991, Jpn. J. Med. Sci. Biol. 44:75-80; Kreuter, 1995, Pharm. Biotechnol. 6:463-472). AuNP peptide conjugates were found to enhance macrophage activation Bastus et al., 2009, Mol. Immunol. 46:743-748), and AuNP was found to be useful as an adjuvant for initiating immune response. The virolysis associated with AuNP-KR13 class compositions would provide sufficient quantities of p24 antigen to stimulate cytotoxic T-lymphocytes in the body (Bastian et al., 2011, Chem Med Chem 6:1335-13390). Overall, since the entry of HIV-1 and the production of the latent viral reservoirs after active infection all occur in CD4 T-cells and macrophages (Stevenson, 2003, Nat. Med. 9:853-8600), the enhanced activation of the immune system by AuNP-PT could boost a localized immune response against the virus.

Long-Lasting Nanoparticle-Based Anti-HIV Agents that can Penetrate Mucosa

The current studies help develop nanoparticle-containing anti-HIV-1 agents with improved half-lives compared to unconjugated inhibitors. Such half-life increase would reduce the frequency for HIV-1 drug administration, and this technology would help alleviate problems of non-compliance by patients on retroviral therapies. Stabilization of immunogens by conjugation with nanoparticles has been observed in several studies (das Neves et al., 2010, Adv. Drug Deliv. Rev. 62:458-477), including PSC-RANTES (Ham et al., 2009, Pharm. Res. 26:502-511). While AuNP compositions have been aimed at increasing potency through inhibitor multivalency (Bowman et al., 2008, J. Am. Chem. Soc. 130:6896-6897). Gold NPs are themselves inert and have been tested as carriers to improve the stability of inhibitors of HIV-1 reverse transcriptase (RT), protease (PR) and viral entry into host cells (Fonteh et al., 2010, Biometals 23:185-196).

A potential caveat in using AuNP-KR13 as an HIV-1 virucide may be limited drug stability of the peptide component in vivo due to proteolytic degradation. While peptidomimetic strategies are being explored in parallel (Moreira et al., 2011, unpublished), the peptide stability barrier may be overcome by using stimuli-sensitive hydrogels that may both protect the drug and provide localized diffusion-controlled release. Prior evidence has shown that complexation hydrogels comprised of poly(methacrylic acid) (PMAA) grafted with poly(ethylene glycol) (PEG) may improve the bioavailability of insulin administered orally (Lowman et al., 1999, J. Pharm. Sci. 88:933-937). These networks exhibit pH-dependent swelling due to formation of reversible interpolymer complexes that form at near-neutral and basic pH (Lowman & Peppas, 1997, Macromolecules 30:4959-4965). P(MAA-g-EG) and other pH-responsive hydrogels have been investigated as carriers for a variety of proteins and peptides (Kamei et al., 2009, J. Contr. Rel. 134:98-102; Kavimandan et al., 2006, Biomat. 27:3846-3854; Morishita et al., 2002, J. Contr. Rel. 81:25-32), including HIV-1 protease inhibitors (De Jaeghere et al., 2000, J. Contr. Rel. 68:291-298; Leroux et al., 1996, Pharm. Res. 13:485-487). Furthermore, prior evidence has shown that PEG may help transport agents into mucosal tissues (Lai et al., 2007, Proc. Natl. Acad. Sci. USA 104:1482-1487), and recent data (Pasut et al., unpublished) shows that PEG conjugation to PTs can improve plasma half-lives of peptide triazoles. Despite these findings, pH-responsive hydrogels have never been tested with AuNP's conjugated with HIV-1 virucides. The current work uses P(MAA-g-EG) complexation hydrogels to enhance the stability of AuNP-PT's by protecting the drug from enzymatic degradation and enabling controlled release. Since these networks have also exhibited the ability to bind to mucosa (Goto et al., 2006, J. Pharm. Sci. 95:462-469) and reversibly permeate the tight junctions of epithelial cells (Ichikawa & Peppas, 2003, J. Biomed. Mat. Res. Part A 67:609-617), release from P(MAA-g-EG) hydrogels may also improve the transport of AuNP-PTs across mucosa and cell monolayers, improving the bioavailability. Since a preponderance of HIV-1 destruction of T-cells occurs in early infection stages in mucosal tissues, identifying agents that can target and penetrate mucosal sites is a critical need. The AuNP-KR13 family of compounds may help identify a novel class of mucus-penetrating agents.

Mechanism of Virolysis

Figure 17:
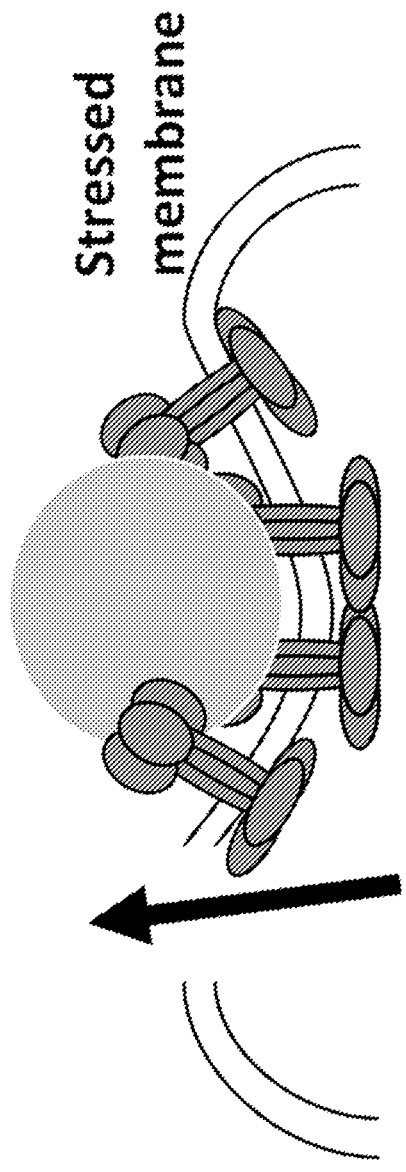
FIG. 17 illustrates a hypothetical model of how AuNP-KR13 may rupture HIV-1 by binding specifically and multivalently to Env via peptide triazoles and stressing virus membrane leading to rupture.

This study helps reveal mechanistic understanding of the specific virolysis of HIV-1, a working model illustrated in FIG. 17. The study should reveal the roles of localized multivalency and rigidity on the AuNP-KR13 surface in effecting the virolytic process, the relationship of virolysis to fundamental properties of the virus that are used for infection, and vulnerable steps in the pathogenesis that could be targeted for drug discovery.

Figure 18C:
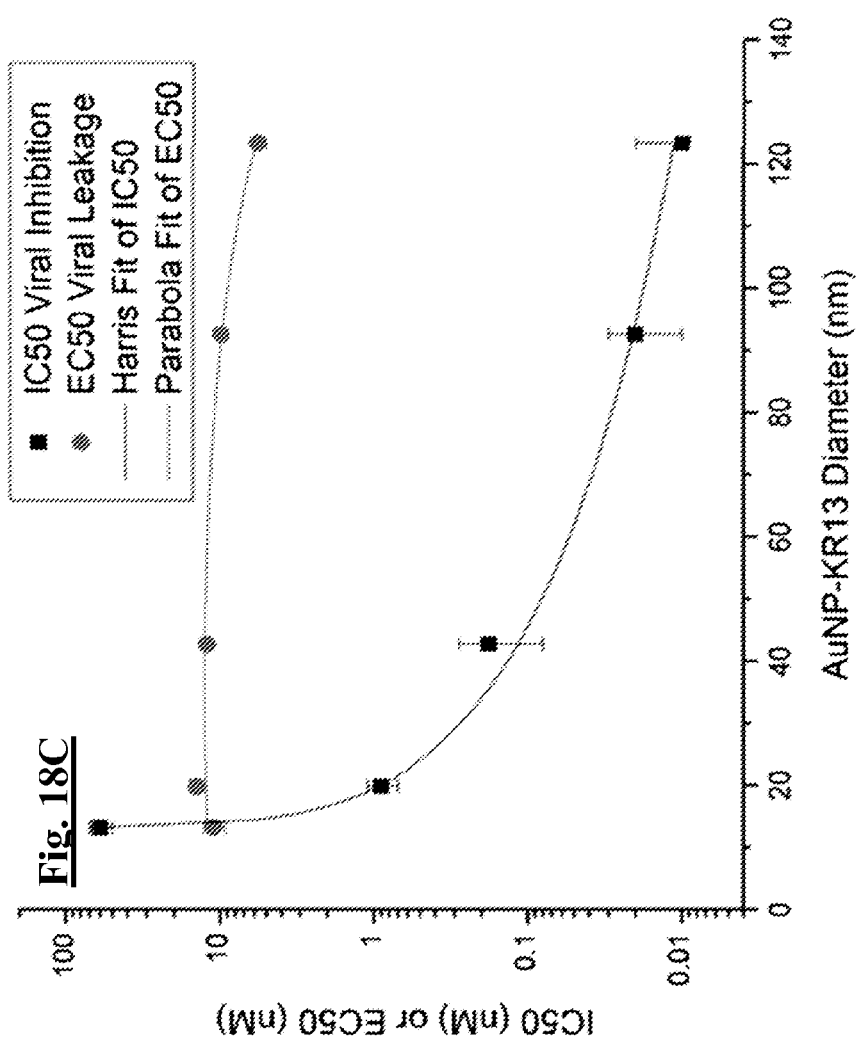

AuNP-PT compositions may help guide design and development of HIV-1 specific virolytic agents for therapeutic and prevention applications. However, the rules for design should be defined, and the potential of such molecules as AuNP-PTs to be stabilized as well as to access sites of HIV-1 occurrence during the infection process should be demonstrated. The relationship between HIV-1 virolysis and virus-cell fusion should be defined, as this may help identify vulnerable properties of virus and stages of cell entry that could be targeted generally.

Example 8

Determination of Rules of Spatial Geometry and Surface Rigidity of Gold Nanoparticle—Peptide Triazole (AuNP-PT) that Promote Cell-Free HIV-1 Virolysis Using coordinated virus infection and p24 leakage assays, the effects on virus particles of multivalent AuNP-PT nanoparticles of different sizes and inhibitor surface densities are determined, in order to optimize geometries of AuNP-PT that lead to maximum virucidal effects. Additionally, the effects of NP surface rigidity are determined, using PT attached to variably flexible polyethylene glycol (PEG) linkers on AuNPs. From this, guidelines that govern design of peptide coated gold nanoparticles for HIV-1 entry inhibition and virolysis are derived.

Controlling Gold Nanoparticle Size

As the size of AuNPs is increased, increased curvature of the AuNP-virus interface may increase access in the number of KR13 molecules to virus envelope binding sites, and that this may lead to increased virolysis. Multivalent inhibitors have highly localized concentrations of inhibitors that increase viral Env interactions, as previously seen with other antiviral inhibitor-AuNP compositions (Bowman et al., 2008, J. Am. Chem. Soc. 130:6896-6897). To test the effects of nanoparticle size on viral inhibition and virolytic activity, gold nanoparticles (AuNP) are synthesized with diameters ranging from 10-200 nm. After AuNP functionalization with the KR13 peptide, assays on HIV cell infectivity and cell-free leakage of virus contents are used to correlate nanoparticle diameter and surface area to the AuNP-KR13's antiviral activities.

Spherical AuNPs of controlled diameters are synthesized and stabilized as previously reported (Frens, 1973, Nature 241:2). Briefly, 1% $HAuCl_4$ is added to filtered water and heated to 100° C. for 1 h, followed by addition of 0.5-2% citric acid. The synthesized particles are stabilized using bis-(p-sulfonatophenyl) phenylphosphine dehydrate dipotassium salt (BSPP, Strem Chemicals) and transferred into phosphate buffer (pH 7.2) using a Millipore 10,000 MWCO filter. The particle size distribution is measured using dynamic light scattering (DLS; Zetasizer NS90, Malvern Instruments), and the structural properties of the particles is evaluated using transmission electron microscopy (TEM) imaging (JEM 2100 operated at 200 kV). Particle concentration is calculated using the absorbance at 450 nm and the diameter dependent epsilon determined by Haiss et al. using the multipole scattering theory (Anal. Chem. 2007, 79:4215-4221). Using the above methodologies, sizes 10-120 nm with monodisperse diameter distributions are routinely achieved.

Peptide synthesis of KR13 and other peptide triazoles (scrambled sequence, longer linkers, etc.) is carried out using already-established protocols (Gopi et al., 2008, J. Med. Chem. 51:2638-2647; Gopi et al., 2006, Chem Med Chem 1:54-57; Cocklin et al., 2007, J. Virol. 81:3645-3648). Peptide conjugation to the AuNPs is achieved via covalent linkage between the thiol moiety (—SH) on C-terminal cysteine residue and the gold surface of AuNP's (Bastian et al., 2011, Chem Med Chem 6:1335-1339; Contarino et al., 2006, J. Mol. Recogn. 19:363-371). Briefly, 1:1000 molar ratio of BSPP-stabilized AuNP:peptide in phosphate buffer is stirred together for 30 minutes at 25° C. Excess peptide is removed from the nanoparticle fraction via a 10,000 MWCO centrifugation filter. Nanoparticles are flash frozen, lyophilized and sent for amino acid analysis to determine the amount of peptide bound per nanoparticle. For AuNPs with a diameter of 20 nm, an average of ~72 peptide molecules per nanoparticle is typically achieved.

To evaluate the functional effects of AuNP-KR13 on virus, single round infectious virions are produced by co-transfection into HEK293T cells of pNL4-3.Luc R-E-vector with a panel of env genes from Clades A (92UGO37.8, QA013.H1), B (BaL, HxBc) and C(DU172.17, Cap210.200.E8) (NIH AIDS reagent program) according to previous methods (McFadden et al., 2011, unpublished; Montefiori, 2005, Curr. Protoc. Immunol. Chapter 12, Unit 12-11). Budded virions are purified in a two-step methodology from 0.45 μm-filtered supernatants, ensuring that only fully-assembled virus particles are used for the functional assays. First, soluble proteins (env, p24, etc.) is removed via fractionation on 6-20% sucrose gradient for 2 hours at 30,000 rpm, followed by anti-CD45 (clone h5a5, Developmental Studies Hybridoma Bank) affinity chromatography to remove any contaminating exosomes (Ott et al., 2009, Meth. Mol. Biol. 485:15-250). Purified viral preparations are normalized according to p24 content using p24 ELISA (Zeptometrix 0801111) and assayed for infectivity with the luciferase reporter gene assay (Montefiori, 2005, Curr. Protoc. Immunol. Chapter 12, Unit 12-11; Umashankara et al., 2010, Chem Med Chem 5:1871-1879). Using this method, 10-20 mL amounts of virus with a $10^5$ dynamic range of luciferase activity are obtained when infecting HOS.T4.R5 cells with serial dilutions of purified virus. Once an acceptable dilution of viral titer is determined, the infection assay is carried out with serial dilutions of the AuNP-PTs normalized to peptide concentration. Experiments are run in triplicate. Nonlinear regression analysis performed by Origin v.8.1 (OriginLab, Northampton, USA) is used to calculate the EC50 values for each AuNP diameter (d), as seen in FIG. 18A. Controls include naked nanoparticles, inhibitors alone and scrambled PT-AuNP (sPT-AuNP) treatments for experimental comparison. Virions containing VSV-G envelope, which enters via endocytosis, are used as a control for HIV-1 envelope specificity. Toxicity of nanocomposite compounds is monitored using WST-1 assay (Mosmann, 1983, J. Immunol. Meth. 65:55-63).

The release of viral capsid protein p24 is monitored using a capture ELISA assay. Purified virus is treated with AuNP-KR13 compositions for thirty minutes at 37° C. and spun in a microcentrifuge for 2 hours at 13,000 g at 4° C. The supernatant is isolated from the pellet, and both are stored at 4° C. PBS at 37° C. is used as negative control for background signal, and viruses incubated for 5 minutes with 1% Triton-X at 100° C. are positive control for p24 release. High binding, polystyrene ELISA plates (Fisher Scientific, 21-377-203) are coated overnight at 4° C. with 50 ng of mouse anti-p24 (Abcam, 9071) and blocked with 3% BSA. Following PBS-T rinsing, serial dilutions of the supernatants are incubated and detected using 1:4000 dilutions of rabbit anti-p24 (Abcam 63913) and anti-rabbit IgG fused to horseradish peroxidase (HRP) (Amersham Biosciences NA934V). Controls include leakage caused by AuNP, sPT-AuNP, and PT alone, and FIG. 18B shows results obtained for the p24 leakage triggered by a set of AuNP-KR13 nanoparticles with differing diameters. The hypothesized increased leakage with nanoparticle size was observed in BaL (Glade B), and the correlation held when results were normalized for KR13 content on the nanoparticles. Nanoparticle size-dependence of both inhibition of virus cell infection (FIGS. 18A and 18C) and virolysis (FIGS. 18B and 18C) are formalized into mathematical relationships as follows:

$IC_{50}$ Viral Infectivity=$f_1(d)$ and $EC_{50}$ Viral Lysis=$f_2(d)$, where $f_x(d)$ are functions of diameter determined by fitting the data to diverse mathematical models available in Origin 8.0 to a minimum of triplicate experiments. Models that go to convergence over multiple iterations that minimize residuals to under 5% of total signals are deemed appropriate. For example, theoretical functions for the $IC_{50,BaL}$ and $EC_{50,BaL}$ in terms of nanoparticle diameter have been determined to be $$f_1(d)=(-0.7483+0.00312d^{2.1328})^{-1}$$ and $$f_2(d)=11.376+0.06485d-8.944d^2$$

respectively (FIG. 18C). Results for HIV-1 viruses containing different subtypes of Env protein are compared to define the breadth of the virolytic process.

Modulating Nanoparticle Surface Density of Peptide Triazoles

As the surface density of peptide triazole increases, the AuNP-PT may bind more envelope spikes simultaneously, leading to increased virus inactivation and p24 release. At a critical peptide surface density, steric hindrance may play an important role in determining the maximum number of envelope spikes per virus bound, and additional peptide coverage could be unnecessary or even detrimental for desired inactivation and virucidal effects. To evaluate this correlation, peptide triazole inhibitor coverage on 20 nm diameter Au nanoparticles is varied by mixing different molar ratios of KR13 and L-cysteine during the step of peptide conjugation to AuNP. Both molecules present a single reactive thiol for covalent attachment to the BSSP-stabilized nanoparticle, however only KR13 binds to HIV envelope glycoproteins on the surface of the virion.

Figures 19A, 19B:
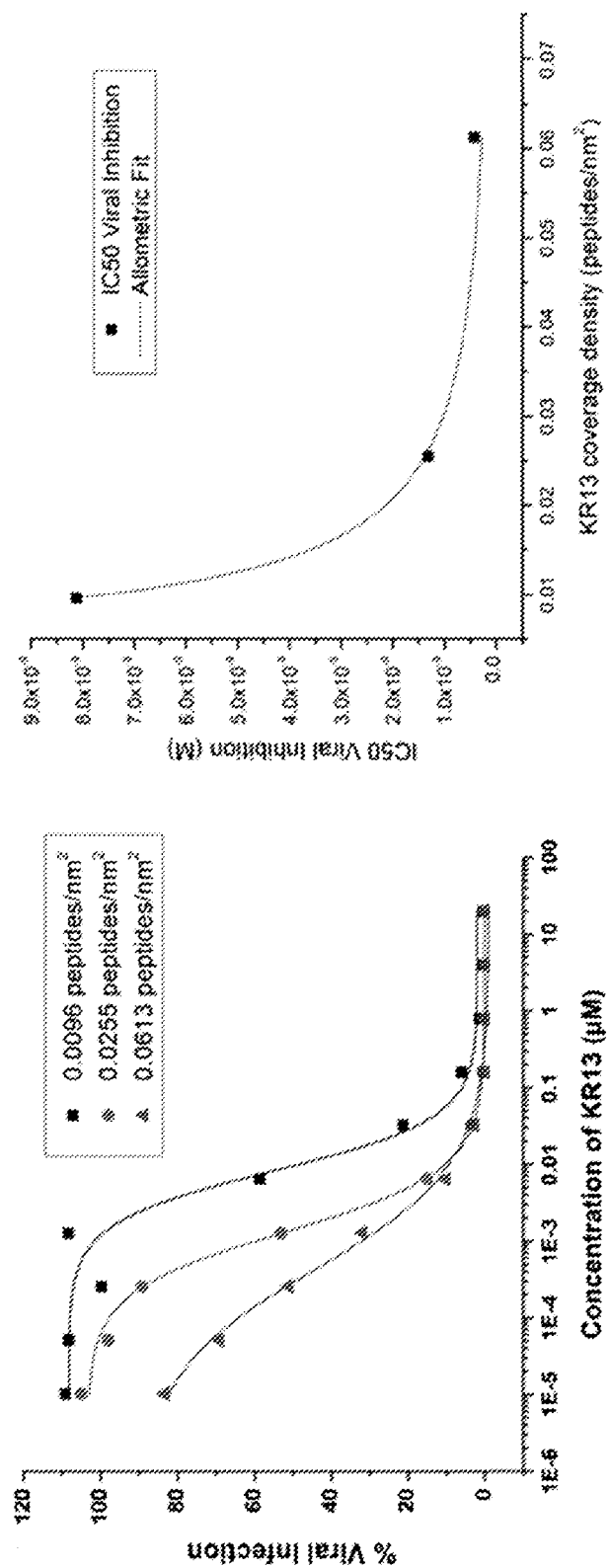
FIGS. 19A-19B illustrate the density dependent inhibition of BaL pseudovirus (FIG. 19A) and $IC_{50}$ against peptide coverage density plot with an allometric fit of the data (FIG. 19B).

AuNP and KR13 are synthesized and functionalized as described herein, except that cysteine/KR13 is added in varying molar ratios, from 0:1000 to 1000:0 in increments of 50. The density of peptide coverage ($\rho_{coverage}$) is calculated by the relationship:

$$\rho_{coverage}=[C_{peptide}/C_{AuNP}]/4\pi(d/2)^2$$

where $4\pi(d/2)^2$ is surface area of nanoparticle and $C_{peptide}/C_{AuNP}$ is molar ratio of peptides per nanoparticle. HIV and VSV enveloped pseudotyped virus encoding a luciferase reporter gene are used to assay the ability to block infection on HOS.T4.R5 cells. Nanoparticles with varying peptide triazole coverages are also evaluated in the p24 leakage assay. Controls mirror those recited elsewhere herein for both the peptide surface density infection and leakage assays. These data lead to the derivation of the relationships:

$IC_{50}$ Viral Infectivity=$f_1(\rho_{coverage})$ and $EC_{50}$ Viral Lysis=$f_2(\rho_{coverage})$ where $f_x(\rho_{coverage})$ is a function of coverage density determined by fitting the data in Origin 8 to a minimum of triplicate experiments as described elsewhere herein. In FIGS. 19A-19B, the ability to vary peptide coverage density on 20 nm diameter AuNPs is demonstrated, resulting in change in inhibition of viral infection.

Assessing Roles of Rigidity and Flexibility of the Peptide Triazole Surface on Nanoparticles Increased flexibility may increase peptide triazole availability for virus surface envelope protein encounter, while increased rigidity may increase virolysis-causing stress of the virus surface. The present study addresses whether rigidly tethered peptide triazole (AuNP-PT) and the transition to flexibly tethered peptide triazole (AuNP-PEG-PT) are more favorable for cell-free virolysis. Thiol presenting PEG molecules is used to coat the NP surface and present a single reactive maleimide moiety for further covalent conjugation to PT inhibitors. The NP composition with hard Au core and flexible PEG shell enables a flexible movement of covalently linked PT.

Compounds SH-PEG$_{xx}$-COOH with varying sizes (MW$_{avg}$=10-5000 Da) from Nanocs are used to vary surface flexibility of peptide triazoles (Otsuka et al., 2003, Adv. Drug Del. Rev. 55:403-419). PEG molecules are attached to stabilized AuNPs by vigorous stirring at room temperature for 30 minutes at a PEG concentration determined by flocculation assay. The critical flocculation concentration (CFC) of PEG was determined, as the threshold concentration of the electrolyte (NaCl) in the AuNP solution that caused rapid aggregation of the particles, followed by a 10-fold excess of 2-maleimidoethylamine trifluoroacetate linker (Sigma-Aldrich 56951) for 2 hours with 200 mM NHS and 50 mM EDC at pH=6.0 (Grabarek et al., 1990, Anal. Biochem. 185:131-135). Coverage of the thiol-PEGs is verified from particle size and zeta potential measurements using Zetasizer NS90 (Malvern Instruments, Malvern, UK). Surface charge densities closer to zero indicates a higher degree of PEG coverage (Hwu et al., 2008, J. Phys. D. Appl. Phys. 41). Dynamic light scattering is used to determine the effective diameter of the AuNP-PEG particles. Once PEG is attached, KR13 is covalently attached via the C-terminal cysteine to the maleimide on AuNP-PEG, followed by ultracentrifugation and dialysis to remove non-covalently attached peptide triazole. Amino acid analysis and absorbance measurements at 450 nm are used to determine attached peptide and nanoparticle concentrations respectively (Haiss et al., 2007, Anal. Chem. 79:4215-4221).

In coordination with the above functional analyses, atomic force microscopy (AFM) is used to determine the Modulus of Elasticity (E) for AuNP-KR13 and AuNP-PEG$_{5000}$-KR13. E defines the ability of an object to deform along an axis when opposing forces are applied along that axis. This quantity, which is derived from single point deformations in atomic force microscopy (AFM), may be used as a quantitative measure to relate PEG mobility to both viral inhibition and virolysis. Using the linear range of the resultant force displacement curves, AFM can derive several key variables that can then be used to calculate E of the nanoparticles using the relationship:

$$E = \frac{3F(1-v_2^2)}{4h_2^3}\left(\frac{R_2+R_2}{R_1R_2}\right)^{\frac{1}{2}} E = \frac{3F(1-v_2^2)}{4h_2^3}\left(\frac{R_2+R_2}{R_1R_2}\right)^{\frac{1}{2}}$$

where E is the Modulus of Elasticity, F is the force applied by the AFM tip, $v_2$ is the Poisson ratio of gold ($v_2$=0.32; Kanjanaboos et al., 2011, Nano. Lett. 11:2567-2571), h is the indentation depth (defined as the piezo displacement minus the cantilever deflections), and $R_1$ and $R_2$ are the radius of curvature and radius of the AFM tip and AuNP, respectively (Tan et al., 2004, Langmuir 20:7015-7020). Gold nanoparticles are immobilized through appropriate silanes onto AFM grade mica slides by adapting established protocols (Cheng et al., 2002, Anal. Chem. 74:3599-3604; Bezanilla et al., 1995, Langmuir 11:655-659). Force curves are obtained on regions that have 3-D images of nanoparticles using a Digital Instruments Bioscope/Nikon Eclipse TE2000-U AFM system with NanoScope IIIa v5.12r5 software (Veeco Instruments, Inc., Plainview, N.Y.), fitted with Bruker MSNL silicon tip probes (Bruker AFM Probes, Type F) featuring a spring constant of 0.6 N/m. Viral inhibition and leakage properties are validated for nanoparticles used for these experiments. This data lead to derivation of the relationships:

IC50 Viral Infectivity=$f_1(E)$ and

EC50 Viral Lysis=$f_2(E)$ where $f_x(E)$ is a function of the Modulus of Elasticity determined by fitting the data to a minimum of triplicate experiments. Lower E values may correlate with larger molecular weight PEG linkers and gradually return to values close to AuNP-KR13 with shorter and more rigid PEG linkers. Linear PEG of MW 5000 Daltons has been successfully linked to 20 nm diameter AuNP, with subsequent covalent attachment of KR13. This initial AuNP-$PEG_{5000}$-KR13 composition is still inhibitory towards HIV-$1_{BaL}$ but has decreased virolytic (FIGS. 20A and 20B). In preliminary analyses using AFM, values of $E_{AuNP}$=5.86±1.19 GPa (n=4) and $E_{AuNP-PEG}$=2.47±0.41 GPa (n=4) were obtained as shown in FIGS. 20C and 20D. These values are similar, respectively, to data reported for AuNPs and protein-coated AuNPs (Wampler & Ivanisevic, 2009, Micron 40:444-448).

Outcomes

The present study yields guidelines for designing AuNP-KR13 virolytic nanoparticles with controlled size, peptide triazole surface coverage and degree of surface rigidity. One issue that may arise in achieving this overall goal is finding indefinite conditions for maximum effects due to non-specific side effects of the surface components. If this occurs, smaller stabilizers than BSPP are investigated, such as 2-mercaptoethanol, oleylamide, decanethiol, etc. (Huo, 2007, Colloids Surf. B Biointerfaces 59:1-10; Liu et al., 2007, Colloids Surf. B Biointerfaces 58:3-7). If rigidity is found to be a major constraint for virolysis, shorter branched or dendrimeric PEG, or even more conformationally constrained linkers such as polyproline linkers of KR13 to AuNP, are investigated (Braun et al., 2007, J. Am. Chem. Soc. 129:7760-7761; Welch et al., 2007, Proc. Natl. Acad. Sci. USA 104:16828-16833).

Example 9

Determination of Relationship Between AuNP-PT Induced HIV-1 Virolysis and Virus Cell Fusion Process that Leads to Infection The time-dependence of effects of AuNP-PTs on molecular and physical transitions that occur in the metastable HIV-1 virion is measured, including gp120 shedding (ELISA), release of intraviral components [ELISA for p24, enzymatic activity for HIV-1 reverse transcriptase (RT)], and loss of cell infection activity. In order to relate these effects to those of cell infection, the impact of Env mutations on the virolytic effect by AuNP-PTs is compared to their impact on infection. In addition, the extent to which AuNP-PT causes exposure of Env protein epitopes that are expected to arise during fusion and cell infection is analyzed. Finally, changes induced in virus morphology by TEM and cryoEM that occur in virolysis are investigated and correlated to those changes occurring with receptor-based ligands.

Time Dependence of Physical Effects of AuNP-KR13 on HIV-1 and Envelope

In the course of productive infection, it is thought that gp120 is shed from the heterotrimeric spike as a mechanism to both elicit non-neutralizing antibodies and expose the fusion peptide domain on gp41 to help bridge the viral and host membranes during the cell infection process (Rits-Volloch et al., 2006, EMBO J. 25:5026-5035; Ruprecht et al., 2011, J. Exp. Med. 208:439-454). It has been demonstrated in preliminary experiments that AuNP-KR13 also triggers gp120 shedding (FIG. 21). Based on this finding, the time course of gp120 shedding by AuNP-KR13 is evaluated in comparison to CD4-triggered shedding, and these shedding events are correlated with time dependence of release of intraviral contents and inhibition of virus cell infection (Poignard et al., 1996, J. Exp. Med. 183:473-484).

Shedding of gp120 from pseudovirus is evaluated using an ELISA approach. Inhibitor samples are incubated with the working dilution of the pseudovirus (obtained from infection titer) for 0-1440 minutes. Intact virus is detected by incubating with 1×PBS, and lysed virus is quantified by incubating 1% Triton-X for 5 min at 95° C. (t=0) with the virions. Following incubation, the samples are spun at 4° C. for 2 hours, followed by collection of the supernatant (which may be stored at 4° C. until further analysis). ELISA detection of the supernatant is conducted using primary anti-gp120 (D7324) and secondary anti-sheep HRP (Zymax, 81-8620). Controls with lysed virus and buffer alone, and those without primary and secondary antibodies, are included to ensure specificity of assay. Envelopes from clades A (92UGO37.8, QA013.H1), B (BaL, HxBc) and C (DU172.17, Cap210.200.E8) are tested to demonstrate the breadth of AuNP-KR13 effects (McFadden et al., 2011, unpublished). Untreated (negative) and sCD4-treated (positive) viruses are used as controls.

The time dependence of cell-free release of intraviral components is also measured and compared to the time dependence for both gp120 shedding and loss of cell infection activity. These data help develop a time sequence for the disruptive effects of AuNP-KR13, and expands understanding of how the virolytic effect occurs mechanistically and how virolysis relates to what is known of the composition of HIV-1 Env spike and the known disruptive effects of CD4 and other gp120 ligands. In this part of the work, release profiles for both intraviral proteins p24 and reverse transcriptase are evaluated. The preliminary data (FIG. 21) indicate that the release of p24 using AuNP-PTs occurs relatively rapidly, though not as much so as gp120 shedding. However, it is unclear if the released p24 is from the capsid core or instead the interstitial areas between viral membrane and capsid. Additional monitoring of the release of reverse transcriptase (RT), from the viral core, is used to differentiate between release of interstitial proteins and total release of all viral contents.

The p24 release assay described elsewhere herein is modified to measure time dependence of p24 release with varying incubation time of virus and AuNP-KR13 at 37° C. from 0-1440 minutes. The time dependent release of RT from nanoparticle-treated and -untreated virions is monitored using EnzCheck Reverse Transcriptase Assay Kit according to the manufacturer's protocols (Molecular Probes, E-22064). Controls for rupture specificity include naked (no KR13, replaced by Cys-SH) nanoparticles, inhibitors alone, sCD4 treatments and non-enveloped and VSV-G enveloped NL4-3 (HIV-1) virions for experimental comparison. Since CD4 is not known to cause virolysis, while multivalent CD4 indicates virolysis may occur (Bennett et al., 2007, J. Biol. Chem. 282:27754-27759), the latter is used to test for relatedness between AuNP-KR13 virolysis and that caused by a receptor-related ligand.

Effects on Virolysis of Mutations in HIV-1 Env Expected to Disrupt Entry and Infection Envelope mutations that suppress virus cell fusion and entry leading to infection have previously been identified. The effect of such mutations is evaluated on virolysis caused by AuNP-PTs. Specific mutations are introduced by site-directed mutagenesis (QuikChange, Agilent Technologies) into Env genes and confirmed by sequencing. Mutated viral stocks of Clades A, B and C are produced and assayed for time dependence of gp120 shedding, p24/RT release and inhibition of infection by the assays elsewhere herein.

For gp120, the H66N mutation, which reduces neutralization by sCD4 roughly 33-fold through conformational effects on the gp120 protein that putatively alter gp120-gp41 interactions, is initially investigated (Kassa et al., 2009, J. Virol. 83:8364-8378). AuNP-KR13 induced virolysis of this mutant is measured to determine the extent to which conformational change in the Env spike is also important for the virolytic process. As a positive control, D474 is mutated to alanine, which has strongly abrogated PT efficacy while retaining sCD4 binding and cell infection activity (Tuzer et al., 2011, unpublished). This mutation should lead to suppression of the AuNP-KR13 virolytic effect.

Virolysis is also evaluated for further pseudotype mutants that have alterations in the gp41-gp120 interface, membrane promixal external region (MPER) and cytoplasmic domain, which have previously been found to decrease virus entry and infectivity. The W610F mutant completely abrogates gp120-gp41 association and prevents fusion. The G597A mutation also prevents fusion and viral entry, but may have reduced levels of associated gp120 (Poumbourios et al., 2003, J. Biol. Chem. 278:42149-42160). These changes in gp120 lability may well modulate virolysis by AuNP-KR13 if the latter functions through gp120 interaction mechanism. The L669S mutation prolongs the exposure of MPER and makes the virus >250 times more sensitive to neutralization by 2F5 and 4E10 (Shen et al., 2010, Proc. Natl. Acad. Sci. USA 107: 5972-5977). Prolonged exposure may affect virolysis, indicating that MPER plays a role in virolysis. Cytoplasmically, the Y712C mutation has been shown to increase surface expression of Env and lead to decreased fusogenicity (Bhakta et al., 2011, Retrovirol. 8:370). Increased Env expression elucidates how trimer density affects AuNP-KR13 virolysis.

Exposure of Known Spike Protein Epitopes Upon Virolysis

The productive entry process of HIV-1 is a well-studied process in which CD4 binding leads to exposure of a coreceptor site on gp120. In turn, this leads to gp41 epitope exposure in the heptad repeat, membrane proximal external region (MPER) and fusion peptide regions. Using an immunoprecipitation assay (Saah et al., 1987, J. Clin. Microbiol. 25:1605-1610; Olshevsky et al., 1990, J. Virol. 64:5701-5707; Helseth et al., 1990, J. Virol. 64:2416-2420), the extent to which AuNP-KR13 treatment of viruses leads to exposure of epitopes similar to those triggered during fusion and entry, is investigated, including sites for CD4, bridging sheet, V3 loop, MPER, Heptad Repeat 1 (HR1), HR2 and fusion peptide.

Fixative procedures (Yuan et al., 2006, J. Virol. 80:6725-6737) and the antibodies from NIH AIDS reagents are used to assay the time dependent exposure of gp120 and gp41 conformational transitions. Antibodies against gp120 include 17B, F105, m18, A32, VRC1, B4A1 and 2G12. Antibodies against gp41 include F240, 98-6, 2F5 and 4e10. The conformations by SDS-PAGE are analyzed, followed by Western blot analysis. Band intensities using densitometry analysis (Image J) are utilized to correlate these data between epitopes exposed using sCD4 (Gassmann et al., 2009, Electrophoresis 30:1845-1855). These studies further highlight the conformational transitions that differ from paths that lead to productive entry versus those that lead to viral lysis.

Morphological Characterization of Nanoparticle Effects

CD4 and polyvalent CD4 have been previously shown to cause both envelope protein rearrangements and macroscopic morphological changes in HIV-1. Since AuNP-KR13 causes virolysis, the nanoparticle-peptide triazole also may cause significant morphological changes. These changes are imaged using both transmission electron microscopy (TEM) and cryo-electron microscopy (cryo-ET). Macroscopic changes reflect the intrinsic fragility of the virus, which is believed to be an important feature in the entry process (Bennett at al., 2007, J. Biol. Chem. 282:27754-27759). Preliminary data have provided direct observation for binding of AuNP-KR13 to virus particles (FIGS. 22A & 22B). >70% of the AuNP-KR13 found in the field of view were directly adjacent to viral membrane, within the ~20 nm of Env present on the viral membrane surface. The virions used in FIGS. 22A & 22B are treated with AT-2 (aldrithiol-2), which dissolves the core proteins leading to no retroviral infectivity while preserving the structural and functional properties of the virus env (Rossio et al., 1998, J. Virol. 72:7992-8001). Though the virions used in that study lacked capsid cores, they nonetheless provide precedent that the effects of AuNP-KR13 may be imaged.

For TEM, virus prepared as described elsewhere herein are incubated with AuNP-KR13 for various times (0-30 min), fixed using 2% glutaraldehyde, resuspended in 2% liquid agar and spread on a clean glass slide to solidify. The agar is sliced to 1 mm$^2$ squares, dehydrated by sequential exchange into acetone from 50%-100% and embedded into epoxy and polymerized 100° C. for 1 hour (Stadtlander & Kirchhoff, 2004, Scanning 26:175-180). Imaging is done using a JEOL TEM at 200 keV. Energy Dispersive X-Ray Spectroscopy (EDAX) is used to confirm the presence of gold and viral materials in specific image locations. FIGS. 22 C & 22D demonstrate feasibility to image virus in the presence and absence of AuNP-KR13. Interestingly, the TEM data argue that treated virus loses not only p24 but also a well-defined core. Further incubation time increases this event and leads to little well-defined virus and substantially more aggregated material. On average, >80% of the viruses treated with AuNP-KR13 contained no well-defined viral core. EDAX confirmed co-localization of gold and viral elements. Statistical analysis of TEM images was conducted using minimum n=50 virions. All samples used 20 nm AuNP-KR13 conjugates at 10 nM concentration. In addition to imaging the effects of AuNP-KR13, comparative imaging analysis is made with multivalent CD4, based on prior results (Bennett et al., 2007, J. Biol. Chem. 282:27754-27759) demonstrating that the latter can also disrupt virus morphology.

Outcomes

The results may help define how the virolytic action of multivalent AuNP-KR13 nanoparticles may be related to the normal events of pathogenesis, including time-dependent disruption of the env protein and virus particle, effects of mutations, epitope exposure and virus morphology. It is likely that some mutations do not affect virolysis, but still hinder viral entry and infection. This may help appreciate the relationship of virolysis to the events expected to occur in pathogenesis.

Still, to deepen the analysis, the mutations may be expanded to include other events of productive infection, including exposure of gp41 fusion peptide and collapse of trimeric gp41 into the 6-helix bundle. Analysis of these conformational epitope exposures with matching antibodies in immunoprecipitation assays may be extended. The TEM methodologies used to study the morphological changes to the virus may be expanded by introducing more advanced cryo-TEM techniques that maintain the viral integrity with minimized sample preparation artifacts.

Example 10

Establishment of Fundamental Stability and Cellular Transport Properties of AuNP-KR13 Nanocompositions Modifications of AuNP-PT's that result in stabilized forms for the mucosal environment are identified, and the ability to transport such forms across gut and vaginal epithelial cells, as well as their effects on host antimicrobial responses, is established. Stabilization by hydrogel encapsulation is evaluated. The effect of virucidal NP on host defensin and secretory leukocyte protease inhibitor expression by gut and vaginal epithelial cells are determined. These data are used as a predictor for their ability to penetrate mucosal layers and be active at sites of virus infection and proliferation in vaginal and gut-associated lymphoid tissue.

Stability and Controlled Release of AuNP-KR13

Peptide drugs may suffer from rapid degradation in vivo due to the ubiquitous presence of peptidases and proteases. This may be subdued, however, by encapsulation in hydrogels, which may offer several advantages for the nanoassemblies. First, the hydrogel should act as a shield against peptidases and proteases in either oral or vaginal delivery schemes. Second, hydrogel encapsulation may be used to control the release of AuNP-KR13 to maintain an effective therapeutic dosage over long periods of time. Third, hydrogels exhibiting mucoadhesive properties should increase the residence time of peptides and enable local delivery at mucosal absorption sites. Lastly, hydrogels should promote peptide transport across cell monolayers by locally and reversibly permeating the tight junctions of epithelial cells (Lowman et al., 1999, J. Pharm. Sci. 88:933-937).

The AuNP-KR13 nanocompositions are modified to increase stability, and enable controlled release, by encapsulation in a pH-responsive hydrogel. In one embodiment, the hydrogel is synthesized by UV-initiated free radical polymerization of methacrylic acid (MAA, Sigma-Aldrich Chemical Co.) and poly(ethylene glycol) monomethyl ether monomethacrylate (PEGMA, Polysciences, Inc.) in the presence of the photoinitiator 1-hydroxy-cyclohexyl-phenyl-ketone (Irgacure 184, BASF) (modified from Kavimandan et al., 2006, Biomat. 27:3846-3854; Morishita et al., 2002, J. Contr. Rel. 81:25-32). The monomer solution is dispersed between two glass slides, separated by Teflon spacers and polymerized for 1 hour by irradiation at 365 nm using a high intensity longwave UV lamp (Blek-Rey® B-100AP). The ensuing physically crosslinked hydrogels is purified in deionized (DI) water for 1 week, vacuum dried, grounded to a powder and sieved to 45-125 μm. $^1$H NMR is used to characterize the P(MAA-g-EG) hydrogels.

Hydrogels are loaded with AuNP-KR13 (Kavimandan et al., 2006, Biomat. 27:3846-3854; Morishita et al., 2002, J. Contr. Rel. 81:25-32). Briefly, a concentrated solution of P(MAA-g-EG) microparticles is prepared in phosphate buffer, pH 7.2, and adjusted to pH 7.4 using NaOH. Various concentrations of AuNP-KR13 are mixed with the hydrogel solution and sonicated until uniformly dispersed. Equilibrium partitioning proceed over varying times, and the hydrogel is collapsed using HCl, resulting in P(MAA-g-EG) microparticles loaded with AuNP-KR13. The particles are filtered, rinsed with a 50% v/v solution of DI water and HCl, and dried under vacuum. Naked AuNPs serve as a control. The loading efficiency is calculated based on the concentration of nanoassemblies before and after encapsulation, while TEM and EDS confirms the presence of AuNP-KR13 inside the hydrogels.

The AuNP-KR13 and hydrogel encapsulated nanoassemblies are exposed to simulated mucus as well as mucus-secreting HT29-MTX goblet cells (Dr. Lesuffleur, INSERM UMR S 938, Paris, France). To create simulated duodenal mucus, pancreatin (a cocktail of protease, lipase and amylase, Sigma-Aldrich) in a 50% glycerol-water solution is used to mimic the viscous mucosal layer.

Encapsulated and non-encapsulated nanoassemblies are mixed with the mucus-like cocktail over varying times. Non-encapsulated particles are purified by salt precipitation, centrifugation and resuspension in phosphate buffer. Encapsulated AuNP-KR13 is centrifuged and resuspended in phosphate buffer, pH 11, to enable AuNP-KR13 release, followed by centrifugation and collection of the supernatant. Treated samples, purified from pancreatin and mucosal washes, are exposed to both the viral inhibition and viral lysis assays. This procedure is repeated using simulated vaginal mucus (Owen & Katz, 1999, Contraception 59:91-95), containing aminopeptidase (Sigma-Aldrich Chemical Co.) (Rohan & Sassi, 2009, AAPS J. 11:78-87). The stability of peptides is investigated over a range of temperatures and pH's, and the half-life ($t_{1/2}$) of effective compounds is computed in all enzymatic solutions in terms of both viral inhibition and viral lysis. Controls include naked AuNPs and peptide alone. Hydrogel encapsulated AuNP-KR13 is expected to avoid much of the degradation in simulated mucus and retain a higher degree of viral inhibition and lytic properties, since pancreatin and aminopeptidase should inactivate non-encapsulated KR13.

The release rate of encapsulated nanoassemblies is characterized by measuring the concentration of AuNP-PTs released from P(MAA-g-EG), overtime, in phosphate buffers of pH range 2-11. UV-Vis spectroscopy (450 nm) is used to measure the AuNP concentration released, while amino acid analysis confirms the concentration of KR13. These data are used to calculate the fractional release of nanocompositions from the hydrogels. Since P(MAA-g-EG) hydrogels exhibit a pKa around 4.8, encapsulated nanocompositions are expected to be released only when the hydrogels are exposed to near-neutral or basic pH environments. For encapsulated d=20 nm AuNPs in hydrogels prepared by the methods above, using sodium phosphate buffered solutions of pH 3, 7 and 11, pH-dependent nanoparticle release was demonstrated (FIGS. 23A-23B). This is indicated by the absorbance increases at 450 nm with increasing pH.

Transport of AuNP-KR13 Through Mucosal Cells

The transport mechanisms of different AuNP-KR13 nanoassemblies through mucosal tissues are also studied because these sites are reservoirs for HIV infection. Recently, Lin et al. (Biomacromolecules 2011, 12:1339-1348) reported that nanoparticles coated with neutrally-charged polymers, such as PEG, exhibited increased translocation across Caco-2 monolayers, and reduced TEER values corresponding to temporary disruption of intercellular tight junctions. PEG is also reported to have mucoadhesive capacities, which can be used in P(MAA-g-EG) networks to prolong the residence time of AuNP-KR13 near absorption sites (Goto et al., 2006, J. Pharm. Sci. 95:462-469). The goal here is to determine if the compositions have the ability to reach sites that are rapidly depleted of CD4+ lymphocytes in new infections. The translocation of AuNP-KR13 and PEGylated AuNP-KR13 across gut and vaginal epithelial cell monolayers, in both the presence and absence of P(MAA-g-EG) hydrogels, is thus investigated.

To model absorption through the gut epithelium, a co-culture of absorptive Caco-2 cells and mucus-secreting HT29-MTX goblet cells is used. Co-cultures are seeded on Transwell® inserts (Corning) at a density of $1\text{-}5\times10^5$ cells per insert (Hilgendorf et al., 2000, J. Pharm. Sci. 89:63-75; Pontier et al., 2001, J. Pharm. Sci. 90:1608-1619), and cultured until confluent. Monolayers are equilibrated in transport buffer (Kavimandan et al., 2006, Biomat. 27:3846-3854; Walter et al., 1996, J. Pharm. Sci. 85:1070-1076), then fresh transport buffer is added to the basolateral chamber and varying concentrations of AuNP-KR13 are added to the apical chamber. Initial and final concentrations are sampled from the apical chamber, and at varying time points, 100 µL are sampled from the basolateral chamber. The transepithelial electrical resistance (TEER) is measured to monitor the formation of intercellular tight junctions, identify the transport mechanism of nanoparticles, and assess hydrogel and nanoparticle cytotoxicity. Transport across epithelial barriers may occur by a transcellular pathway, such as diffusion or endocytosis, or by a paracellular pathway, involving transport through tight junctions. Temporary reductions in TEER values indicate the disruption of intercellular tight junctions by the hydrogel and/or nanoparticle and subsequent paracellular transport, while permanent reductions in TEER suggest damage to the cell monolayer and damage to the epithelium barrier. Consistent TEER values are indicative of transcellular transport, which may be confirmed using TEM to identify cell internalization of AuNP-KR13, as described previously (Lin et al., 2011, Biomacromol. 12:1339-1348). An MTT assay confirms the cytocompatibility observed from the TEER measurements.

To quantify transport, AuNP-KR13 concentrations are measured using UV-Vis spectroscopy, and the apparent permeability of the nanocomposition is calculated. Transport is visualized under dark field microscopy, which can easily identify AuNPs and confirm maintenance of tissue morphology. Naked AuNPs serve as a control. This study is repeated using papillomavirus-immortalized human vaginal keratinocytes, VK2/E6E7, to model absorption through the female genital tract epithelium. In both models, transport is expected to occur primarily through the paracellular pathway. Naked AuNP-PTs are expected to require the presence of hydrogels for transport to occur, while PEGylated nanocompositions are expected to transport in the absence of P(MAA-g-EG), with enhanced transport resulting from hydrogel presence. Both P(MAA-g-EG) and AuNP-PT's are biocompatible; therefore, cytotoxicity is not anticipated (Bastian et al., 2011, Chem Med Chem 6:1335-1339; Torres-Lugo et al., 2002, J. Contr. Rel. 80:197-205).

Effect of Nanoassemblies on Host Defense Processes

HIV-1 virucides exposed to mucosal surfaces must inhibit infection without disrupting mediators of antiviral activity, which provide the host with an inherent ability to resist infection. To address this issue, the effects of AuNP-KR13 nanoparticle compositions on two major classes of antimicrobial peptides, namely defensins and secretory leukocyte protease inhibitor (SLPI) (Herold et al., 2011, Am. J. Reprod. Immunol. 65:325-333) are quantified. Both mediators are known to contribute to mucosal immunity and are expressed by Caco-2 and VK2/E6E7 epithelial cells. Caco-2 and VK2/E6E7 cell lines are cultured in Transwell® inserts until confluent monolayers are formed, which is confirmed by measuring the TEER. The monolayers are treated with a serial dilution of the AuNP-PT nanocompositions, and the basolateral compartment of the Transwells® is collected and assayed, as described previously (Gali et al., 2010, J. Virol. Meth. 165: 186-197; Ou et al., 2009, Scand. J. Immunol. 69:150-161; Si-Tahar et al., 2000, Gastroenter. 18:1061-1071). Levels of human β-defensins 2-3 and SLPI expression are quantified using both real-time reverse transcriptase polymerase chain reaction (RT-PCR), as well as enzyme-linked immunosorbent assay (ELISA). Due to the intrinsic ability of AuNPs to activate the innate immune response, the nanocompositions are not expected to suppress mediators of antiviral activity. Instead, AuNP-PTs may promote innate immunity, resulting in increased expression of defensins and SLPI.

Outcomes

The aim is to provide proofs of principle that stabilization of AuNP-KR13 and transport through mucosal cell layers may be achieved. The acidic pH of vaginal fluid may inhibit the release of AuNP-KR13 from P(MAA-g-EG) hydrogels. However, the alkalinity of seminal fluid is known to neutralize the vaginal pH, which would enable peptide release during-coitus (Lai et al., 2009, J. Virol. 83:11196-11200). Therefore, the swelling behavior of hydrogel encapsulated AuNP-KR13 in simulated vaginal fluid, pH 4-5, is quantified, and its release by addition of simulated seminal fluid is studied. If insufficient release is observed with the proposed methods, in either simulated duodenal or vaginal fluids, biodegradable polymer carriers, such as poly(lactic acid)-chitosan (Dev et al., 2010, Carb. Pol. 80:833-838), are explored. In addition to potential problems of AuNP-PT release, insufficient AuNP-KR13 transport across epithelial cell monolayers may happen. To promote the transport of the nanoassemblies, the molar ratio of PEGMA may be increased during the synthesis of the hydrogels, and this may increase mucoadhesion and temporarily disrupt epithelial tight junctions. This may enhance paracellular transport of AuNP-KR13.

The disclosures of each and every patent, patent application, and publication cited herein are hereby incorporated herein by reference in their entirety.

While the invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A composition comprising a peptide of formula (II) or a salt thereof:

```
(I),                                  (SEQ ID NO: 2)
Arg Ile Asn Asn Ile X Trp Ser Glu Ala Met Met βA
Gln βA Cys-NH₂,
``` wherein: X is (2,4)-4-(4-ferrocenyl-1H-1,2,3-triazol-1-yl) pyrrolidine-2-carboxylic acid, and βA is beta-alanine.

2. The composition of claim 1, further comprising at least one gold nanoparticle, wherein the at least one nanoparticle is complexed to the peptide of formula (II) through the Cys thiol group of SEQ ID NO:2.

3. The composition of claim 1, further comprising at least one additional compound for treating viral infections.

4. The composition of claim 1, wherein the peptide is encapsulated in a hydrogel.

5. A method of preparing a derivatized gold nanoparticle, wherein the gold nanoparticle is complexed with a binding molecule or a salt thereof, the method comprising:
  contacting a solution of the binding molecule with the nanoparticle to generate a reaction system;
  stirring the reaction system for an amount of time, whereby the derivatized gold nanoparticle is formed; and
  isolating the derivatized gold nanoparticle from the reaction system,
  wherein the binding molecule comprises a peptide of formula (II) or a salt thereof:

```
(II),                                 (SEQ ID NO: 2)
Arg Ile Asn Asn Ile X Trp Ser Glu Ala Met Met βA
Gln βA Cys-NH₂,
``` wherein X is (2,4)-4-(4-ferrocenyl-1H-1,2,3-triazol-1-yl)pyrrolidine-2-carboxylic acid, and βA is beta-alanine;
  wherein the nanoparticle is complexed to the peptide of formula (II) through the Cys thiol group of SEQ ID NO:2.

6. A method of promoting virolysis of a virus in a mammal, wherein the virus is selected from the group consisting of human immunodeficiency virus type 1 (HIV-1), influenza, ebola and dengue, the method comprising administering to the mammal a therapeutically effective amount of a composition comprising at least one pharmaceutically acceptable carrier and at least one gold nanoparticle, wherein the gold nanoparticle is complexed with a binding molecule or a salt thereof, wherein the binding molecule comprises:
  a peptide of formula (II) or a salt thereof:

```
(II),                                 (SEQ ID NO: 2)
Arg Ile Asn Asn Ile X Trp Ser Glu Ala Met Met βA
Gln βA Cys-NH₂,
``` wherein X is (2,4)-4-(4-ferrocenyl-1H-1,2,3-triazol-1-yl)pyrrolidine-2-carboxylic acid, and βA is beta-alanine;
wherein the nanoparticle is complexed to the peptide of formula (II) through the Cys thiol group of SEQ ID NO:2;
whereby virolysis of the virus in the mammal is promoted.

7. The method of claim 6, wherein the mammal is further administered at least one additional compound for treating viral infections.

8. The method of claim 6, wherein the peptide is encapsulated in a hydrogel.

9. The method of claim 6, wherein the mammal is human.

10. A method of reducing the rate of or inhibiting entry of a virus into a cell of a mammal, wherein the virus is selected from the group consisting of human immunodeficiency virus type 1 (HIV-1), influenza, ebola and dengue, the method comprising administering to the mammal a therapeutically effective amount of a composition comprising at least one pharmaceutically acceptable carrier and at least one gold nanoparticle, wherein the gold nanoparticle is complexed with a binding molecule or a salt thereof, wherein the binding molecule comprises
  a peptide of formula (II) or a salt thereof:

```
(II),                                 (SEQ ID NO: 2)
Arg Ile Asn Asn Ile X Trp Ser Glu Ala Met Met βA
Gln βA Cys-NH₂,
``` wherein X is (2,4)-4-(4-ferrocenyl-1H-1,2,3-triazol-1-yl)pyrrolidine-2-carboxylic acid, and βA is beta-alanine;
wherein the nanoparticle is complexed to the peptide of formula (II) through the Cys thiol group of SEQ ID NO:2;
whereby the entry of the virus into the cell of the mammal is inhibited or takes place at a reduced rate as compared to an untreated mammal.

11. The method of claim 10, wherein the mammal is further administered at least one additional compound useful for treating viral infections.

12. The method of claim 10, wherein the peptide is encapsulated in a hydrogel.

13. The method of claim 10, wherein the mammal is human.

14. A method of reducing or treating infection of a virus in a mammal, wherein the virus is selected from the group consisting of human immunodeficiency virus type 1 (HIV-1), influenza, ebola and dengue, the method comprising administering to the mammal a therapeutically effective amount of a composition comprising at least one pharmaceutically acceptable carrier and at least one gold nanoparticle, wherein the gold nanoparticle is complexed with a binding molecule or a salt thereof, wherein the binding molecule comprises
  a peptide of formula (II) or a salt thereof:

```
(II),                                 (SEQ ID NO: 2)
Arg Ile Asn Asn Ile X Trp Ser Glu Ala Met Met βA
Gln βA Cys-NH₂,
``` wherein X is (2,4)-4-(4-ferrocenyl-1H-1,2,3-triazol-1-yl)pyrrolidine-2-carboxylic acid, and βA is beta-alanine;
wherein the nanoparticle is complexed to the peptide of formula (II) through the Cys thiol group of SEQ ID NO:2;
whereby the infection of the virus in the mammal is reduced or treated.

15. The method of claim 14, wherein the mammal is further administered at least one additional compound for treating viral infections.

16. The method of claim 14, wherein the peptide is encapsulated in a hydrogel.

17. The method of claim 14, wherein the mammal is human.

* * * * *